United States Patent
Kapadia et al.

(10) Patent No.: US 9,492,623 B2
(45) Date of Patent: *Nov. 15, 2016

(54) APPARATUS AND METHOD FOR TARGETING A BODY TISSUE

(71) Applicants: THE CLEVELAND CLINIC FOUNDATION, Cleveland, OH (US);
(Continued)

(72) Inventors: Samir Kapadia, Chagrin Falls, OH (US); Marwane Berrada, Quebec (CA);
(Continued)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/060,256

(22) Filed: Oct. 22, 2013

(65) Prior Publication Data
US 2014/0114245 A1 Apr. 24, 2014
US 2015/0374932 A9 Dec. 31, 2015

Related U.S. Application Data

(63) Continuation-in-part of application No. 13/206,639, filed on Aug. 10, 2011, now Pat. No. 8,694,077, which
(Continued)

(51) Int. Cl.
*A61M 5/42* (2006.01)
*A61B 17/34* (2006.01)
(Continued)

(52) U.S. Cl.
CPC .......... *A61M 5/427* (2013.01); *A61B 17/3403* (2013.01); *A61B 17/3478* (2013.01);
(Continued)

(58) Field of Classification Search
CPC ................... A61B 19/5244; A61B 2019/5251; A61B 6/481; A61B 6/504; A61M
(Continued)

(56) References Cited

U.S. PATENT DOCUMENTS 5,171,228 A 12/1992 McDonald
5,279,583 A 1/1994 Shober et al.
(Continued)

FOREIGN PATENT DOCUMENTS

EP 0531081 A1 3/1993
WO 9605768 A1 2/1996
(Continued)

OTHER PUBLICATIONS

Calkins, Hugh et al., A Practical Approach to Catheter Ablation of Atrial Fibrillation, 2008, p. 67, last viewed on Oct. 18, 2013.
(Continued)

*Primary Examiner* — Emily Schmidt
*Assistant Examiner* — William Frehe
(74) *Attorney, Agent, or Firm* — Tarolli, Sundheim, Covell & Tummino LLP

(57) ABSTRACT

An apparatus for targeting a desired target site on a body tissue comprising a wall of a first body cavity of a patient includes a target catheter. A framing member has a collapsed condition and an expanded condition. The framing member has a framing member body which includes a bulbous portion defining a maximum body footprint having proximal and distal body ends which are both longitudinally spaced from the maximum body footprint. The framing member is comprised of a plurality of framing member beams. At least three framing member beam arrays of framing member beams are arranged in non-overlapping longitudinal sequence to form at least a portion of the framing member. The framing member beams that make up the framing
(Continued)

member substantially each have a width-to-thickness fractional ratio in the range of 0.6-3.0.

13 Claims, 32 Drawing Sheets

(71) Applicants: Bavaria Medical Technology, Canada Inc., Boucherville (CA)

(72) Inventors: Cesar Fuentes-Ortega, Dartmouth (CA); Daniel Wing Fai Mok, Mississauga (CA)

Related U.S. Application Data is a continuation-in-part of application No. 11/867,774, filed on Oct. 5, 2007, now Pat. No. 8,019,404.

(60) Provisional application No. 61/716,690, filed on Oct. 22, 2012, provisional application No. 61/716,693, filed on Oct. 22, 2012, provisional application No. 61/716,699, filed on Oct. 22, 2012, provisional application No. 61/716,705, filed on Oct. 22, 2012, provisional application No. 61/716,716, filed on Oct. 22, 2012, provisional application No. 61/716,723, filed on Oct. 22, 2012, provisional application No. 61/716,651, filed on Oct. 22, 2012, provisional application No. 60/850,147, filed on Oct. 6, 2006.

(51) Int. Cl.
*A61B 17/00* (2006.01)
*A61B 18/00* (2006.01)
*A61B 17/22* (2006.01)

(52) U.S. Cl.
CPC ...... *A61B 34/20* (2016.02); *A61B 2017/00243* (2013.01); *A61B 2017/00247* (2013.01); *A61B 2017/00252* (2013.01); *A61B 2017/22069* (2013.01); *A61B 2017/22095* (2013.01); *A61B 2017/3405* (2013.01); *A61B 2017/3411* (2013.01); *A61B 2017/3488* (2013.01); *A61B 2018/0038* (2013.01); *A61B 2018/00279* (2013.01); *A61B 2018/00351* (2013.01); *A61B 2018/00357* (2013.01); *A61B 2018/00386* (2013.01); *A61B 2034/2051* (2016.02)

(58) Field of Classification Search
CPC ............... 25/0108; A61M 25/09041; A61M 2025/09175; A61M 25/0417; A61M 25/007
USPC .......................................... 600/424, 433–435
See application file for complete search history.

(56) References Cited

U.S. PATENT DOCUMENTS

| | | | |
|---|---|---|---|
| 5,391,199 A | 2/1995 | Ben-Haim | |
| 5,487,758 A | 1/1996 | Hoegnelid et al. | |
| 6,254,586 B1 | 7/2001 | Mann et al. | |
| 6,260,552 B1 | 7/2001 | Mortier et al. | |
| 6,332,089 B1 | 12/2001 | Acker et al. | |
| 6,337,995 B1 | 1/2002 | Mower | |
| 6,622,730 B2 | 9/2003 | Ekvall et al. | |
| 6,650,923 B1 | 11/2003 | Lesh et al. | |
| 6,652,556 B1 | 11/2003 | Vantassel | |
| 6,709,382 B1 | 3/2004 | Horner | |
| 6,740,076 B2 | 5/2004 | Hoben et al. | |
| 6,945,978 B1 | 9/2005 | Hyde | |
| 6,974,436 B1 | 12/2005 | Aboul-Hosn et al. | |
| 6,994,093 B2 | 2/2006 | Murphy et al. | |
| 6,994,094 B2 | 2/2006 | Schwartz | |
| 7,101,362 B2* | 9/2006 | Vanney | A61B 18/1492 600/152 |
| 8,019,404 B2* | 9/2011 | Kapadia | A61B 17/3478 600/407 |
| 8,235,986 B2 | 8/2012 | Kulesa et al. | |
| 8,694,077 B2* | 4/2014 | Kapadia | A61B 17/3478 600/407 |
| 2002/0107445 A1 | 8/2002 | Govari | |
| 2003/0018246 A1 | 1/2003 | Govari et al. | |
| 2003/0083742 A1 | 5/2003 | Spence et al. | |
| 2003/0163153 A1 | 8/2003 | Scheib | |
| 2003/0192561 A1 | 10/2003 | Murphy et al. | |
| 2004/0019447 A1 | 1/2004 | Shachar | |
| 2004/0158143 A1 | 8/2004 | Flaherty et al. | |
| 2004/0220471 A1 | 11/2004 | Schwartz | |
| 2004/0243122 A1 | 12/2004 | Auth et al. | |
| 2005/0075723 A1 | 4/2005 | Schroeder et al. | |
| 2005/0149097 A1 | 7/2005 | Regnell et al. | |
| 2005/0154250 A1 | 7/2005 | Aboul-Hosn et al. | |
| 2005/0228452 A1 | 10/2005 | Mourlas et al. | |
| 2005/0257796 A1 | 11/2005 | Ellis et al. | |
| 2006/0025800 A1* | 2/2006 | Suresh | A61B 17/0057 606/198 |
| 2007/0123852 A1 | 5/2007 | Deem et al. | |
| 2008/0249397 A1* | 10/2008 | Kapadia | 600/424 |
| 2009/0043228 A1* | 2/2009 | Northrop | A61M 25/0013 600/585 |
| 2011/0313283 A1 | 12/2011 | Kapadia | |
| 2013/0310804 A1 | 11/2013 | Jabba et al. | |
| 2014/0012228 A1 | 1/2014 | Jabba et al. | |

FOREIGN PATENT DOCUMENTS

| | | | |
|---|---|---|---|
| WO | 03028558 A2 | 4/2003 | |
| WO | 03028558 C1 | 4/2003 | |
| WO | 03075793 A1 | 9/2003 | |
| WO | 2004110307 A2 | 12/2004 | |
| WO | 2004110307 A3 | 12/2004 | |
| WO | 2005007036 A1 | 1/2005 | |
| WO | 2005055849 A1 | 6/2005 | |
| WO | 2005072627 A1 | 8/2005 | |
| WO | 2005113419 A2 | 12/2005 | |
| WO | 2007044285 A2 | 4/2007 | |
| WO | 2008070262 A2 | 6/2008 | |
| WO | 2010069562 A1 | 6/2010 | |
| WO | 2011083460 A2 | 7/2011 | |
| WO | WO 2011083460 A2 * | 7/2011 | A61B 17/0218 |
| WO | 2011109792 A1 | 9/2011 | |

OTHER PUBLICATIONS

PCT International Search Report, mailed Dec. 5, 2013, pp. 1-12.
International Search Report for PCT/US2007/080516, mailed Aug. 14, 2008, pp. 1-3.
International Search Report and Written Opinion for PCT/US2012/049813, mailed Oct. 4, 2012, pp. 1-12.
International Search Report and Written Opinion for PCT/US2013/066192, mailed Dec. 4, 2013, pp. 1-12.
International Search Report and Written Opinion for PCT/US2013/066173, mailed Dec. 5, 2013, pp. 1-14.

* cited by examiner

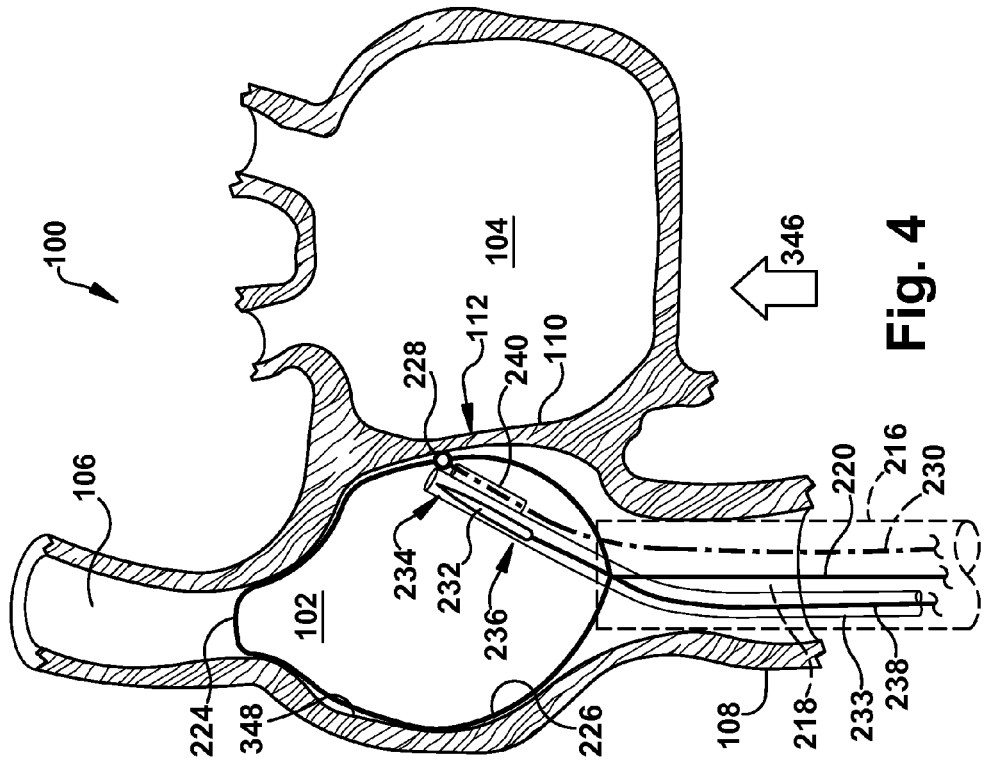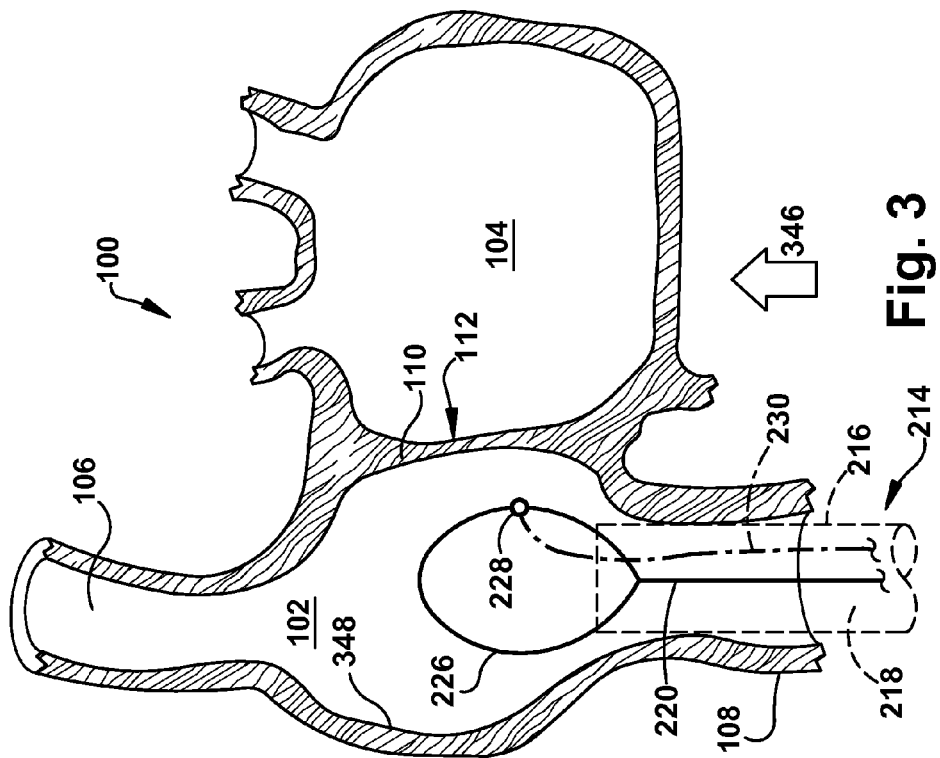

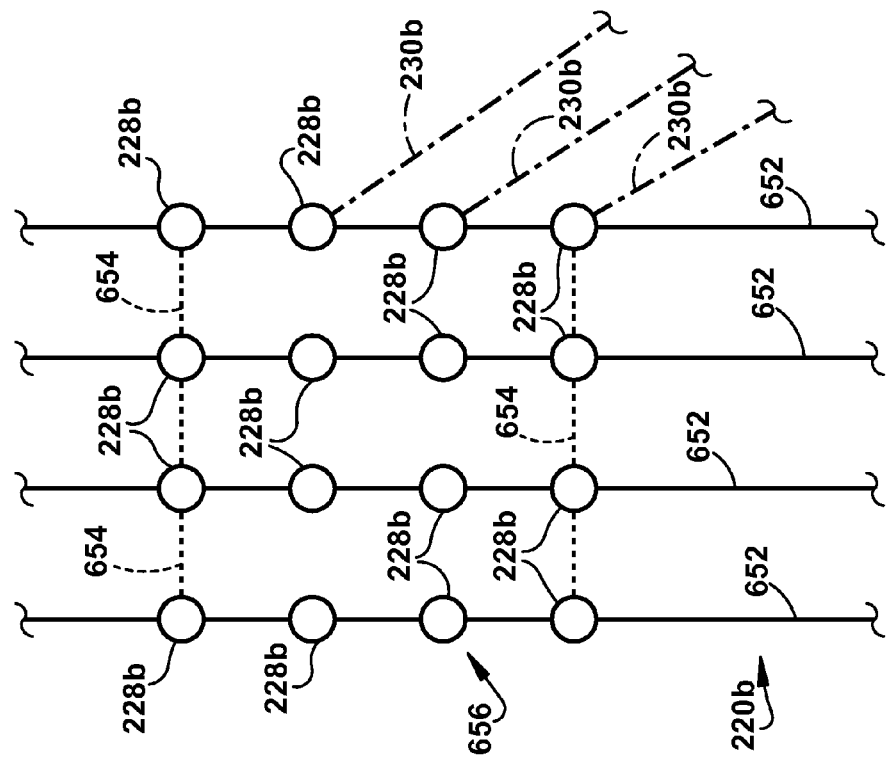
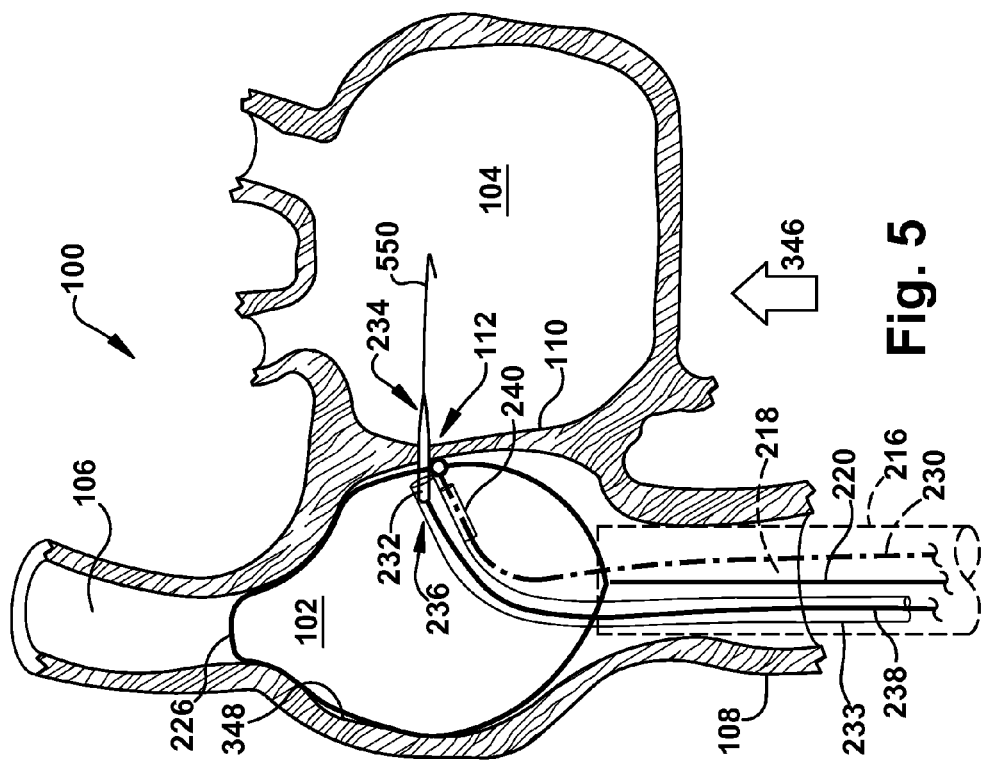
Fig. 6
Fig. 5

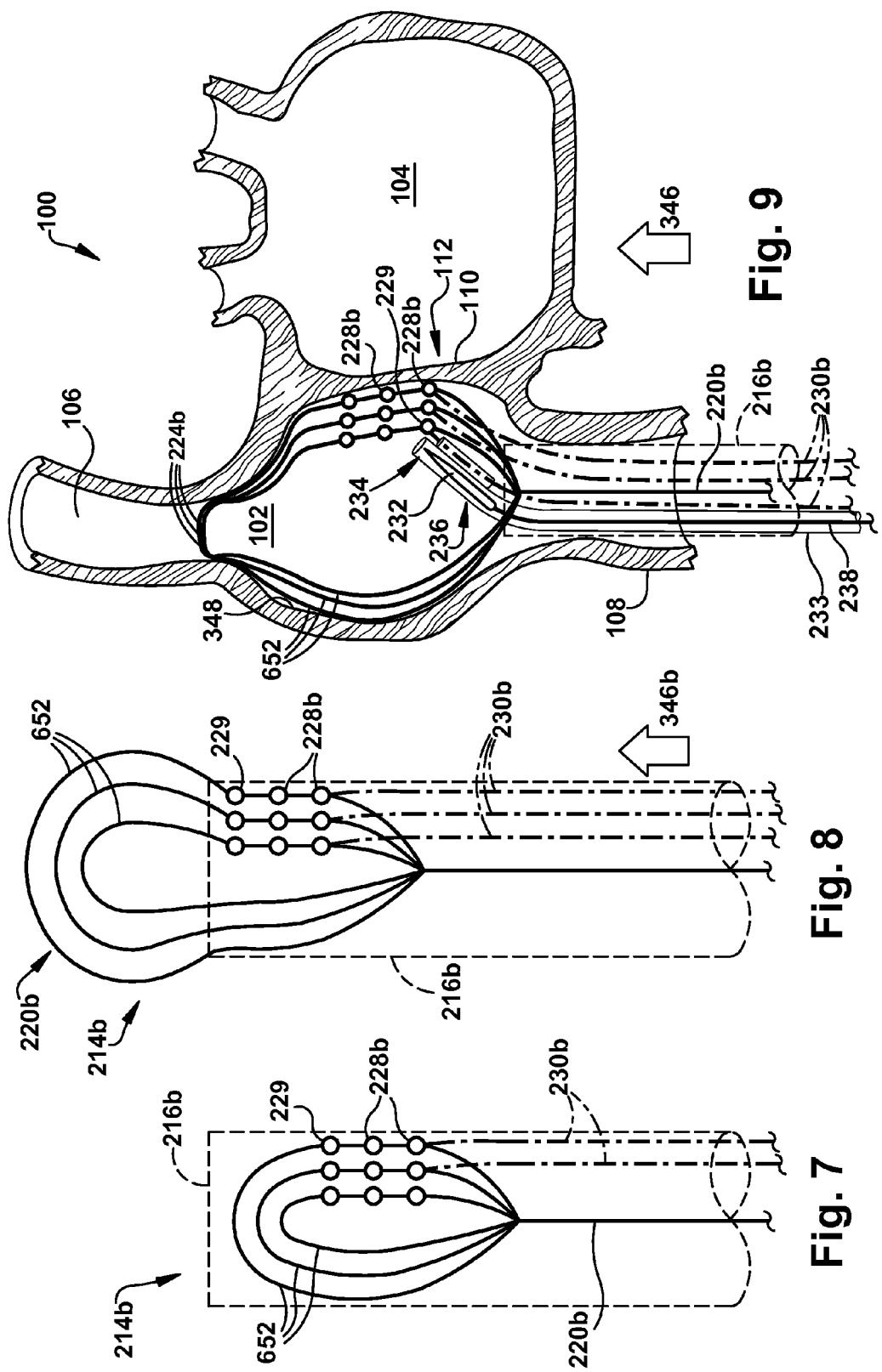

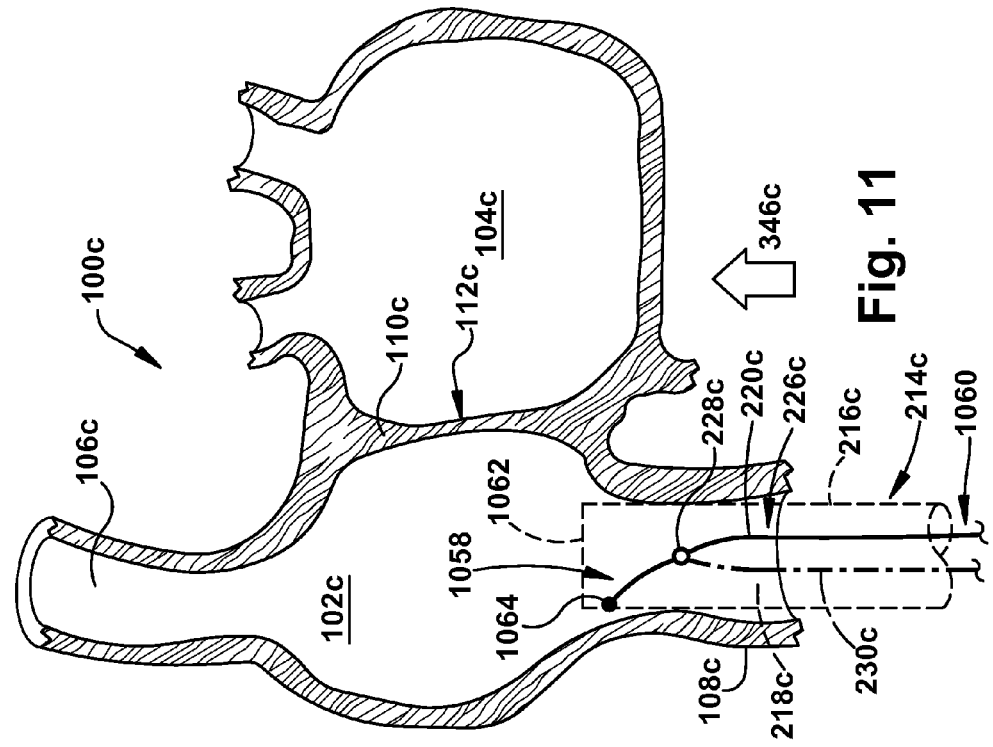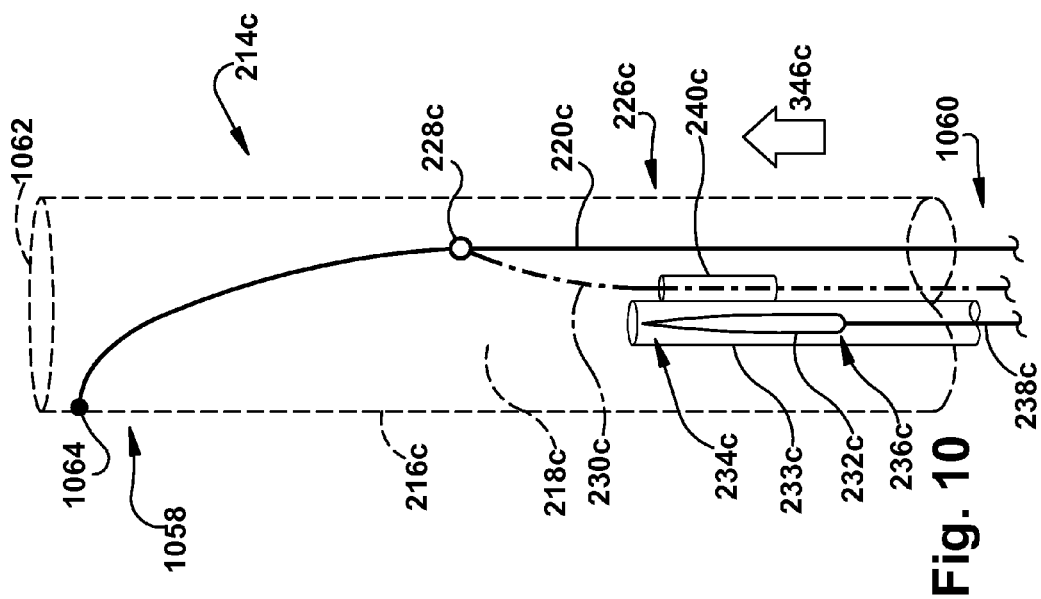

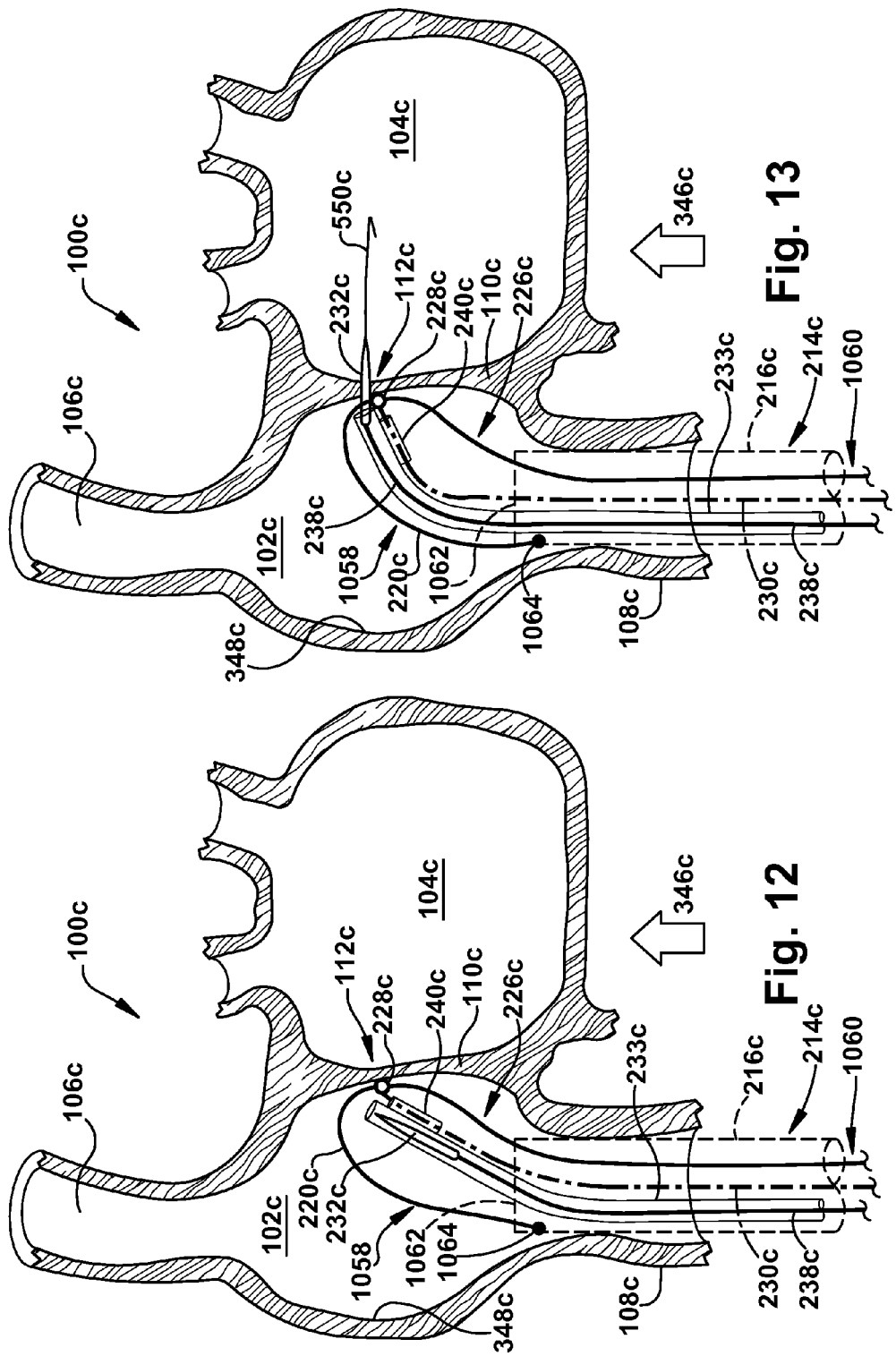

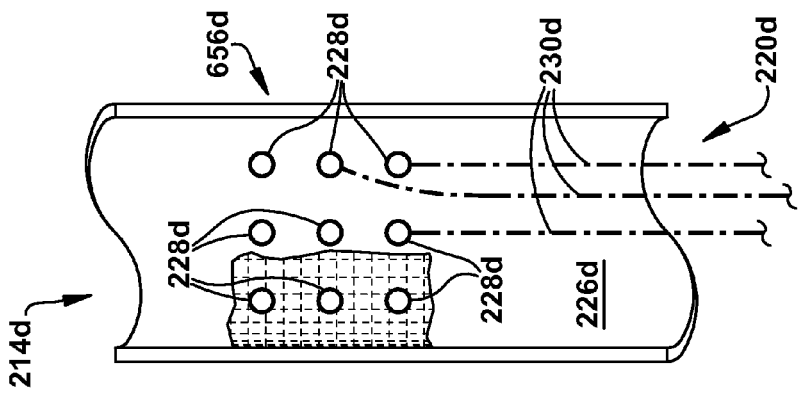
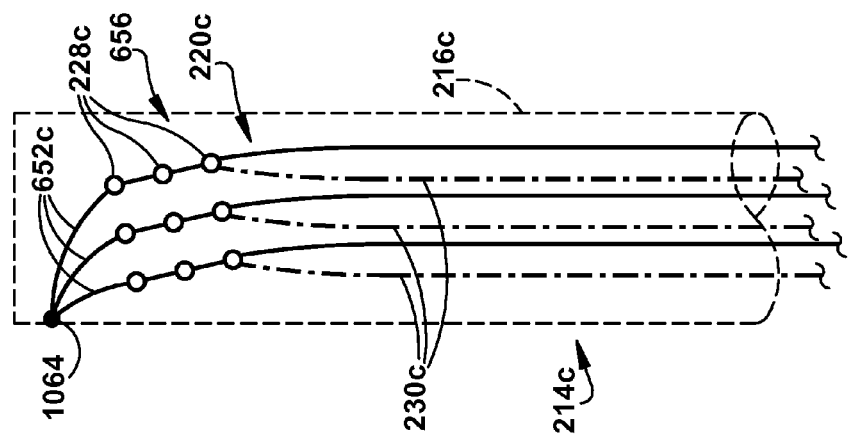

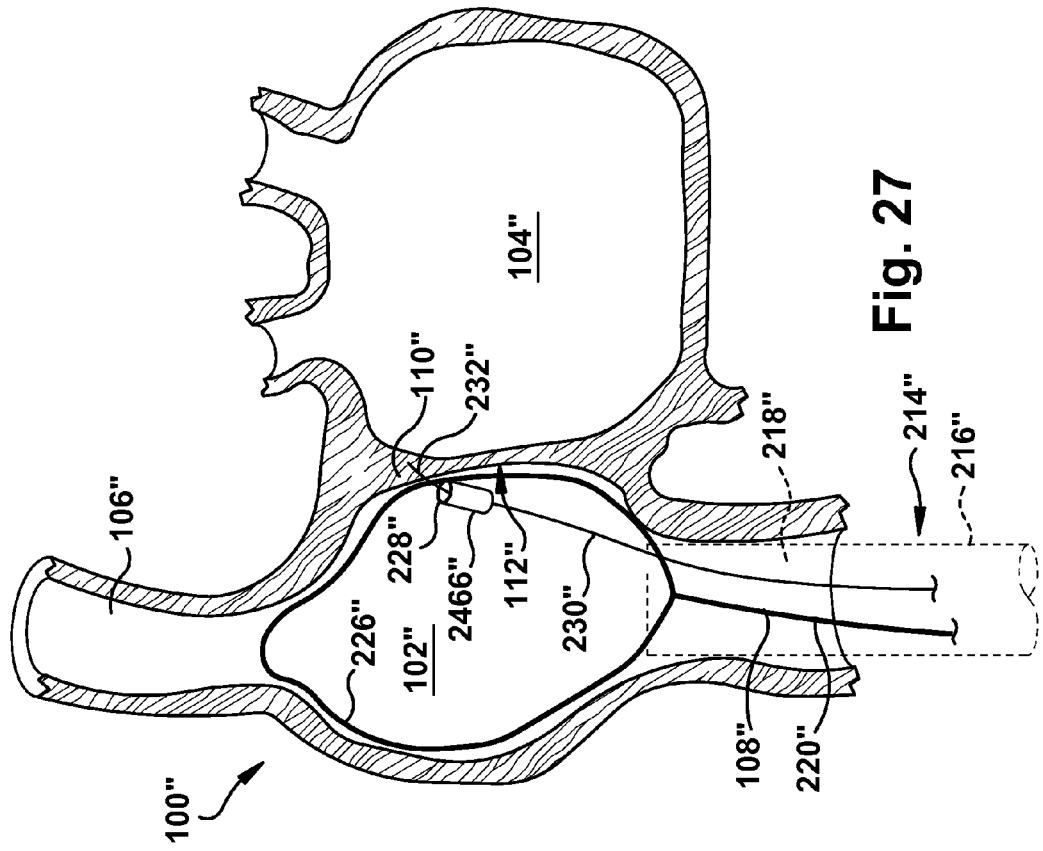
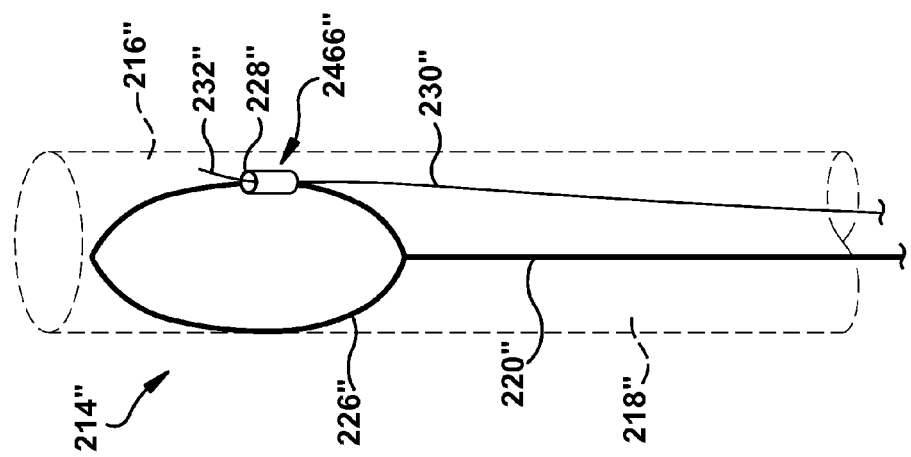

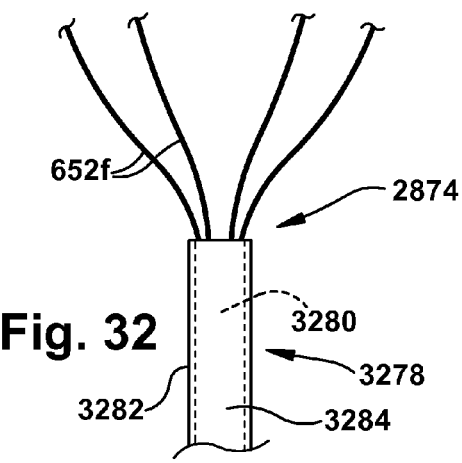
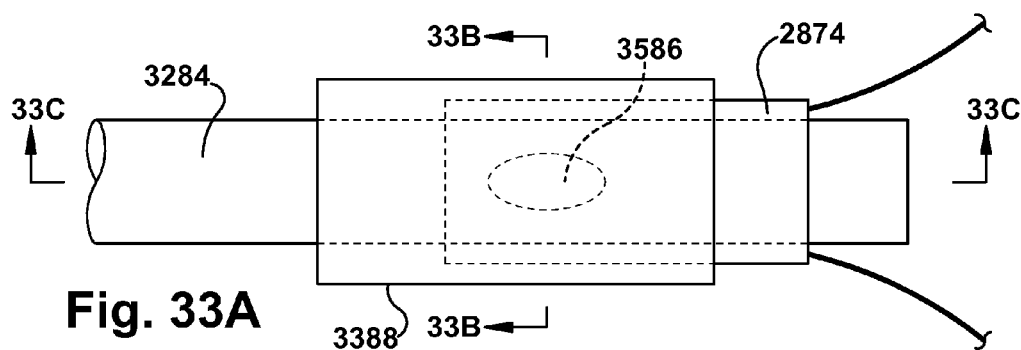
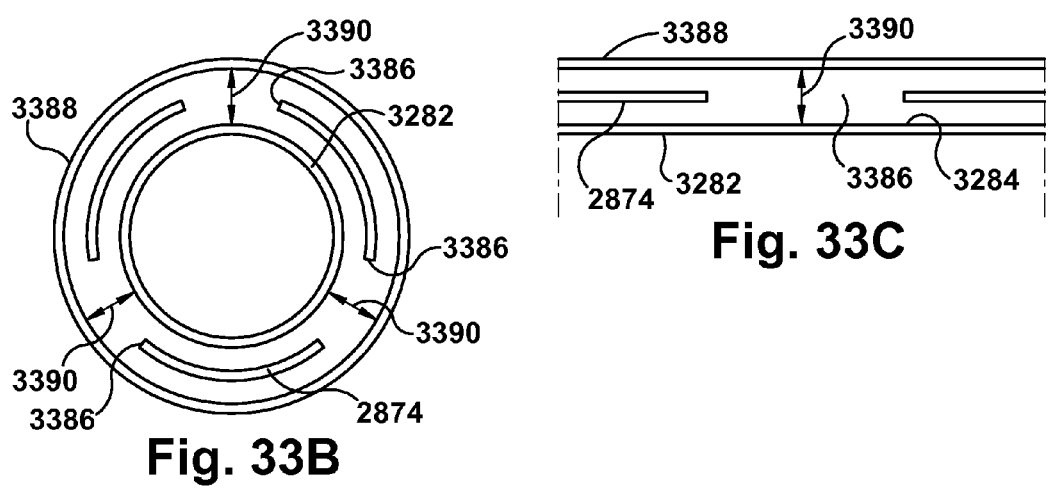

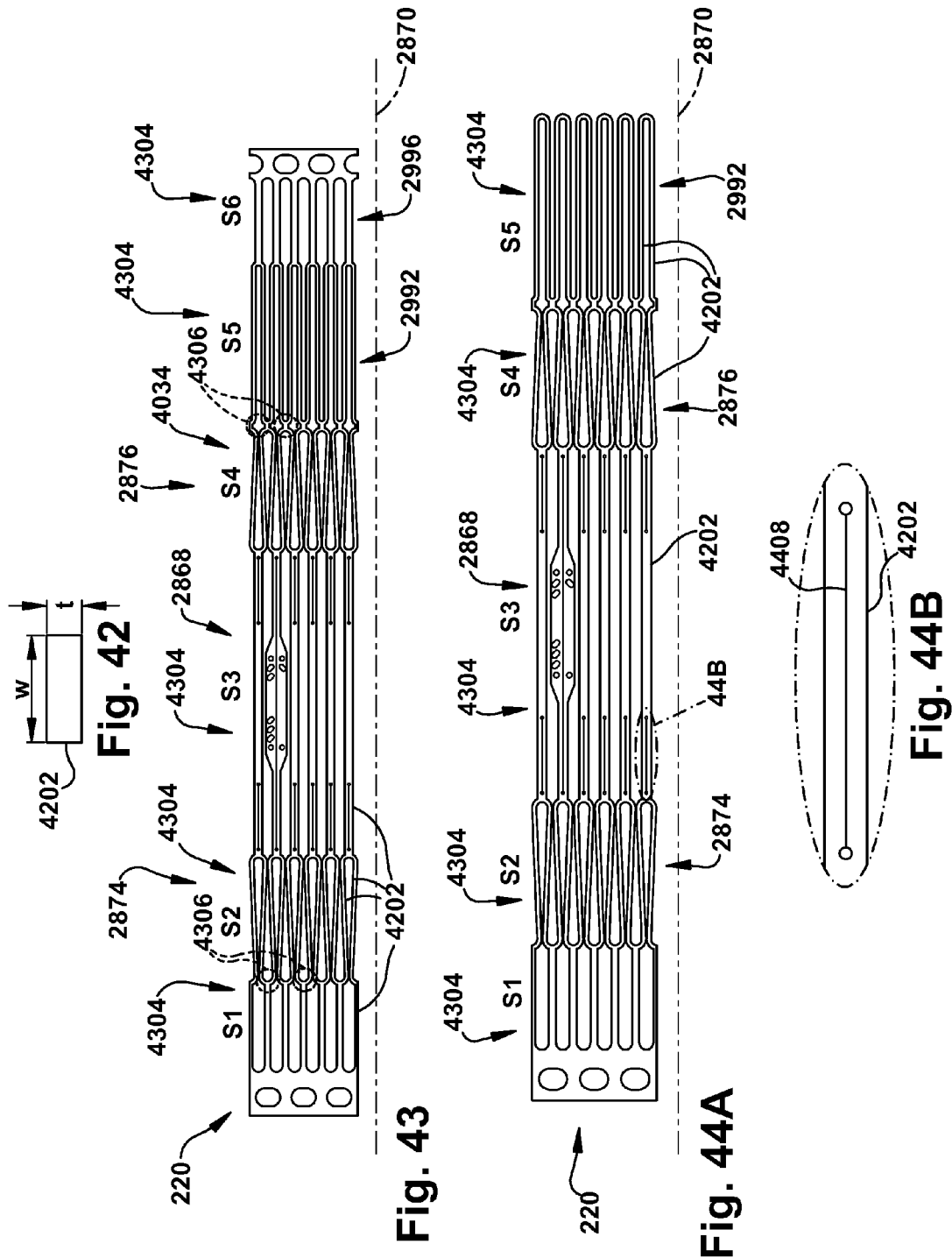

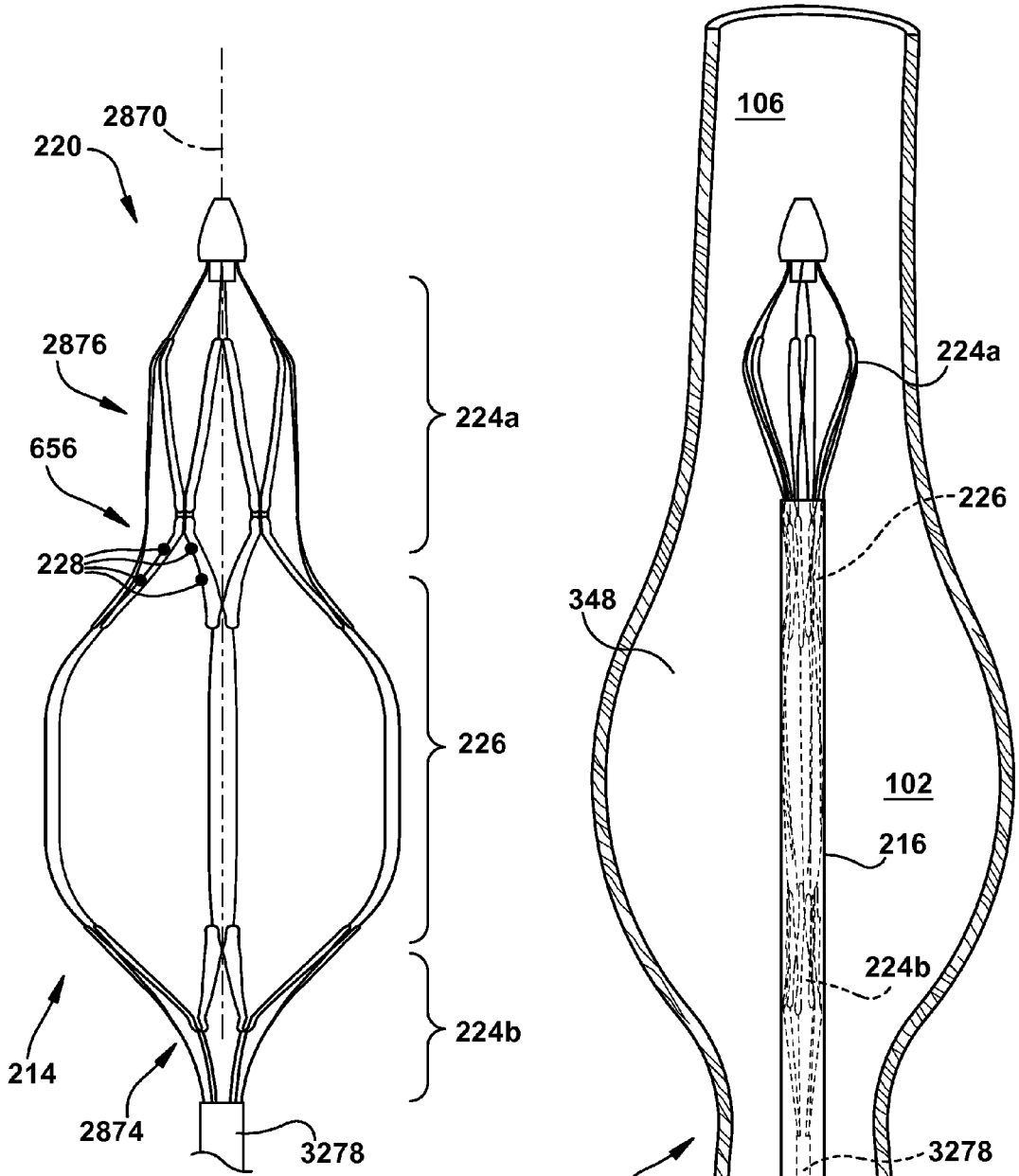

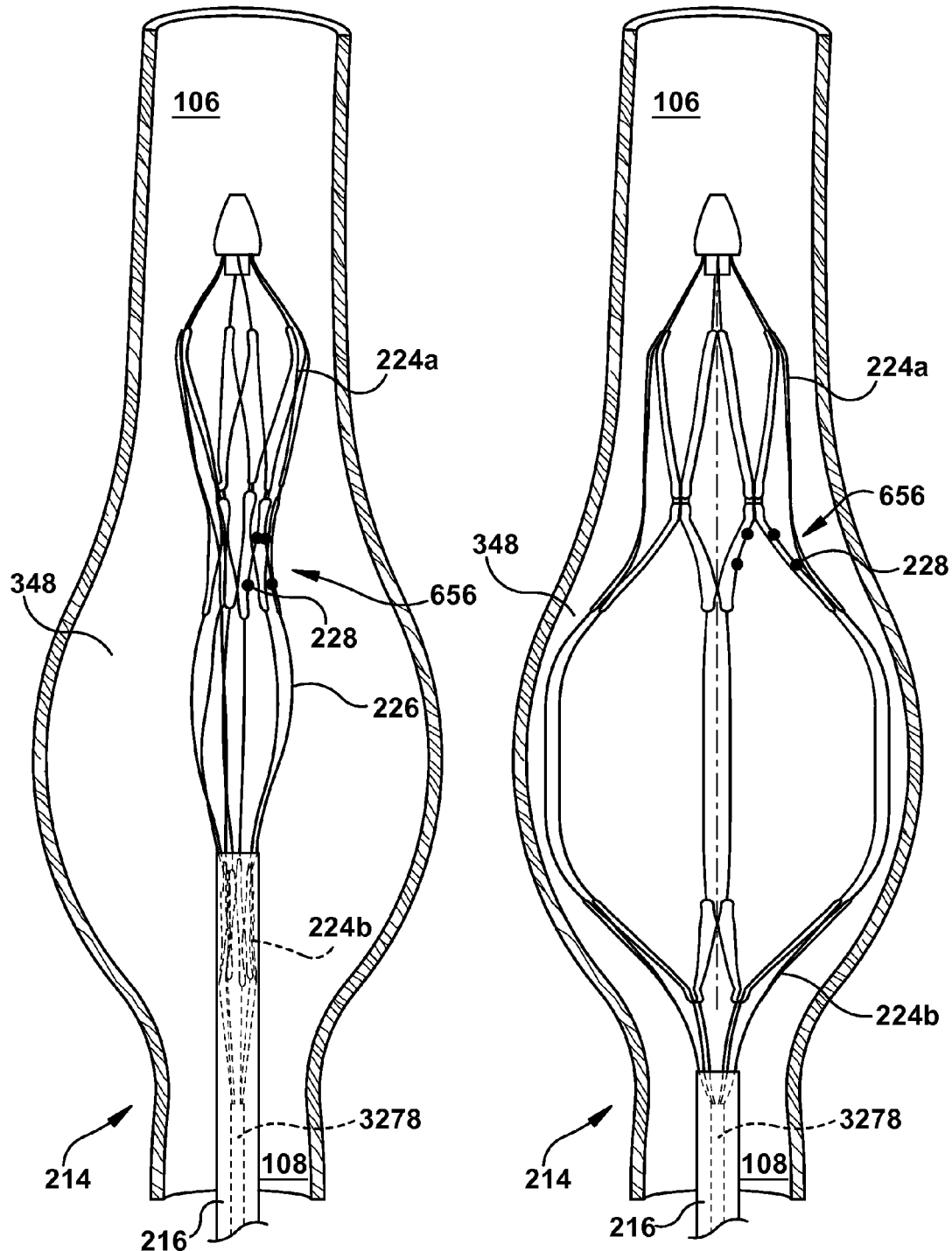

APPARATUS AND METHOD FOR TARGETING A BODY TISSUE

RELATED APPLICATIONS

This application is a continuation-in-part of U.S. patent application Ser. No. 13/206,639, filed 10 Aug. 2011 (now U.S. Pat. No. 8,694,077, issued 8 Apr. 2014), which is a continuation-in part of U.S. patent application Ser. No. 11/867,774, filed 5 Oct. 2007 (now U.S. Pat. No. 8,019,404, issued 13 Sep. 2011), which claims priority from U.S. Provisional Patent Application Ser. No. 60/850,147, filed 6 Oct. 2006, the subject matter of all of which is incorporated herein by reference in its entirety. This application also claims priority from U.S. Provisional Patent Application Ser. No. 61/716,690, filed 22 Oct. 2012; U.S. Provisional Patent Application Ser. No. 61/716,693, filed 22 Oct. 2012; U.S. Provisional Patent Application Ser. No. 61/716,699, filed 22 Oct. 2012; U.S. Provisional Patent Application Ser. No. 61/716,705, filed 22 Oct. 2012; U.S. Provisional Patent Application Ser. No. 61/716,716, filed 22 Oct. 2012; U.S. Provisional Patent Application Ser. No. 61/716,723, filed 22 Oct. 2012; U.S. Provisional Patent Application Ser. No. 61/716,651, filed 22 Oct. 2012; the subject matter of all of which is incorporated herein by reference in its entirety.

TECHNICAL FIELD

The present invention relates to an apparatus and method for targeting a body tissue and, more particularly, to an apparatus and method for targeting a desired target site on the body tissue.

BACKGROUND OF THE INVENTION

The typical human heart 100, a portion of which is shown in FIG. 1, includes a right ventricle, a right atrium 102, a left ventricle, and a left atrium 104. The right atrium 102 is in fluid communication with the superior vena cava 106 and the inferior vena cava 108. A tricuspid valve separates the right atrium 102 from the right ventricle. On the interatrial septum 110, which is the wall separating the right atrium 102 from the left atrium 104, is the fossa ovalis 112, a thin-walled, recessed area. In the heart of a fetus, the fossa ovalis 112 is open (patent foramen), permitting fetal blood to flow between the right and left atria 102 and 104, bypassing the fetal lungs in favor of the placental blood flow. In most individuals, this opening closes after birth.

A wide variety of diagnostic and therapeutic procedures have been developed in which a catheter is transluminally advanced into various chambers and across valves of the heart. The most difficult chamber of the heart to access with a catheter is the left atrium 104. Access to the left atrium 104 through the pulmonary artery is not possible. Approaches from the left ventricle are difficult, may cause arrhythmias, and may present difficulty in obtaining stable catheter positioning. Accordingly, the presently preferred method of accessing the left atrium 104 is through a transseptal approach, achieved by catheterization of the right atrium 102 with subsequent penetration of the interatrial septum 110. The reduced wall thickness and location of the fossa ovalis 112 make it a useful access point for a transseptal access puncture. The current methods of puncturing involve accessing the septum from the inferior vena cava 108. There is no device currently available that allows safe puncture from the superior vena cava 106.

A variety of risks are attendant to transseptal catheterization, in addition to the risks associated with normal heart catheterization. The primary additional risk is associated with inaccurate identification and localization of the interatrial septum 110 and the fossa ovalis 112 in particular. Improper placement of the catheter tip prior to the transseptal puncture presents the risk of puncture of tissue other than the interatrial septum 110, such as the aorta and/or the posterior wall of the right or left atrium 102 or 104. For this reason, catheterization is often accompanied by fluoroscopy or other visualizing techniques to assist in properly locating the catheter tip in relation to the septum 110.

The objectives of left atrial access can be either diagnostic or therapeutic. One diagnostic use is pressure measurement in the left atrium 104. In the setting of an obstructed mitral valve (mitral stenosis), left atrial access allows a determination of the pressure difference between the left atrium 104 and left ventricle. Left atrial access also allows entry into the left ventricle through the mitral valve. This is desirable when a mechanical aortic valve is in place. The advent of aortic valve replacement with mechanical artificial valves, and the increase in the aged population and growing longevity of that population subsequent to aortic valve replacement, brings a greater need to evaluate the late stage functionality of such artificial valves.

Diagnostic measurement of the left ventricular pressures is, therefore, desirable to allow evaluation of mechanical artificial aortic valves post-replacement. Crossing these mechanical artificial valves retrograde from the aorta may be nonoptimal; therefore, access to the left ventricle by an antegrade route using a transseptal puncture is generally the preferred approach. Once a catheter has been placed in the left atrium 104 using the transseptal approach, access to the left ventricle can be gained by advancing catheters across the mitral valve.

Many diagnostic indications exist for left atrial pressure measurements in addition to evaluating the functionality of artificial mitral valves. Other diagnostic indications for accessing the left ventricle via the antegrade transseptal approach include aortic stenosis, when a cardiologist is unable to pass a catheter retrograde into the left ventricle, and some disease states where the antegrade approach is considered preferable, such as subaortic obstruction.

Presently, the therapeutic objectives of left atrial access are primarily two-fold. The first is mitral valvuloplasty which represents an alternative to surgical procedures to relieve obstruction of the mitral valve. The second main therapeutic objective is for electrophysiological intervention in the left atrium 104 via catheter ablation. Catheter ablation involves the placement of energy, typically radio frequency (RF) from an electrode, through a catheter into various areas of the heart 100 to eradicate inappropriate electrical pathways affecting the heart function. When these locations are in the left atrium 104, the catheter through which the RF electrode is placed typically is itself placed into the left atrium 104 with transseptal catheterization. More recently, therapeutic treatment of the left atrial appendage to reduce the risk of embolic stroke has also been proposed.

In addition to the above, left atrium 104 access may be desirable for pulmonary vein isolation, atrial appendage closure, patent foramen ovalis closure, and aortic valve replacement or valvuloplasty. Despite clinical acceptance of a wide variety of procedures which require access to the left atrium 104, however, significant room for improvement remains in the actual access technique. For example, the step of locating an appropriate site on the interatrial septum 110, such as the fossa ovalis 112, is highly technique-dependent and can be inaccurate. Such inaccuracy may increase procedure time and/or create a risk that the needle will pierce a heart structure in an unnecessary and potentially undesirable location. Another problem is that the needle may slip while advancing toward the interatrial septum 110, resulting in an inadvertent puncture into surrounding structures within/defining the right atrium 102 before the needle even reaches the interatrial septum 110. This type of undesired puncture is particularly a risk when the left atrium 104 is large and causes the interatrial septum 110 to bulge into the right atrium 102.

In addition to the example of accessing the left atrium 104 through the interatrial septum 110, there are other occasions when it may be desirable to access a body cavity from a nearby hollow structure (vascular or otherwise) which is easier to access. Broadly, "inside-out" access to a number of different body structures could be useful in many different surgical situations. For example, a surgeon may wish to provide a cannula in the heart 100, place a conduit in an artery or vein, or to connect two adjacent body cavities by puncturing from one to the other and placing a conduit between the cavities.

Moreover, and more broadly, there are many reasons for a surgeon to desire precise location of a target site within the body, whether or not the target site is to be punctured.

SUMMARY OF THE INVENTION

In an embodiment of the present invention, an apparatus for targeting a desired target site on a body tissue comprising a wall of a first body cavity of a patient is described. A target catheter has a longitudinally extending target catheter lumen surrounded by a tubular target catheter wall having an outer surface. A framing member has a collapsed condition in which the framing member is adapted for insertion into the first body cavity and an expanded condition in which the framing member is adapted for placement within the first body cavity. The framing member, when deployed into the expanded condition, has a framing member body which includes a three-dimensionally bulbous portion defining a maximum body footprint in a lateral dimension and having longitudinally spaced proximal and distal body ends which are both longitudinally spaced from the maximum body footprint. A diameter of the bulbous portion is significantly smaller at the proximal and distal body ends than at the maximum body footprint. The proximal body end is attached to the outer surface of the target catheter wall. At least one target point is carried by the framing member and is adapted for placement adjacent the desired target site. At least one target pathway is attached to at least one target point. At least a portion of the target pathway extends through the target catheter lumen. The target pathway is substantially spaced apart from the framing member body. The framing member is comprised of a plurality of framing member beams. At least three framing member beam arrays of framing member beams are arranged in non-overlapping longitudinal sequence to form at least a portion of the framing member. The framing member beams that make up the framing member substantially each have a width-to-thickness fractional ratio in the range of 0.6-3.0.

In an embodiment of the present invention, an apparatus for targeting a desired target site on a body tissue that separates a first body cavity from a second body cavity of a patient is described. A catheter has a longitudinally extending catheter lumen and is adapted to provide access to the first body cavity. A framing member has a collapsed condition in which the framing member is adapted for insertion into the first body cavity through the catheter lumen and an expanded condition in which the framing member is adapted for placement within the first body cavity. The framing member has a framing member body. At least one target point is carried by the framing member and is adapted for placement adjacent the desired target site. At least one target pathway is attached to at least one target point. At least a portion of the target pathway extends through the catheter lumen. The target pathway is substantially spaced apart from the body.

BRIEF DESCRIPTION OF THE DRAWINGS

For a better understanding of the invention, reference may be made to the accompanying drawings, in which:

FIG. 3 is a side view of the embodiment of FIG. 2 in a second condition within a heart;

FIG. 4 is a side view of the embodiment of FIG. 2 in a third condition within a heart;

FIG. 5 is a side view of the embodiment of FIG. 2 in the third condition within a heart;

FIG. 6 is a partial side view of a second embodiment of the present invention;

FIG. 7 is a side view of the second embodiment of FIG. 6 in a first condition;

FIG. 8 is a side view of the second embodiment of FIG. 6 in a second condition;

FIG. 9 is a side view of the second embodiment of FIG. 6 in a third condition;

FIG. 10 is a side view of a third embodiment of the present invention in a first condition;

FIG. 11 is a side view of the third embodiment of FIG. 10 in the first condition within a heart;

FIG. 12 is a side view of the third embodiment of FIG. 10 in a second condition within a heart;

FIG. 13 is a side view of the third embodiment of FIG. 10 in a third condition within a heart;

FIG. 14 is a side view of an alternate configuration of the third embodiment of the present invention in a first condition;

FIG. 15 is a partial side view of a fourth embodiment of the present invention;

FIG. 26 is a partial side view of an eighth embodiment of the present invention;

FIG. 27 is a side view of the eighth embodiment of FIG. 26 in a second condition within a heart;

FIG. 32 is a schematic partial side view of the ninth embodiment of FIG. 28;

FIG. 33A is a schematic partial detail view of the ninth embodiment of FIG. 28;

FIG. 33B is a cross-sectional view taken along line B-B of FIG. 33A;

FIG. 33C is a cross-sectional view taken along line C-C of FIG. 33A;

FIG. 42 is a cross-sectional detail of a component of the present invention;

FIG. 43 is a schematic cut pattern view of the ninth embodiment of FIG. 28;

FIG. 44A is a schematic cut pattern view of the tenth embodiment of FIG. 36;

FIG. 44B is a detail taken at circle B of FIG. 44A;

FIG. 48 schematically depicts an example configuration of a component of the present invention; and FIGS. 49A-49C schematically depict a sequence of operation of the component of FIG. 48.

DESCRIPTION OF EMBODIMENTS

Figure 2:
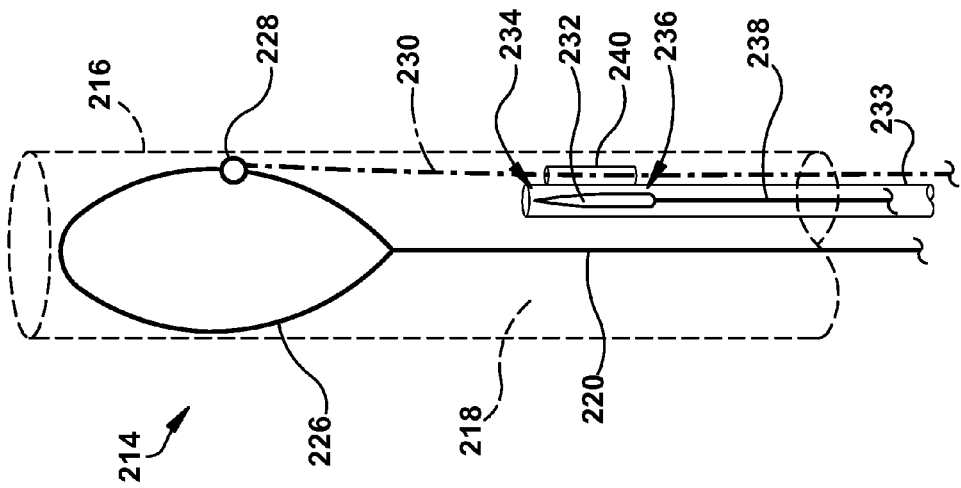
FIG. 2 is a side view of a first embodiment of the present invention in a first condition.
Figure 1:
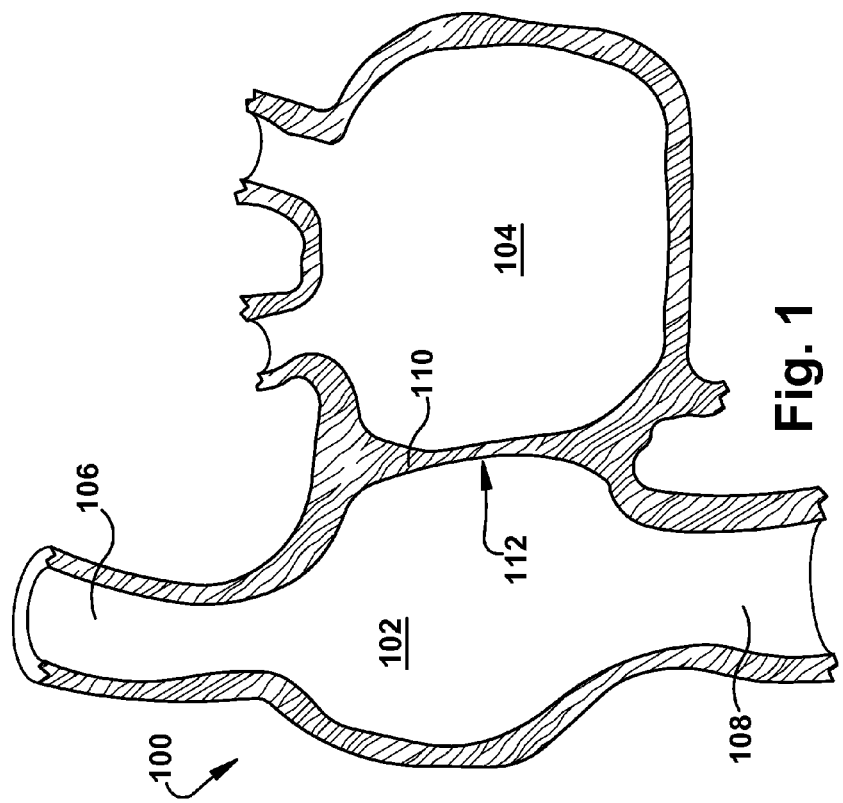
FIG. 1 is a schematic cross-sectional view of a heart, showing a first example use environment.

In accordance with the present invention, FIG. 2 depicts a first embodiment of an apparatus 214 for targeting a desired target site on a body tissue. Throughout this description, the desired target site is presumed to be an interatrial septum 110 that separates a right atrium 102 from a left atrium 104 of a heart 100, but (as discussed below) may be any body tissue of a patient. Moreover, this description presumes that the desired target site is being targeted for puncture. However, the apparatus 214 could be useful in precisely locating a desired target site which is being targeted for any reason, without limitation. For example, it may be useful to target a desired target site without necessarily puncturing or otherwise altering the target site when repairing an atrial septum defect (such as a patent foramen ovalis), for dissection/location/alignment of any body structure, when repairing a perivalvular leak, for pinpointing a small branch from a blood vessel (i.e., targeting a void in a body tissue rather than a point on the body tissue), or the like. One of ordinary skill in the art could readily use the apparatus 214 for any application in which a target site is located for any reason or as a part of any procedure. For example, a target site could be helpful in a gastrointestinal or genitourinary tract access procedure, to put in a shunt (e.g., for a neurological procedure), or for any other desirable procedure. However, for clarity, the below description presumes that the targeting is being accomplished preparatory to a puncture procedure.

The apparatus 214 includes a catheter 216 (shown in dashed line in FIG. 2) having a longitudinally extending catheter lumen 218 and adapted to provide access to the right atrium 102 through a blood vessel, such as the superior or inferior vena cava 106 or 108. For ease of description, the desired target site will be presumed to be the fossa ovalis 112 when the desired target site is located on an interatrial septum 110. Any desired target site, however, may be targeted by the apparatus 214.

A framing member 220 has a collapsed condition (shown as the first condition of FIG. 2) in which the framing member is adapted for insertion into the blood vessel through the catheter lumen 218. The framing member 220 shown in FIG. 2 is a loop of thin, flexible wire having a framing member body 226 and may be made of any suitable material such as, for example, a woven, drawn, or otherwise formed strand of Nitinol, stainless steel, nylon, plastic, or any other material as desired. The framing member 220 may be radiopaque, in whole or part, to facilitate positioning within the right atrium 102 as desired. The framing member 220 also has an expanded condition (shown as the second and third conditions in FIGS. 3 and 4) in which the framing member is adapted for placement within the right atrium 102. In the first embodiment, the framing member 220 is self-expanding and should be designed to have a resting configuration compatible with the right atrium 102. The framing member 220 may include a shaped feature, such as the protrusion 224, which is adapted to enter the superior vena cava 106 or another structure and facilitate rotational positioning of the framing member 220 within the right atrium 102. For example, the framing member 220 could be made from a memory alloy having the resting configuration shown in FIG. 4 but selectively compressible into the catheter 216 for delivery to the right atrium 102.

The framing member 220 carries at least one target point 228 (one shown in FIGS. 2-5). The target point 228 is adapted for placement adjacent the interatrial septum 110 to indicate the desired target site. The target point 228 may have an associated radiopaque marker (not shown) or otherwise be visible to an external imaging system or other remote detection system (not shown) when located within the patient's heart 100. The target point 228 may be affixed, as shown in FIG. 2, to the framing member body 226. It is contemplated that the target point 228 may be affixed in either a movable or nonmovable manner with respect to the framing member 220.

Each target point 228 may be attached to a target pathway, such as, in the embodiments of FIGS. 2-23, a target wire 230 (shown in dash-dot line in the Figures). As shown in the Figures, the target pathway includes one end (here, the end attached to the target point 228) which is touching or directly adjacent to the framing member 220. The remainder of the target pathway is substantially spaced apart from the framing member body 226. In other words, the target pathway and the framing member body 226 are substantially separate structures, in the example embodiments depicted in the Figures, which "meet" at the target point(s) 228. While it would be possible for the target pathway to be coaxial with, and/or coextend with, at least a portion of the framing member 220, this situation is not shown in the Figures and will not be described further herein. (The relatively small portion of the target pathway which is attached to the target point 228 may be located adjacent or even in contact with the framing member body 226 without destroying this "substantial spacing apart", however.) Optionally, at least a portion of the target pathway may extend through the catheter lumen 218.

The target wire 230 extends through the catheter lumen 218 between an external power source (not shown) and the target point 228. The target wire 230 may selectively provide at least one of an electrical and a mechanical signal to the target point 228 to indicate a position of the target point within the heart 100 in an actively powered manner. Such indication may be made in a visual manner, and/or may be made in cooperation with an external imaging or other remote detection system.

For example, the target wire 230 could transmit a mechanical vibration to the target point 228 to cause the target point to move slightly. The external imaging system would detect such a motion and responsively indicate the location of the target point in relation to the target site on the interatrial septum 110 or another heart 100 structure. Similarly, the target wire 230 could carry an electrical current and cause the target point 228 to emit an electromagnetic signal having certain predetermined signal characteristics. The external imaging system then would detect the emitted signal and responsively indicate the location of the target point 228 within the heart 100. It is contemplated, however, that the target point 228 may also or instead be passively detected—for example, an external or internal imaging or other detection system could "view" or otherwise detect a position of the target point 228 relative to the body tissue (e.g., interatrial septum 110) and the user could then proceed accordingly without a signal being provided to the target point.

A puncture needle 232 is provided. The puncture needle 232 is adapted for insertion through the catheter lumen 218 and into the right atrium 102. Optionally, and as shown in the drawings, the puncture needle 232 may be contained within a needle catheter 233. The puncture needle 232 has longitudinally spaced first and second needle ends 234 and 236, respectively, with the first needle end 234 being operative to puncture the interatrial septum 110 at the desired target site, which is optionally the fossa ovalis 112, as discussed herein. The second needle end 236 may be attached to a needle wire 238, which allows the user to remotely control the motion of the puncture needle 232 inside the needle catheter 233. The puncture needle 232 could have a hollow bore (not shown), through which a guidewire could be extended, as discussed below.

Optionally, the needle catheter 233 may be connected to the target wire 230 in a "monorail"-like manner, using a needle coupler 240. This connection allows the target wire 230 to guide the puncture needle 232 to the desired target site quickly and efficiently. A needle coupler 240 could also be directly connected to the puncture needle 232 and/or the needle wire 238, to allow "monorail"-type guidance of the puncture needle without an intervening needle catheter 233.

When a needle coupler 240 or other system/structure is used to guide the puncture needle 232, the target point 228 may need to be calibrated or otherwise adjusted with respect to the desired target site. One of ordinary skill in the art can readily compensate for any offset distance between the target point 228 and the actual position of the first needle end 234 which may be caused by the needle coupler 240, needle catheter 233, or other guidance structure. While often the target point 228 may be superimposed—from the viewpoint of the target pathway—upon the desired target site, it is also contemplated that the target point 228 may have a desired offset distance and/or direction from the desired target site to allow for desired precision in guiding the puncture needle 232 to the desired target site. In the former arrangement, the target point 228 may block access to the desired target site in a way that could be alleviated via the latter arrangement for particular applications of the present invention.

In most embodiments of the present invention, it is contemplated that the target point 228 will be located adjacent to, or directly upon, the desired target site. It is also contemplated, though, that the target point 228 may be located upon the framing member 220 at a location substantially spaced from the desired target point (e.g., a location opposite the desired target point such as on a diametrically opposed portion of a body lumen therefrom). One of ordinary skill in the art will realize that such remote location may inherently reduce the precision of indication of the desired target site, however, in certain applications of the present invention.

The operation of the first embodiment of the present invention is depicted in the sequence of FIGS. 2-5. As discussed above, the target wire 230 and needle coupler 240 are optional, but are shown in FIGS. 2-5 for clarity of description of the first embodiment of the present invention.

First, the catheter 216 is inserted into the patient's vascular system and guided through the vascular system into or near the right atrium 102 of the heart 100, with the catheter 216 shown in FIG. 3 as entering the right atrium 102 through the inferior vena cava 108. However, the catheter 216 could instead enter the right atrium 102 through the superior vena cava 106 or in another manner. Regardless of the manner and location in which the catheter 216 is guided into position within the right atrium 102, the framing member 220 may be inserted, in the first (collapsed) condition, into the right atrium through the catheter lumen 218. The framing member 220, in the collapsed condition, need not protrude from the catheter lumen 218 within the right atrium 102, but may do so if desired.

Optionally, the catheter 216 may be inserted a relatively deep distance into the right atrium 102 or through the right atrium and into the superior vena cava 106, and the framing member 220 may be maintained at that insertion depth within the right atrium or superior vena cava. The catheter 216 may then be at least partially retracted from the right atrium 102, thus moving relative to the framing member 220 and unsheathing the framing member. This technique may be useful when a protrusion 224 or other nonuniformity of the framing member 220 is provided to mate with the superior vena cava 106. Otherwise, the catheter 216 may be maintained at a relatively shallow insertion distance into the right atrium 102, as shown in FIGS. 3-5, and the framing member 220 may then be moved into the right atrium, in an advancement direction 346, to emerge from the catheter.

The framing member 220 is then expanded into the second (expanded) condition within the right atrium 102, as shown in the sequence of FIGS. 3-4. This expansion may be done in whole or in part, and as quickly as desired, depending upon the particular application of the apparatus 214. As mentioned above, the framing member 220 of the first embodiment is self-expanding into the expanded condition and may include a protrusion 233 for locating the framing member within the right atrium 102.

As the framing member body 226 is brought into position within the right atrium 102 as desired, the framing member 220 may be manipulated to position the target point 228 adjacent the interatrial septum 110. Optionally, the target point 228 may contact the interatrial septum 110. The location of the target point 228 on the framing member 220 should be predetermined to facilitate positioning adjacent the interatrial septum 110 as desired.

Optionally, the target point 228 may be slidably fastened to, or otherwise movable with respect to, the framing member 220. In such case, the target wire 230, when present, may assist in moving the target point 228 along the framing member 220 and into the desired position adjacent the interatrial septum 110.

When the framing member 220 has been expanded into the right atrium 102 and arranged as desired to bring the target point 228 into the desired position adjacent the interatrial septum 110, at least a portion of the framing member body 226 may lie in contact with the interatrial septum. That is, the framing member 220 may contact one or more locations on, or areas of, the interatrial septum 110.

The right atrium 102 includes an internal right atrium surface 348, of which the interatrial septum 110 forms a portion. The framing member 220 may exert a positive pressure on any areas of the internal right atrium surface 348 when in the expanded condition. The framing member 220 is optionally designed to brace against areas of the internal right atrium surface 348 remote from the interatrial septum 110 in order to maintain contact between the target point 228 and the interatrial septum. For instance, the framing member 220 may be designed to be slightly larger than the internal right atrium surface 348 in one or more dimensions when in the expanded condition, in order to exert a positive pressure needed to maintain the target point 228 in a desired position.

In order to confirm that the target point 228 is located adjacent the interatrial septum 110 as desired before the surgery proceeds, the position of the target point 228 may be viewed within the right atrium 102 using an external imaging or other detection system (not shown). The position may be established and "viewed" (whether or not actual optical viewing takes place) passively when the target point 228 includes a radiopaque or other marker.

Alternately, an active determination of the position of the target point 228 may be made, such as by selectively providing at least one of an electrical and a mechanical signal through the target wire 230 to the target point 228. An external imaging or other remote detection system may be used to sense a position-indication motion or signal produced by the target point 228 responsive to the electrical and/or mechanical signal. The user can then review the output of the remote detection system to determine the location of the target point 228 within the right atrium 102. This position-checking process may be repeated as needed at any suitable time throughout the targeting procedure.

A puncture needle 232 may be inserted into the catheter 216, through use of a needle catheter 233, at any suitable time before or during the septal puncture procedure. The needle catheter 233 may be coupled to the target wire 230, when present, or may be guided independently, as previously discussed. For ease of description below, it is presumed that a needle coupler 240, which may be a loop of suture thread, a monorail catheter coupler, or have any other suitable structure, attaches the needle catheter 233 to the target wire 230.

The needle catheter 233 is passed through the catheter lumen 218 into the right atrium 102 and is guided to the target point 228, advancing in the advancement direction 346. As shown in FIGS. 4 and 5, this guidance may occur along the target wire 230. When the needle catheter 233 reaches the interatrial septum 110 at or adjacent the desired target site, the puncture needle 232 is moved in the advancement direction 346 relative to the needle catheter 233. This motion should be sufficient for the puncture needle 232 to puncture the interatrial septum at the desired target site and allow the first needle end to enter the left atrium 104.

Once the puncture needle 232 has passed at least partially through the interatrial septum 110, the left atrium 104 may be accessed through the puncture at the target site in any suitable manner. For example, a guidewire 550 could be advanced through the needle catheter 233, optionally following the needle wire 238, and into the left atrium 104. As shown in FIG. 5, the guidewire 550, when present, may be inserted through a hollow bore (not shown) of the puncture needle 232 and into the left atrium 104. Once the guidewire 550 is in place, the puncture needle 232 and needle wire 238, and optionally the needle catheter 233, can be removed from the catheter 216. With the guidewire 550 in place, the left atrium 104 can be accessed as desired in a known manner as the surgical procedure progresses.

The apparatus 214, or portions thereof, may be removed from the right atrium 102 if desired, by reversing all or part of the above process. The guidewire 550, particularly, may be left in place after removal of other portions of the apparatus 214 to facilitate access to the left atrium 104. Optionally, the catheter 216 may remain in position after the puncture is made to continue right and left atrium 102 and 104 access as the surgery progresses, with the framing member(s) 220, target wire(s) 230, and/or puncture needle 232 being retracted through the catheter 216 and removed from the patient. The catheter 216, guidewire 550, and any other portions of the apparatus 214 which were left in place within the patient may be removed as the surgery concludes.

FIGS. 6-9 illustrate a second embodiment of an apparatus 214b. The apparatus 214b of FIGS. 6-9 is similar to the apparatus of FIGS. 2-5 and therefore, structures of FIGS. 6-9 that are the same as or similar to those described with reference to FIGS. 2-5 have the same reference numbers with the addition of the suffix "b". Description of common elements and operation similar to those in the previously described first embodiment will not be repeated with respect to the second embodiment.

The framing member 220b of the second embodiment is made up of a plurality of framing strands 652, with each framing strand 652 being similar to the framing member 220 of the first embodiment. The framing strands 652 are optionally attached together with framing cross members 654, shown in dashed line in FIG. 6. Whether or not framing cross members 654 are provided, the framing member 220b carries a plurality of target points 229 forming a target array, shown in FIGS. 6-9 as a target grid 656. The target grid 656 is shown in the Figures as being a regular rectilinear array. However, the target array, like all structures described herein, could have any suitable regular or irregular two- or three-dimensional shape, profile, or configuration. Each target point 229 may have a corresponding target wire 230b, most of which are omitted throughout the Figures in all embodiments for clarity. Those target wires 230b shown in the Figures as examples have no particular significance distinguishing them from the omitted target wires 230*b*.

The framing member 220*b* of the second embodiment is expanded into the expanded condition much like the framing member 220 of the first embodiment, as shown in the sequence of FIGS. 7-9. The catheter 216*b* and framing member 220*b* are moved relatively, such as by movement of the framing member in the advancement direction 346*b*. The framing member 220*b* of the second embodiment is self-expanding, as shown in the sequence of FIGS. 7-9, and is designed to occupy at least a portion of the right atrium 102, as with the framing member 220 of the first embodiment.

The framing member 220*b* is used to help position at least a portion of the target grid 656 adjacent the interatrial septum 110*b*. The position of the target grid 656 within the right atrium 102*b* is then determined, either actively or passively. Optionally, this is done by viewing the target grid 656 using an external imaging or other remote detection system (not shown).

For example, a target wire 230*b* corresponding to a test target point 229, for example, the top right target point 229 (as viewed in FIG. 7), may be used to selectively provide at least one of a mechanical and an electrical signal to that test target point 229. The resultant signal produced by the test target point 229 may then be viewed with the external imaging or other remote detection system to determine the position of that test target point 229 within the right atrium 102*b*. This process can be repeated as needed until the position of each target point 229 is known, either directly or through extrapolation from other, directly detected, target points 229.

Once the position of the target grid 656 is known, a closest target point 229 to a desired target site, or another target point 229 having a desired relationship with the desired target site, may be chosen. For a puncture procedure in which a target wire 230*b* is used to guide the needle catheter 233*b*, the needle coupler 240*b* is attached to the target wire 230*b* corresponding to that selected target point 229. Whether or not the needle catheter 233*b* is guided by the target wire 230*b*, the puncture needle 232*b* can be guided to the selected target point 229 and puncture the interatrial septum 110*b* at the desired target site in much the same manner as described above.

FIGS. 10-13 illustrate a third embodiment of an apparatus 214*c*. The apparatus 214*c* of FIGS. 10-13 is similar to the apparatus of FIGS. 2-5 and therefore, structures of FIGS. 10-13 that are the same as or similar to those described with reference to FIGS. 2-5 have the same reference numbers with the addition of the suffix "c". Description of common elements and operation similar to those in the previously described embodiments will not be repeated with respect to the third embodiment.

In the third embodiment of FIG. 10, the framing member 220*c* may be an elongated framing member having longitudinally spaced first and second framing member ends 1058 and 1060, respectively, separated by an intermediate framing member body 226*c*. The catheter 216*c* has a catheter outlet end 1062 in fluid communication with the right atrium 102*c*. The framing member 220*c* depicted in FIGS. 10-13 is a fairly stiff but elastically deformable wire, with the first framing member end 1058 anchored to the catheter 216*d* at an anchor point 1064 adjacent the catheter outlet end 1062. The framing member 220*c* does not need to be self-expanding in the third embodiment of the present invention because the expansion may be effected by outside forces acting on the framing member 220*c*.

The anchoring attachment may be static, such as a weld, or dynamic, such as a pivoting joint. The anchor point 1064 may be at any location on the inside or outside of the catheter 216*c* and may be readily chosen for a particular application of the apparatus 214*c* by one of ordinary skill in the art. The anchor point and/or type may be chosen to steer the framing member body 226*c* to expand asymmetrically, as shown in FIGS. 12-13.

Deployment of the apparatus 214*c* is shown in the sequence of FIGS. 11-13. To expand the framing member 220*c* into the second, expanded condition within the right atrium 102*c*, the second framing member end 1060 is advanced toward the right atrium, as indicated by the advancement direction arrow 346*c*. Since the first framing member end 1058 is affixed to the catheter 216*c* at the anchor point 1064, advancement of the second framing member end 1060 will cause at least a portion of the framing member body 226*c* to bow out into the right atrium 102*c*, as shown in FIGS. 12 and 13.

Once the framing member 220*c* has reached the expanded condition (shown as the second condition in FIG. 12), the position of the target point 228*c* can be checked and adjusted as needed, optionally with the assistance of a radiopaque marker or of a target wire 230*c* and remote detection system, as described above. The needle catheter 233*c*, when used in a puncture procedure, may be guided to the desired target site in any suitable manner, such as along the target wire 230*c* using a needle coupler 240*c*, as depicted in FIGS. 12 and 13. The interatrial septum 110*c* may then be punctured, a guidewire 550*c* optionally placed into the left atrium 104, and the apparatus 214*c* withdrawn from the heart 100*c*, as with the first and second embodiments described above.

FIG. 14 depicts an alternate configuration of the third embodiment. The alternate configuration bears similarities to the second embodiment, in that a plurality of framing strands 652*c* make up the framing member 220*c*, and a plurality of target points 228*c* are arranged in a target grid 656. However, the multi-strand alternate configuration of FIG. 14 is deployed similarly to the single-strand framing member 220*c* previously described as the third embodiment. The framing strands 652*c* may be connected by framing cross members (not shown), or the apparatus 214*c* of the alternate configuration depicted in FIG. 14 may otherwise incorporate any suitable features from either the second or third embodiment of the present invention.

FIG. 15 illustrates a fourth embodiment of an apparatus 214*d*. The apparatus 214*d* of FIG. 15 is similar to the apparatus of FIGS. 2-5 and therefore, structures of FIG. 15 that are the same as or similar to those described with reference to FIGS. 2-5 have the same reference numbers with the addition of the suffix "d". Description of common elements and operation similar to those in the previously described embodiments will not be repeated with respect to the fourth embodiment.

The framing member 220*d* of the fourth embodiment has a flat, elongated ribbon-like structure, at least for the planar framing member body 226*d* portion thereof. The framing member 220*d* may be self-expanding, but is not necessarily so. The first and second framing member ends (not shown) may be of any suitable configuration. A plurality of target points 228*d* are arranged in a target grid 656*d* on a planar surface of the framing member body 226*d*. Target wires 230*d* may connect one or more target points 228*d* with one or more external power sources, for ease of location of the respective target points 228*d* within the right atrium.

The framing member 220*d* may be at least partially perforated or formed from mesh, an example portion of which is shown in dotted line in FIG. 15, to allow for the puncture needle or other structures to easily extend and/or pass through the thickness of the framing member 220d.

The framing member 220d of the fourth embodiment may be deployed similarly to the framing members 220b or 220c of the previously described second or third embodiments of the present invention. That is, the planar framing member body 226d and the target grid 656d may be part of either a closed-loop framing member 220b as in the second embodiment, or an anchored framing member 220c as in the alternate configuration of the third embodiment. In either case, the framing member body 226d is positioned in the right atrium with at least a portion of the target grid 656d adjacent the interatrial septum. The target point 228d location procedure may then be carried out as described above, with the interatrial septum being punctured (if desired) and the apparatus 214d removed from the right atrium as with the other embodiments of the present invention.

Figure 18:
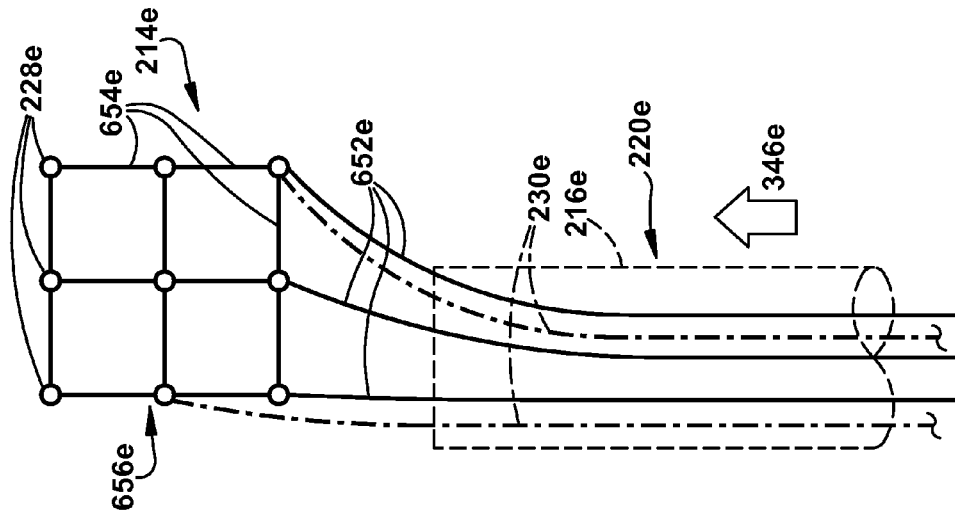
FIG. 18 is a side view of the fifth embodiment of FIG. 16 in a third condition.
Figure 17:
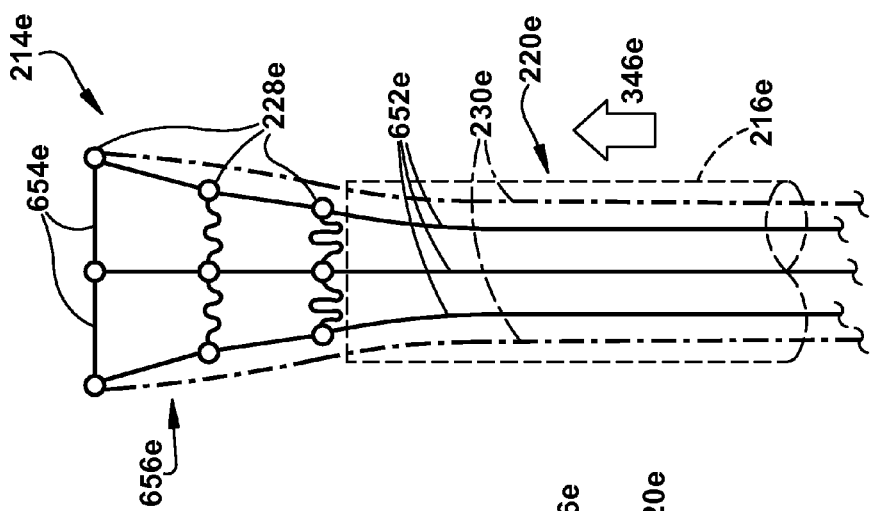
FIG. 17 is a side view of the fifth embodiment of FIG. 16 in a second condition.
Figure 16:
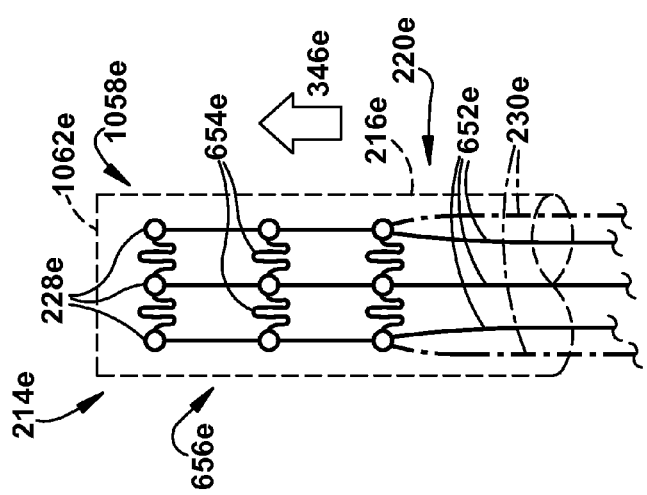
FIG. 16 is a side view of a fifth embodiment of the present invention in a first condition.

FIGS. 16-18 illustrate a fifth embodiment of an apparatus 214e. The apparatus 214e of FIGS. 16-18 is similar to the apparatus of FIGS. 2-5 and therefore, structures of FIGS. 16-18 that are the same as or similar to those described with reference to FIGS. 2-5 have the same reference numbers with the addition of the suffix "e". Description of common elements and operation similar to those in the previously described embodiments will not be repeated with respect to the fifth embodiment.

The apparatus 214e of the fifth embodiment includes a framing member 220e having a plurality of framing strands 652e connected by flexible framing cross members 654e. The framing strands 652e are self-expanding and are arranged to draw the framing cross members 654e taut in the second, expanded condition. The framing member 220e is held in a compressed configuration to fit within the catheter 216e in the first, collapsed condition.

The framing member 220e supports a plurality of target points 228e in a target grid 656e. Any number of target points 228e may have an associated target wire 230e. Unlike the previously described embodiments, the target grid 656e is located at or near the first framing member end 1058e of the framing member 220e in the fifth embodiment.

To deploy the framing member 220e of the fifth embodiment, the framing member and catheter 216e are relatively moved, such as by extending the framing member in the advancement direction 346e. As depicted in the sequence of FIGS. 17-18, the framing strands 652e begin to self-expand and separate from each other as they are released from the catheter outlet end 1062e. The framing cross members 654e restrain the framing strands 652e and thereby retain the target points 228e in the target grid 656e configuration.

In FIG. 18, the framing member 220e has reached the second, expanded condition, with the target grid 656e held apart from the catheter 216e in a cantilevered manner. The framing member 220e may then be manipulated to bring the target grid 656e adjacent the interatrial septum. The framing member 220e may be bent or curved in a predetermined manner to facilitate placement of the target grid 656e as desired with respect to the interatrial septum. Optionally, the framing strands 652e are of a sufficiently stiff material to allow for positive pressure to be applied against the interatrial septum by the target grid 656e.

Once the target grid 656e is in the desired position within the right atrium 102, the target point 228e location procedure may be carried out as described above, with the interatrial septum 110 being punctured and the apparatus 214e removed from the right atrium as with the other embodiments of the present invention.

As alluded to previously, any of the first through fifth embodiments of the present invention could be used to target a desired target site on any body tissue. Additionally, the target site could be chosen for any reason or because of any characteristic; as discussed previously, locating a puncture site is only one of many possible uses for the present invention. The body tissue could separate first and second body cavities of any portion of the patient's anatomy. Alternately, there need not be a second body cavity beyond/behind the body tissue of the first body cavity. As used herein, "body cavity" simply means an area of the patient's body from which or to which access is desired, such access to be provided by puncturing the body tissue. The first and second body cavities in the previously described use environment are the right and left atria 102 and 104, respectively. A "body cavity" need not be a tightly enclosed or defined open volume within the body, but could be any lumen within, or space between, any body structures, no matter how minimal. For ease of description, access to or from a "body cavity" will be considered herein to also encompass access between an internal body location and the space external to the patient's body (for example, puncturing through the abdominal skin inward to or outward from the peritoneal cavity for direct access thereto through the patient's abdomen).

FIGS. 19-23 schematically depict various example use environments of any embodiment of the present invention, in addition to the first example use environment previously depicted and described with respect to the first through fifth embodiments. However, the apparatus 214 of the first embodiment will be shown in schematic form in these Figures, for simplicity. Additionally, operation of several embodiments of the apparatus 214 has been previously described and will not be repeated below.

Figure 19:
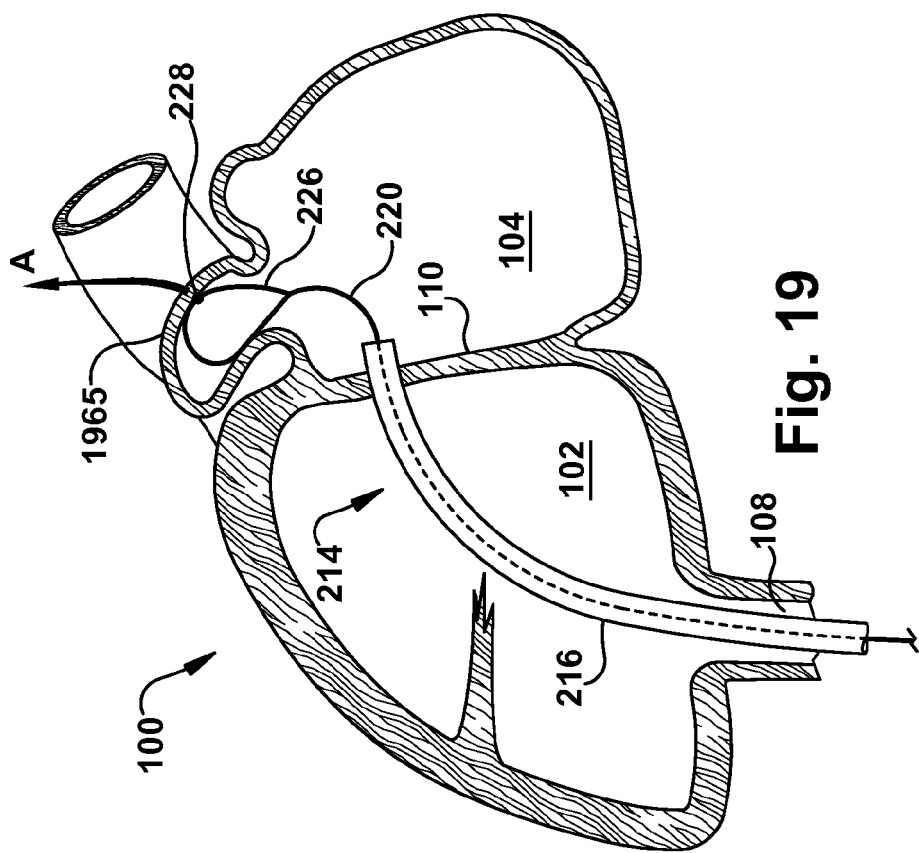
FIG. 19 is a schematic view of a second example use environment of any embodiment of the present invention.

FIG. 19 is a partial cross-sectional view of a heart 100 having right and left atria 102 and 104. In the second example use environment depicted, the catheter 216 has traveled through the inferior vena cava 108 to the right atrium 102. The apparatus 214 has already been used once to puncture through the interatrial septum 110, with the catheter 216 following the framing member 220 through the interatrial septum. However, the catheter 216 could instead be held within the right atrium 102, with only the framing member extending through the interatrial septum 110, as desired.

In the second example use environment of FIG. 19, the apparatus 214 is in a desired position on the body tissue forming a left atrial appendage 1966 of the heart 100. Arrow A depicts a possible path for a needle (not shown) to exit the left atrial appendage 1966 by a puncture at or near the target point 228, when such egress is desired. Such precise target site location within the left atrial appendage 1966 could be useful in many different surgical procedures. It is well-known that blood often clots within the left atrial appendage 1966, causing a risk of stroke, so it may be desirable, for example, to locate and/or prepare a target site for anchoring a blocking device within the left atrial appendage.

Since the left atrial appendage 1966 is not a "working tissue" of the heart 100, a puncture therethrough (and the resultant scar tissue) will not hinder ongoing operation of the heart. Accordingly, access into or out of the heart 100 may be desirably provided through the left atrial appendage 1966 wall, to avoid damaging otherwise intact structures and tissues of the heart during access. For example, the catheter 216 may be inserted into the body endovascularly, as shown in FIG. 19, and the left atrial appendage 1966 punctured (with targeting assistance from the apparatus 214). The catheter 216 could then be advanced through the left atrial appendage 1966 and through the chest cavity structures in an outward direction. The apparatus 214 could then be used to precisely target an emergence location for the catheter 216 to pass through the patient's chest wall and provide direct percutaneous access to the heart 100 without necessitating a potentially damaging and imprecise cut-down procedure from the patient's chest wall toward the heart. Thus, the patient's chest structure could be more readily navigated, and possibly preserved, during percutaneous procedures (for example, aortic or mitral valve replacements) using the apparatus 214 and the described "inside-out" technique than if the heart 100 were to be blindly accessed from the outside in, as is traditionally done. Further, chest incisions and/or exposure of the heart 100 to the ambient atmosphere, for stabilizing the cardiac structures, are avoided through use of this inside-out access.

Figure 20:
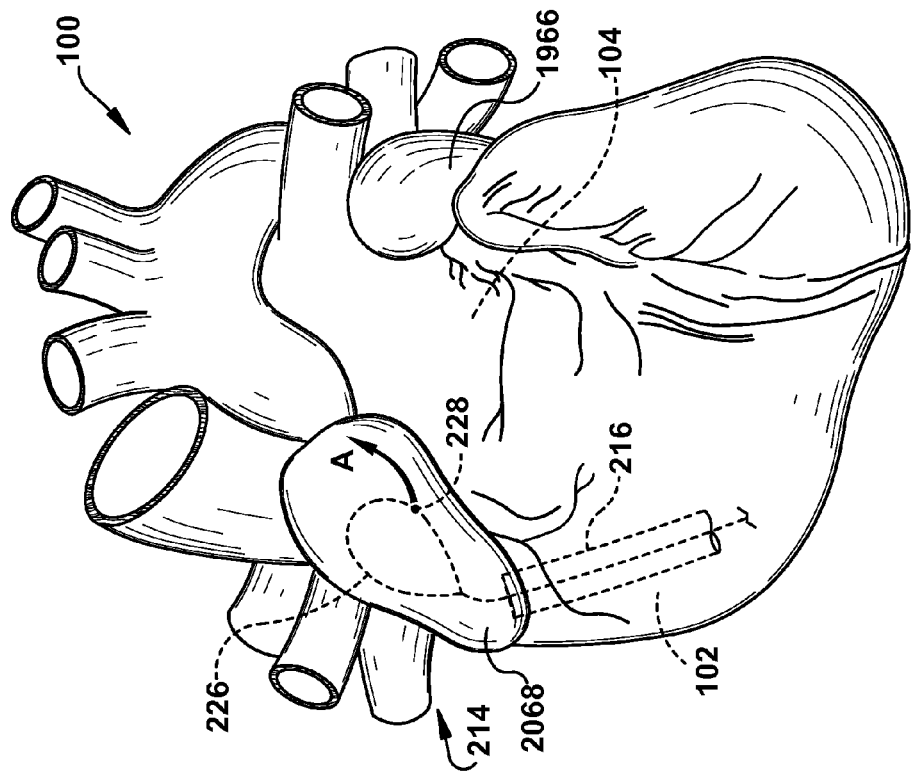
FIG. 20 is a schematic view of a third example use environment of any embodiment of the present invention.

FIG. 20 is a schematic external view of the heart 100, depicting a third example use environment of any embodiment of the present invention. The third example use environment is similar to the second example use environment, except that instead of the left atrial appendage 1966, the apparatus 214 is being used to locate a target site within a right atrial appendage 2068. The catheter 216 has previously been inserted into the right atrium 102 in any suitable manner, and the framing member 220 is depicted in FIG. 20 as being located adjacent the body tissue making up the right atrial appendage 2068 wall. The target point 228 in FIG. 20 is located adjacent an inner surface of the right atrial appendage 2068 wall, ready to guide a needle (not shown), if desired, to puncture from that location within the right atrial appendage 2068 outward from the heart 100, possibly in the direction of Arrow A. Inside-out access through the right atrial appendage 2068 in this manner may be useful, for example, in conducting surgical procedures on one or more of the tricuspid valve, pulmonary valve, or interatrial septum.

In either of the second or third example use environments, or any other use environment, the apparatus 214 can be used in the reverse orientations from those depicted. That is, the apparatus 214 can enter the patient's body from outside the heart 100 in any desired manner, and the target point 228 can be used to accurately identify a desired target site on either the left or right atrial appendage 1966 or 2068 or another portion of the heart 100, through which the interior of the heart can be accessed. Though the left and right atrial appendages 1966 and 2068 are used as examples herein, the apparatus 214 could be used at any location on the heart 100, internally or externally, to assist in providing either inward or outward access through a heart wall.

Figure 21:
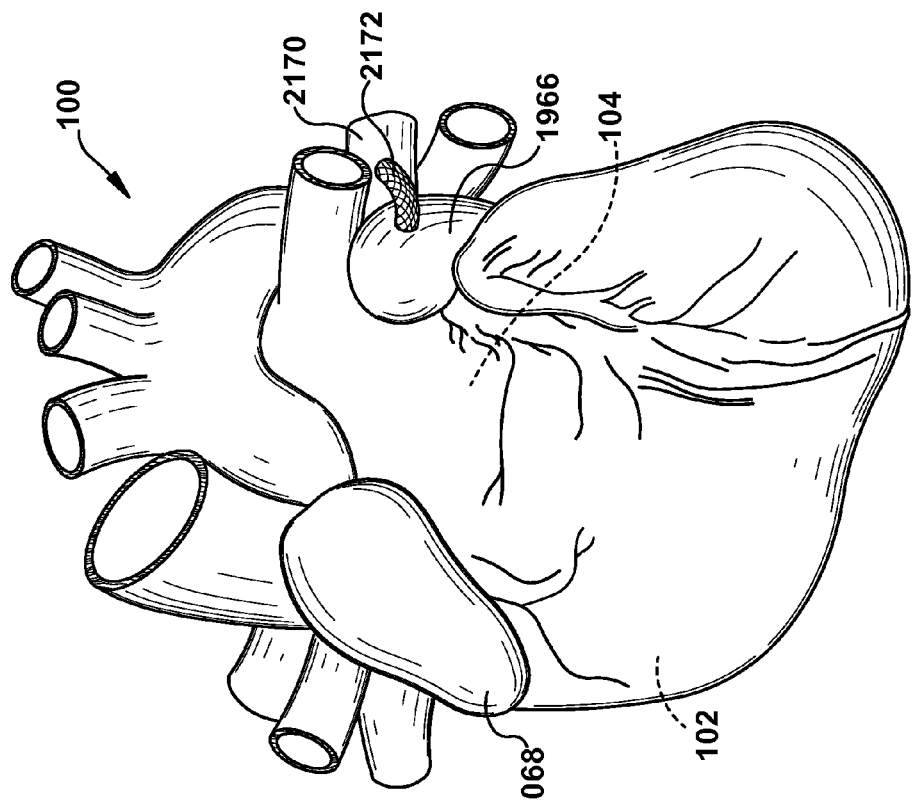
FIG. 21 is a schematic view of a fourth example use environment of any embodiment of the present invention.

A fourth example use environment of any embodiment of the present invention is depicted in FIG. 21. As previously mentioned, blood can stagnate within the left atrial appendage 1966 in an undesirable manner which results in hazardous clotting therein. Blood normally flows to the left atrium 104 through the left pulmonary vein 2170, and if a portion of the inflowing blood could be diverted from the left pulmonary vein through the left atrial appendage 1966, the resultant "flushing" action could keep the blood within the left atrial appendage from stagnating and clotting. Therefore, a flushing conduit 2172 may be used to connect the left pulmonary vein 2170 directly to the left atrial appendage 1966 to facilitate such an alternate flow path.

As shown in FIG. 21, the apparatus 214 has already been used to puncture the walls of the left pulmonary vein 2170 and the left atrial appendage 1966, and the flushing conduit 2172 is depicted as extending therebetween. One of ordinary skill in the art can readily determine the insertion points, direction/order of puncture of the left pulmonary vein 2170 and the left atrial appendage 1966 walls, and method of placing the flushing conduit 2172 for a particular patient. The apparatus 214 may be especially useful in this fourth example use environment because of the need for extremely precise positioning of the ends of the flushing conduit 2172 to fully flush the left atrial appendage 1966 and substantially eliminate stagnation of blood therein.

Figures 22, 23:
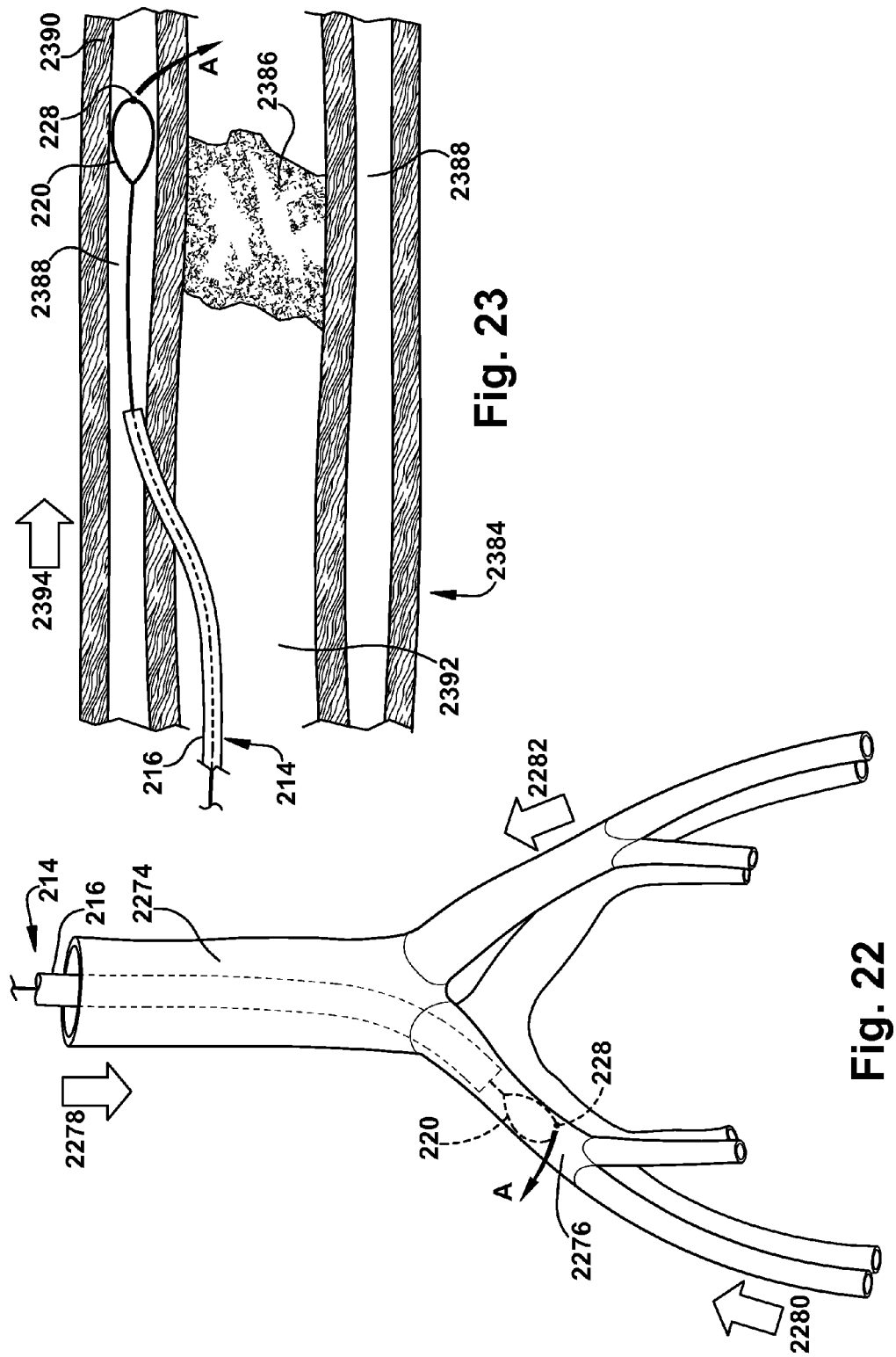
FIG. 22 is a schematic view of a fifth example use environment of any embodiment of the present invention.
FIG. 23 is a schematic view of a sixth example use environment of any embodiment of the present invention.

FIG. 22 depicts a fifth example use environment, including a portion of the abdominal aorta 2274 and the associated common iliac artery 2276, through which the framing member 220 is depicted as extending. The catheter 216 has been inserted in a brachial insertion direction 2278, routed through the abdominal aorta 2274, and the apparatus is now ready to guide a needle (not shown) to puncture the common iliac artery 2276 outward, in a direction such as that indicated by Arrow A (possibly toward the abdominal wall), in the depicted configuration. In this manner, the common iliac artery 2276 can be punctured precisely at a desired target site, avoiding surrounding vascular, neurological, or other structure, and the apparatus 214 can then be used to extend through the abdominal wall and outside the patient's body. Alternately, the target site could be marked or otherwise used to advantage without being punctured or altered. Once the apparatus 214 has exited the body, in a puncture procedure, a sheath or conduit can be extended through the exit point and back to the target site on the common iliac artery 2276. Because of this inside-out access procedure, the user may enter the common iliac artery 2276 at a specific location without fear of piercing all the way through opposing wall of the common iliac artery and "missing" the lumen thereof while damaging the opposing wall. Access in this manner may be desirable, for example, in conducting a percutaneous aortic valve replacement procedure, or any other procedure in which direct access between the common iliac artery 2276 and the outside of the patient's body is desired.

Though not all are depicted in FIG. 22, the framing member 220 could reach the target site shown along any of several paths. For example, the apparatus 214 could be inserted from a corresponding femoral artery (not shown) and advanced toward the depicted target site in a femoral insertion direction 2280. Similarly, and as another example, the apparatus 214 could be inserted from a contralateral femoral artery (not shown) and advanced toward the depicted target site in a contralateral femoral insertion direction 2282. More generally, the fifth example use environment depicted in FIG. 22 is merely one of a multitude of locations within a patient's body where a blood vessel, or other first body cavity or lumen, can be placed into communication with the outside of the patient's body or with at least one other body cavity, whether or not the first body cavity is adjacent the second or more body cavities. For example, the fifth example use environment could be related to an inside-out or outside-in procedure using a carotid or subclavian structure. Indeed, even if no puncture is carried out, the apparatus 214 could be useful in locating a target site in any portion of a patient's vasculature. For example, the target site could be a void, such as a junction point with a side branch or anastomosis location, in a wall of a blood vessel.

In FIG. 23, a sixth example use environment of the present invention is depicted. A blood vessel 2384 is substantially blocked by an obstruction 2386, which may be a blood clot, plaque, or any other obstructive material. The blood vessel 2384 could be any suitable blood vessel 2384 such as, but not limited to, the superficial femoral artery. In order to bypass or remove the obstruction 2386, it may be desirable to route a catheter 216 through the subintimal space 2388 defined within the vessel wall 2390 adjacent the obstruction. As shown in FIG. 23, the catheter 216 has already been guided from the blood vessel lumen 2392 into the subintimal space 2388, optionally through use of the framing member 220 and associated target point 228. The apparatus 214, or portions thereof, are shown as being routed through the subintimal space 2388 in a bypass direction 2394, traveling in parallel with the blood vessel lumen 2392 while avoiding the obstruction 2386. Once the apparatus 214 has passed beyond the obstruction 2386, the framing member 220 and target point 228 can be used to help re-introduce the apparatus to the blood vessel lumen 2392, possibly in the direction of Arrow A. This will establish an alternate or bypass route, through the subintimal space 2388 of the blood vessel 2384, which avoids the obstruction 2386. Since the subintimal space 2388 is very small, an apparatus 214 according to the present invention may be useful in ensuring that the vessel wall 2390 is punctured precisely at the desired location and that the puncture needle (not shown) does not penetrate entirely through the subintimal space and beyond the vessel wall 2390. As with any of the embodiments and example use environments of the present invention, the apparatus 214 can assist with precisely locating the desired target site and, as appropriate, stabilizing the puncture needle to facilitate providing access through a body tissue in a desired manner.

Figure 25:
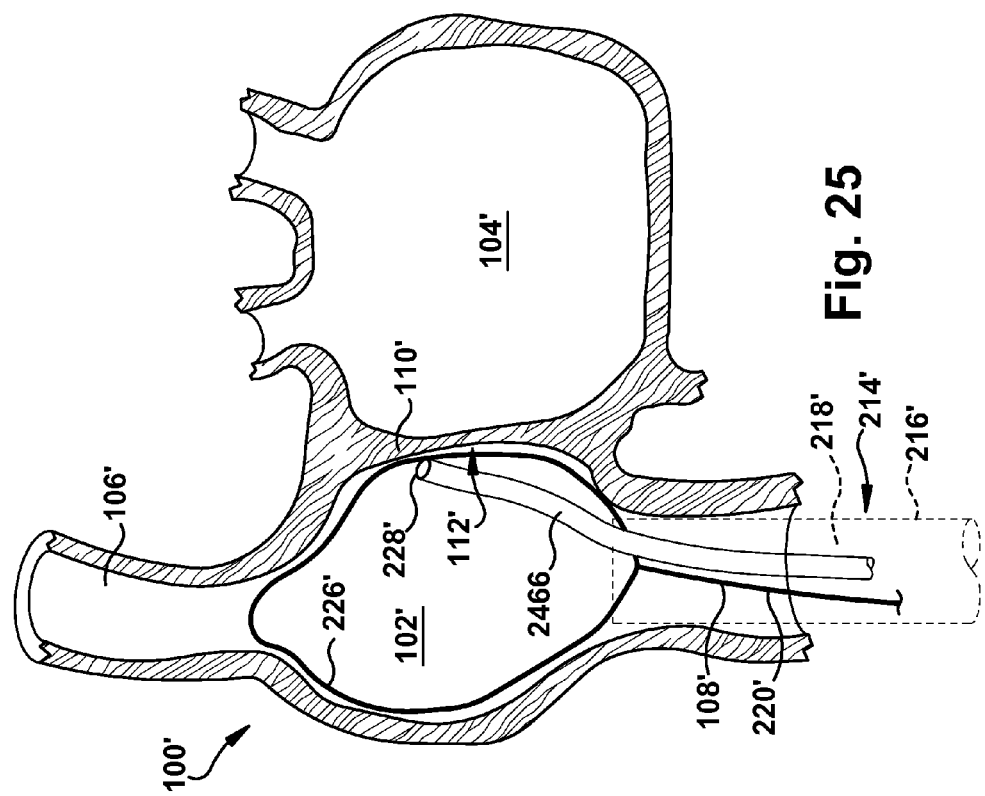
FIG. 25 is a side view of the seventh embodiment of FIG. 26 in a second condition within a heart.
Figure 24:
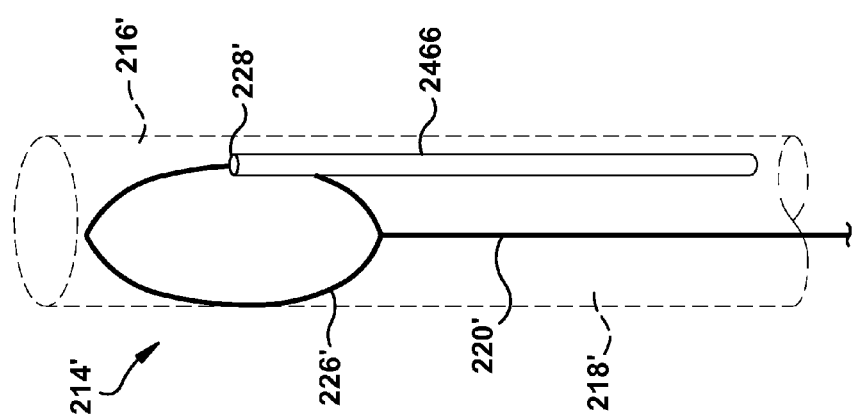
FIG. 24 is a partial side view of a seventh embodiment of the present invention.

FIGS. 24-25 illustrate a seventh embodiment of an apparatus 214'. The apparatus 214' of FIGS. 24-25 is similar to the apparatus of FIGS. 2-5 and therefore, structures of FIGS. 24-25 that are the same as or similar to those described with reference to FIGS. 2-5 have the same reference numbers with the addition of a "prime" mark. Description of common elements and operation similar to those in the previously described embodiments will not be repeated with respect to the seventh embodiment.

As shown in FIG. 24, the target pathway in the seventh embodiment includes a target lumen 2466, which is shown as a flexible tubular structure which is attached to or near the target point 228' and extends at least a portion of the distance through the catheter lumen 218'. For example, the target lumen 2466 may place the target point 228' in fluid communication with a location outside the patient's body. Through use of the target lumen 2466, a user may pass a puncture needle (omitted from FIG. 24) through the catheter lumen 218' and to the desired target site without the use of the aforementioned needle coupler 240' or similar guiding devices. In other words, the target lumen 2466 itself can act as a guiding device for access to the desired target site.

The target lumen 2466 may also or instead be used to direct fluids to the desired target site, optionally with the assistance of a stopcock or direct connection between the target lumen and a fluid source (not shown) outside the patient's body or located upon/within the apparatus 214' distal to the desired target site. For example, a dye, saline, or even a plurality of small coils (behaving in a pseudo-fluidic manner) (none of these shown) could be directed to the desired target site through the target lumen 2466.

As shown in FIG. 25, the apparatus 214' according to the seventh embodiment may be provided to the patient's body similarly to other, earlier described embodiments of the present invention. As with the first embodiment, the target lumen 2466 provides a target pathway which is attached to at least one target point 228', at least a portion of the target pathway extends through the catheter lumen 218', and the target pathway is substantially spaced apart from the framing member body 226' (though the relatively small portion of the target lumen 2466 which is attached to the target point 228' may be located adjacent or even in contact with the framing member body without destroying this "substantial spacing apart"). It is contemplated that multiple target lumens 2466 (not shown) could be provided to the apparatus 214', similarly to the multiple target wires shown at least in FIGS. 6-9 and 14-18. It is also contemplated that a single target lumen 2466 may be large enough to be associated with multiple target points 228' at one time. For example, a single target lumen 2466 could be sized to be attached to and/or substantially surround multiple or all of the target points of the grid shown in FIG. 6.

FIGS. 26-27 illustrate an eighth embodiment of an apparatus 214". The apparatus 214" of FIGS. 26-27 is similar to the apparatus of FIGS. 2-5 and therefore, structures of FIGS. 26-27 that are the same as or similar to those described with reference to FIGS. 2-5 have the same reference numbers with the addition of a double "prime" mark. Description of common elements and operation similar to those in the previously described embodiments will not be repeated with respect to the eighth embodiment.

As shown in FIGS. 26-27, the target pathway includes a combination of a target wire 230" and a relatively short target lumen 2466". At least a portion of the target lumen 2466" serves also as a target point 228". The target wire 230" is either directly or indirectly attached to the target point 228". For example, the target wire 230" may pass through at least a portion of the target lumen 2466" and may be held in that relationship in any suitable manner.

Optionally, and as shown in FIGS. 26-27, a puncture needle 232" may be associated with at least one of the target lumen 2466" and target wire 230" for insertion along with the framing member 220" through the catheter lumen 218". In this manner, the puncture needle 232" can be associated with the structures of the apparatus 214" before the apparatus is placed in the patient's body. When the puncture needle 232" is pre-associated in this manner, the framing member 220", with attached puncture needle, is expanded as described above. The puncture needle 232" is then placed at the desired target site by the expansion of the framing member 220" and may be remotely moved (e.g., via manipulation of the target wire 230") to puncture the patient tissue at the desired target site. When the target wire 230" is used to move the puncture needle 232", it may be desirable for the target wire to be movably attached to the target point 228", such as for reciprocating or unidirectional axial movement with respect to the target lumen 2466".

FIGS. 28-35C illustrate a ninth embodiment of an apparatus 214f. The apparatus 214f of FIGS. 28-35C is similar to the previously described apparatuses 214, 214', 214", and therefore, structures of FIGS. 28-35C that are the same as or similar to those described with reference to FIGS. 2-27 have the same reference numbers with the addition of the suffix "f". Description of common elements and operation similar to those in the previously described embodiments will not be repeated with respect to the ninth embodiment.

Figure 28:
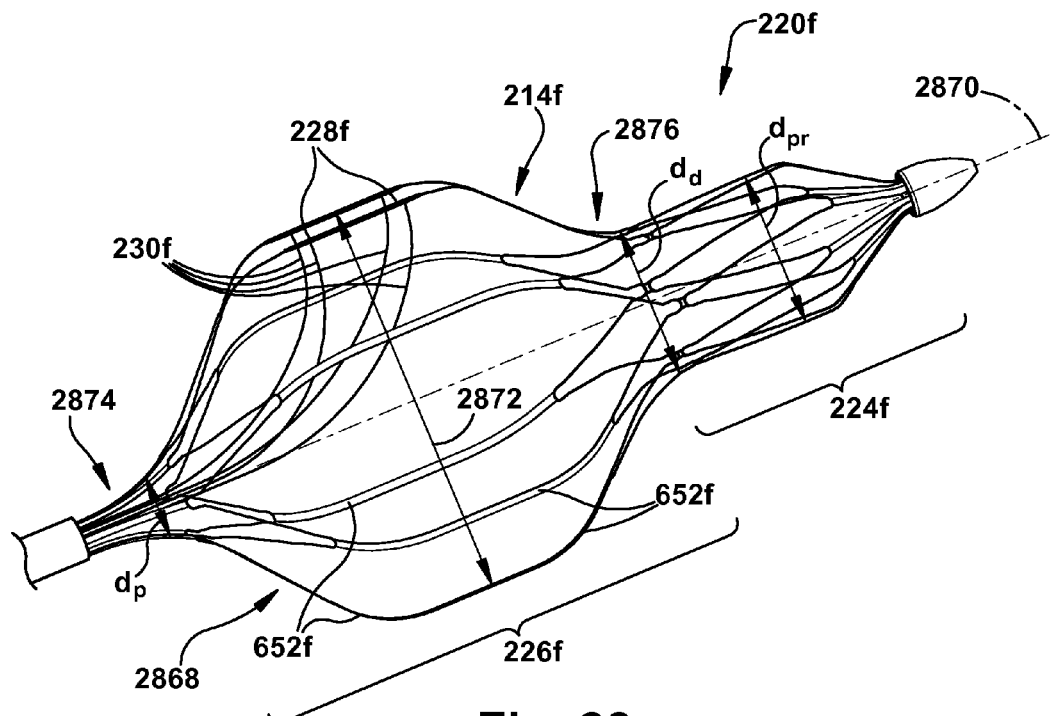
FIG. 28 is a side view of a ninth embodiment of the present invention.

As shown in FIGS. 28-31, the apparatus 214f includes a framing member 220f having a collapsed condition in which the framing member is adapted for insertion into the first body cavity, presumed below to be the right atrium 102, and an expanded condition in which the framing member is adapted for placement within the right atrium. In FIGS. 28-31, the apparatus 214f is in the expanded condition, in which it can be seen that the framing member 220f has a framing member body 226f which includes a three-dimensionally bulbous portion 2868 defining a maximum body footprint in a lateral dimension. As shown in FIG. 28, the lateral dimension is substantially perpendicular to a longitudinally extending central framing member axis 2870. The phrase "three-dimensionally bulbous" is used herein to indicate a rounded, optionally spherelike, portion of the apparatus 214f which extends in three dimensions and may be configured or shaped, in some embodiments of the present invention, to substantially mimic the general shape, dimensions, and/or configuration of the internal right atrium surface 348 (or other internal body cavity surface in which the present invention is used).

Figure 31:
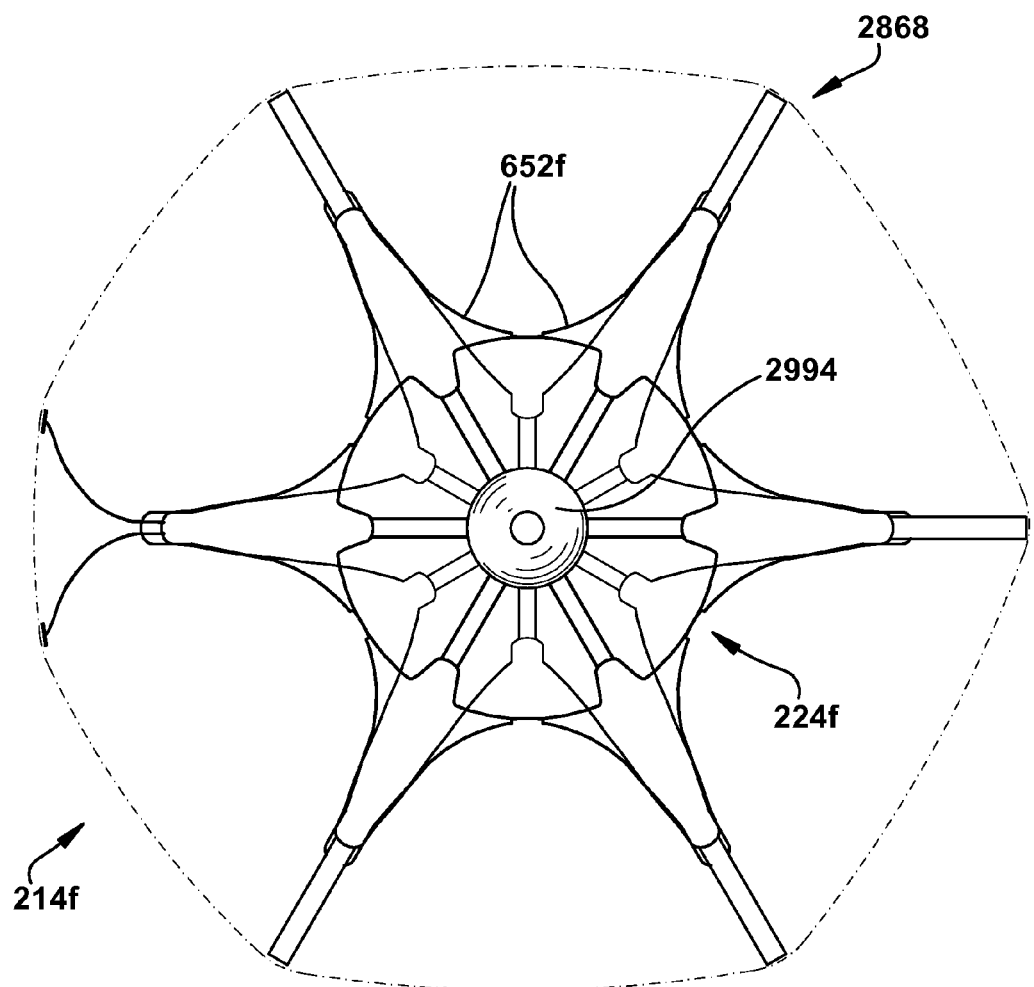
FIG. 31 is a front view of the ninth embodiment of FIG. 28.

The "maximum body footprint" is used herein to indicate the largest dimension/profile/contour of the bulbous portion 2868 (when fully deployed in the expanded condition) when viewed from a vantage point along the central framing member axis 2870 longitudinally spaced from the framing member 220f. As shown in FIGS. 28-31, and particularly by the dotted line in FIG. 31, the maximum body footprint of the depicted framing member 220f is a substantially circular "shape" (i.e., not a complete circle defined by a structure, but a suggested circle, as shown in FIG. 31, drawn around the outer extent of the framing member 220f) located approximately at the longitudinal position, along the bulbous portion 2868, of the indicated largest diameter 2872 of the bulbous portion.

(The term "diameter" is used herein for convenience to indicate a maximum width of a laterally-oriented [i.e., substantially perpendicular to the central framing member axis 2870] cross-section of a structure of any shape, but the use of "diameter" does not imply that the cross-section is, in fact, circular or even curvilinear. Additionally, the cross-section need not have a continuously defined outer perimeter; merely a general impression of a shape which could be formed by connecting the "dots" provided by the cross-sections of the individual framing strands 652f could suffice to approximate a perimeter or outer contour of the cross-section which could be considered a body footprint.)

The framing member 220f has longitudinally spaced proximal and distal body ends, shown approximately at 2874 and 2876, respectively, which are both longitudinally separated from the maximum body footprint of the bulbous portion 2868. As can be seen in FIGS. 28-31, the bulbous portion 2868 has a significantly smaller diameter at the proximal and distal body ends 2874 and 2876 (the respective diameters called out in FIG. 28 at $d_p$ and $d_d$, respectively) than is the diameter 2872 at the maximum body footprint. While diametrical indicators $d_p$ and $d_d$ are shown in FIG. 28 at appropriately approximate locations upon the proximal and distal body ends 2874 and 2876, one of ordinary skill in the art will realize that the proximal and distal body ends may not be precisely delineated or distinguished from adjacent and/or contiguous portions of the framing member 220f, but that, instead, a rather gradual transition from, for example, the proximal body end to the bulbous portion 2868 to the distal body end may take place along the central framing member axis 2870. However, that person of ordinary skill in the art will readily be able to differentiate the various described portions of the apparatus 214f, such as the proximal and distal body ends 2874 and 2876 and the bulbous portion 2868, from each other to the extent needed to understand and use the present invention.

Figure 29:
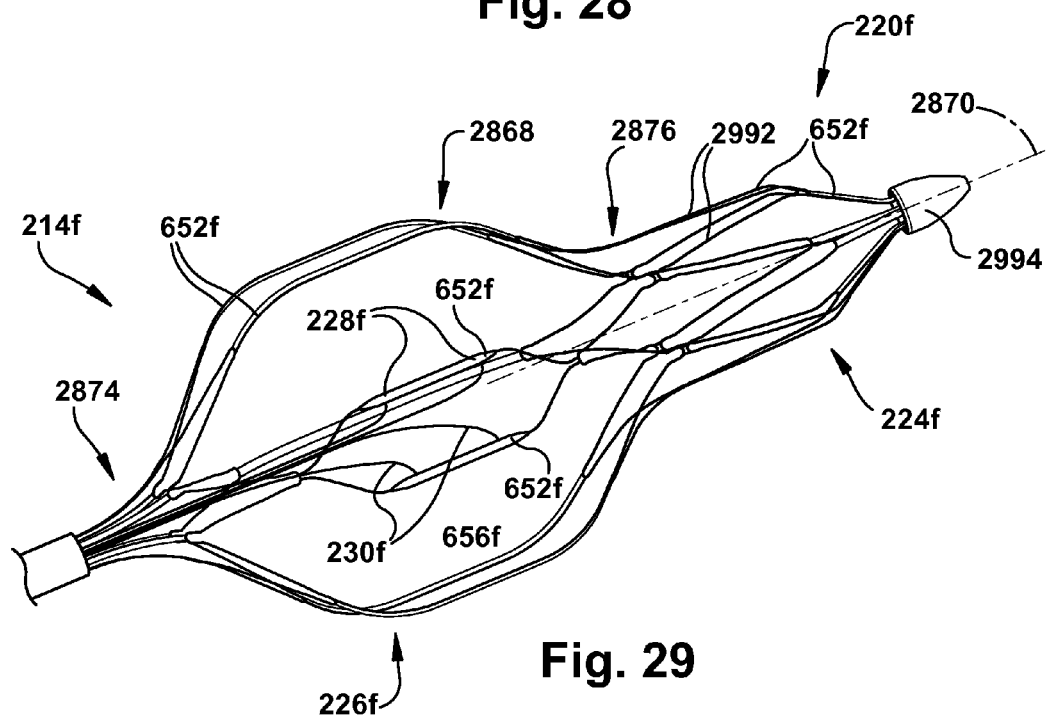
FIG. 29 is a side view of the ninth embodiment of FIG. 28.
Figure 30:
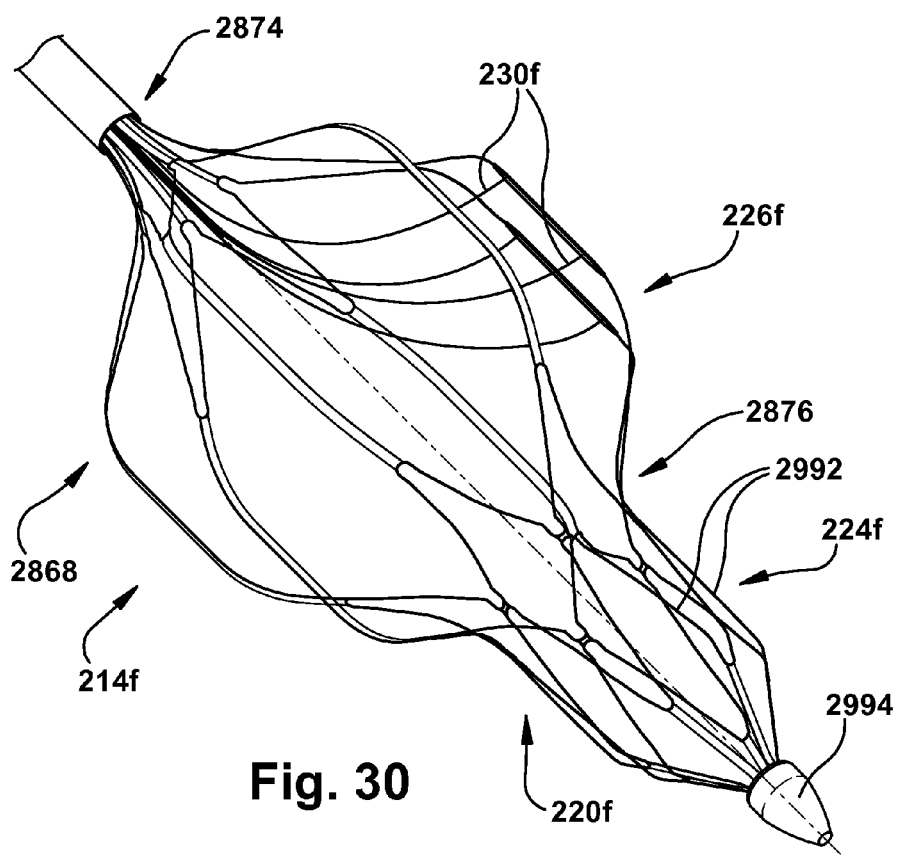
FIG. 30 is a front perspective view of the ninth embodiment of FIG. 28.

As shown in FIG. 29, a target array, here shown as a target grid 656f, is provided at increased-width areas of selected framing strands 652f, with the target points 228f carried by the bulbous portion 2868. (It should be noted that, as with several other features of the present invention, it is impractical to specifically call out and number each individual framing strand 652f of the apparatuses 214f of all of the Figures, so most of the framing strands have been left unnumbered without prejudicing or disclaiming their status as framing strands.) Here, a plurality of target wires 230f are provided to the apparatus 214f and attached to the framing member 220f at the target points 228f indicated. Optionally, one or more radiopaque markers may be provided at or near the target grid 656f to assist the user with locating the target points 228f when the apparatus 214f is located within the right atrium 102.

As shown in FIGS. 28-31, the framing member 220f may be substantially rotationally symmetrical about the central framing member axis 2870, along substantially the entire longitudinal length of the framing member 220f. The presence of minor local features, such as the target points 228f, target wires 230f, increased-width portions of selected framing strands 652f, or the like, will not destroy the overall substantial rotational symmetry of the framing member 220f, as will be understood by one of ordinary skill in the art. In other words, the framing member 220f shown in FIGS. 28-31 will be understood to have substantial rotational symmetry, in the context of the present invention.

In the ninth embodiment, a target catheter 3278, shown in FIG. 32, is provided. The target catheter 3278 has a longitudinally extending target catheter lumen 3280 surrounded by a tubular target catheter wall 3282 having an outer surface 3284. The proximal body end 2874 of the framing member body 226f is attached to the outer surface 3284 of the target catheter wall 3282. In embodiments of the present invention where a target catheter 3278 is provided, the target catheter 3278 may be used to manipulate the framing member 220f within the delivery catheter 216 and/or the right atrium 102. The target catheter 3278 may also or instead be used to at least partially enclose one or more target wires 230f, optionally with associated puncture needles, needle catheters, and/or needle couplers, for provision to the framing member 220f during targeting and/or puncturing use of the apparatus 214f.

One suitable means for attaching the proximal body end 2874 of the framing member body 226f to the target catheter 3278 is shown in FIGS. 33A-33C. Here, the proximal body end 2874 is shown as a cylindrical, cuff-like structure which includes one or more fenestrations 3386 laterally therethrough. The proximal body end 2874 substantially mates with the outer surface 3284 of the target catheter wall 3282, accepting the target catheter wall thereinto. A bonding sleeve 3388, which may be separately provided, laterally and concurrently surrounds at least a portion of both the proximal body end 2874 and the outer surface 3284 of the target catheter wall 3282. The proximal body end 2874 is then attached to the outer surface 3284 at least partially through direct adhesion of the bonding sleeve 3388 to the outer surface laterally through at least one fenestration 3386 in the proximal body end 2874 of the framing member 220f—this adhesion is shown via attraction arrows 3390 in FIGS. 33B-33C, although the structures in this Figure are shown laterally spaced apart for ease of depiction. The adhesion between the bonding sleeve 3388 and the outer surface 3284 may occur via heat-melting (particularly if one or both are plastic materials), chemical adhesion, mechanical adhesion, or any other desired means of adhesion or combination thereof. One of ordinary skill in the art can readily provide any desired means for attaching the proximal body end 2874 of the framing member body 226f to the target catheter 3278, however, other than that shown in FIGS. 33A-33C, such as, but not limited to, mechanical, chemical, adhesive, magnetic, or any other means for attachment or combination thereof.

Returning to the ninth embodiment of FIGS. 28-31, the framing member 220f may include a protrusion 224f, which may be located at the distal body end 2876 of the framing member body 226f and extend longitudinally from the distal body end 2876 of the bulbous portion 2868. When present, the protrusion 224f may have a diameter $d_{pr}$ which is smaller than the diameter 2872 of the maximum body footprint. The protrusion 224f may have any desired shape, size, configuration, or other physical property/ies, and may be provided for any desired reason.

More specifically, the protrusion 224f of the ninth embodiment may be characterized as a "closed-crown" type. That is, and with reference particularly to FIGS. 29-30, the protrusion 224f includes a plurality of protrusion body beams 2992 extending longitudinally distally from the distal body end 2876 of the bulbous portion 2868. Each protrusion body beam 2992 extends along/within a plane which is substantially parallel to, and laterally spaced from, the central framing member axis 2870. That is, though individual ones of the protrusion body beams 2992 are angled with respect to the central framing member axis 2870, they are each contained within a plane which itself is substantially parallel to, and laterally spaced from, the central framing member axis 2870—the "topmost" and "bottommost" (in the orientation of FIG. 29) protrusion body beams 2992, for example, each extend along a plane that is perpendicular to (extends into and out of) the plane of the page. A hub 2994 is located at a distalmost end of the protrusion 224f, and may include an aperture extending longitudinally therethrough for accepting a guidewire (not shown). The hub 2994 is longitudinally spaced distally from each of the protrusion body beams 2992. By virtue of being substantially co-located with/along the central framing member axis 2870, the hub 2994 is also spaced laterally from each of the protrusion body beams 2992, which themselves are laterally spaced from the central framing member axis. The protrusion 224f also includes a plurality of protrusion cap beams 2996. Each protrusion cap beam 2996 extends at an angle (here, approximately 145°, measured toward the proximal direction) relative to the central framing member axis 2870. The protrusion cap beams 2996 both laterally and longitudinally connect the hub 2994 with the distalmost ends of the protrusion body beams 2992 to "close" the distal end of the framing member 220f and thus at least partially obstruct access from the distalmost end of the protrusion 224f directly along the central framing member axis 2870 to an interior of the bulbous portion 2868.

One example of a protrusion 224f which may be used in conjunction with the present invention involves a use environment wherein the body cavity is a right atrium 102, as is described herein. In the right atrium 102 use environment, when the framing member 220f is in the expanded condition, the protrusion 224f may at least partially enter a chosen one of the superior vena cava 106 and the inferior vena cava 108. More specifically, and when the protrusion 224f is of the closed-crown type shown in FIGS. 28-31, the hub 2994 and at least a portion of the protrusion cap and body beams 2996 and 2992 (though often the whole of the protrusion cap beams 2996) may enter the chosen one of the superior vena cava 106 and the inferior vena cava 108. Without limitation of the structures of the protrusion involved, however, at least a portion of the protrusion 224f could be configured to exert an anchoring force upon the chosen one of the superior vena cava 106 and the inferior vena cava 108 to resist displacement of the expanded framing member 220f within the right atrium 102. This displacement could take the form of lateral (e.g., side-to-side perpendicular to the central framing member axis 2870), radial (e.g., rotary around the central framing member axis or a rotation axis substantially parallel to the central framing member axis), and/or longitudinal (e.g., along or parallel to the central framing member axis) movement of the framing member 220f.

The anchoring force could arise in any suitable manner. For example, the protrusion 224f could be configured to have a diameter $d_{pr}$ which is slightly larger than an internal wall diameter of the chosen one of the superior vena cava 106 and the inferior vena cava 108 in one or more dimensions when in the expanded condition, in order to exert a positive pressure against the chosen one of the superior vena cava and the inferior vena cava. As another example, the mere extension of the protrusion 224f into the chosen one of the superior vena cava 106 and the inferior vena cava 108 could act in a "peg-in-hole" manner, even if the protrusion is not in continuous contact with the chosen one of the superior vena cava and the inferior vena cava, to prevent the framing member 220f from rotating or precessing within the right atrium 102.

Regardless of the presence, configuration, and/or function of the protrusion 224f, it is contemplated that the framing member body 226f, when in the expanded condition, may exert positive pressure at a plurality of locations on the body tissue comprising at least a portion of the interior surface of the right atrium 102, or whatever body cavity is being accessed, in order to maintain a position of the at least one target point 228f adjacent to the body tissue as desired. In other words, the framing member 220f, or portions thereof, may be configured to at least approximate the shape of an internal contour of at least a portion of the body cavity being accessed, whether in general (e.g., an average right atrium 102 shape) or in particular (a right atrium 102 shape personalized for the right atrium of a particular patient)—even if such approximation destroys the rotational symmetry of the framing member 220f. Optionally, at least a portion of the shape of the framing member 220f may be configured to be, when expanded, slightly larger in one or more dimensions than a corresponding shape/contour/area of the body cavity, in order to brace against the internal wall of the body cavity and exert a positive pressure thereagainst to help maintain the target point 228f in a desired position.

Figure 34A:
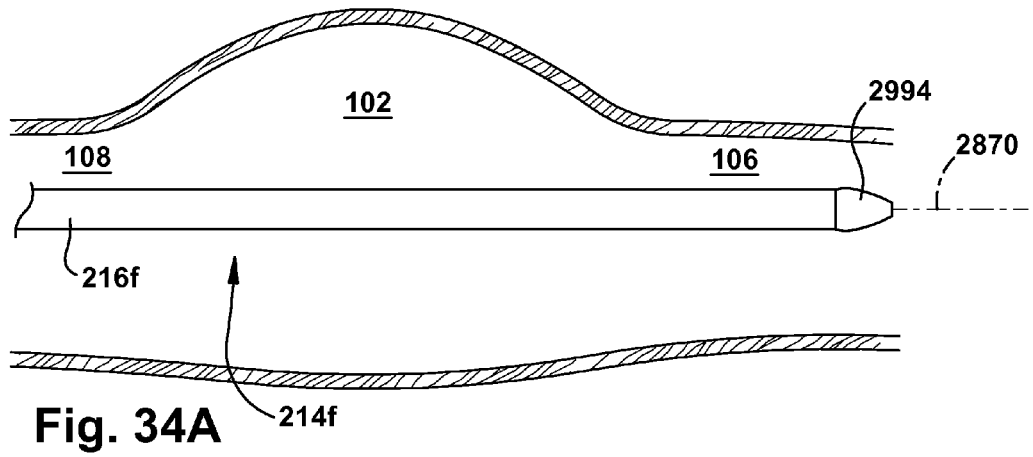
FIGS. 34A-34E depict an example sequence of deployment of the ninth embodiment of FIG. 28.

With reference to the sequence of FIGS. 34A-34E, an example deployment of the apparatus 214f according to the ninth embodiment within a right atrium 102 is shown schematically. (Many element numbers have been omitted from FIGS. 34A-34E for clarity of depiction, but one of ordinary skill in the art will be able to analogize the apparatus 214f of FIGS. 34A-34E to the apparatus 214f shown in at least FIGS. 28-31.) In FIG. 34A, the framing member 220f is in a fully collapsed condition and is constrained within the delivery catheter 216f, which has been advanced, in any suitable manner, into a patient's right atrium 102.

A distal end (toward the right side of the page, in the embodiment of FIGS. 34A-34E) of the delivery catheter 216f has been placed into the patient's body in any suitable manner and advanced into the right atrium 102. In FIGS. 34A-34E, the delivery catheter 216f has actually been advanced into, and substantially through, the right atrium 102, and extends into the superior vena cava 106. In these Figures, the delivery catheter 216f is advanced to a "terminal location" of the patient's body tissue which is desired for a distalmost structure of the framing member 220f to occupy during and/or after deployment of the framing member from the collapsed condition to the expanded condition. The terminal location may be within the first body cavity, or may instead be adjacent to, and separate from, the first body cavity. In FIGS. 34A-34E, the terminal location is just within the superior vena cava 106.

Figure 34B:
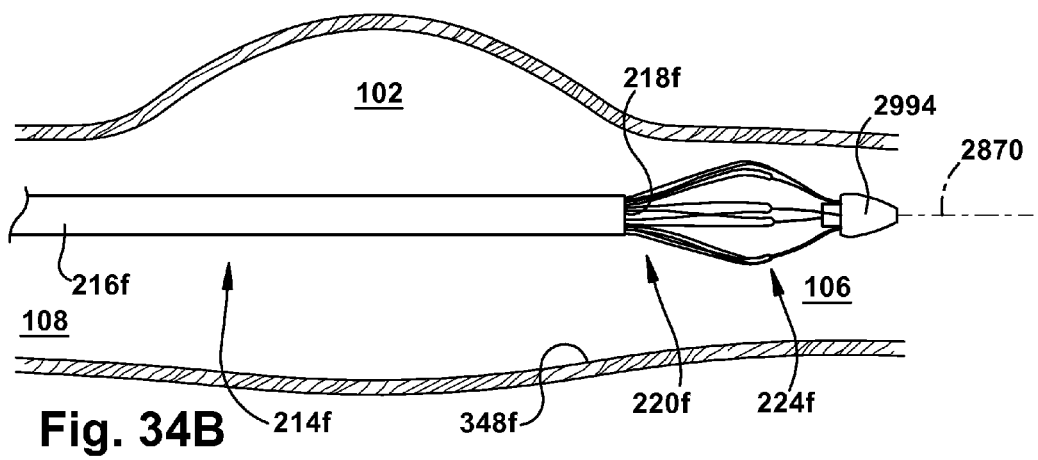

Once the delivery catheter 216f has been used to arrange the collapsed framing member 220f in a desired position relative to the right atrium 102, the distalmost end (here, the hub 2994 of the protrusion 224f) is located at, and maintained at, the desired terminal location (here, just within the superior vena cava 106). Next, and as is shown in FIG. 34B, the framing member 220f is maintained at the desired terminal location (e.g., through maintenance of the target catheter 3278 in position) and the delivery catheter 216f is retracted to permit the protrusion 224f to extend from the delivery catheter lumen 218f. As it is released from the delivery catheter 216f, the protrusion 224f self-expands, as shown in FIG. 34B. The protrusion 224f may be maintained at the desired terminal location and may exert a laterally oriented anchoring force outward from the central framing member axis 2870 against the body tissue at the terminal location (here, just inside the superior vena cava 106) to substantially prevent movement of the framing member 220f within the right atrium 102 during the transition of the framing member from the collapsed condition to the expanded condition and/or maintenance of the framing member in the expanded condition.

Figure 34C:
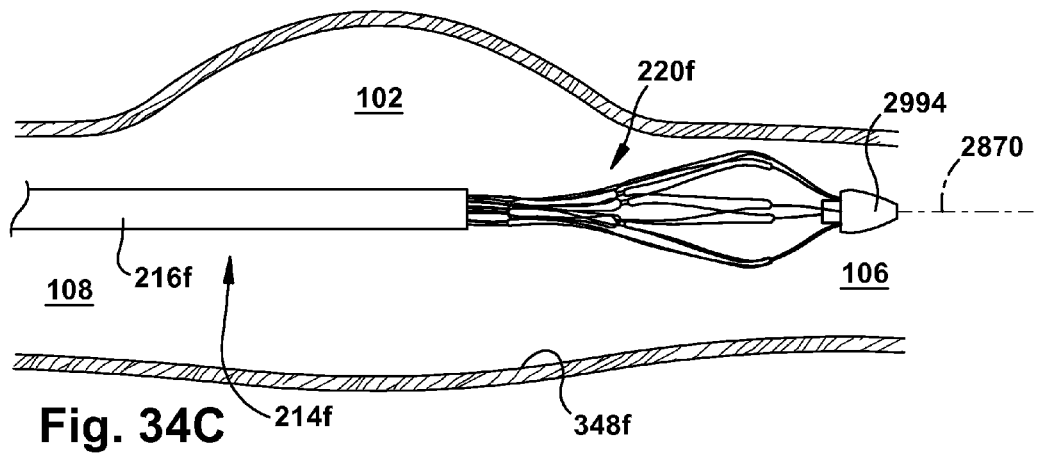
Figure 34D:
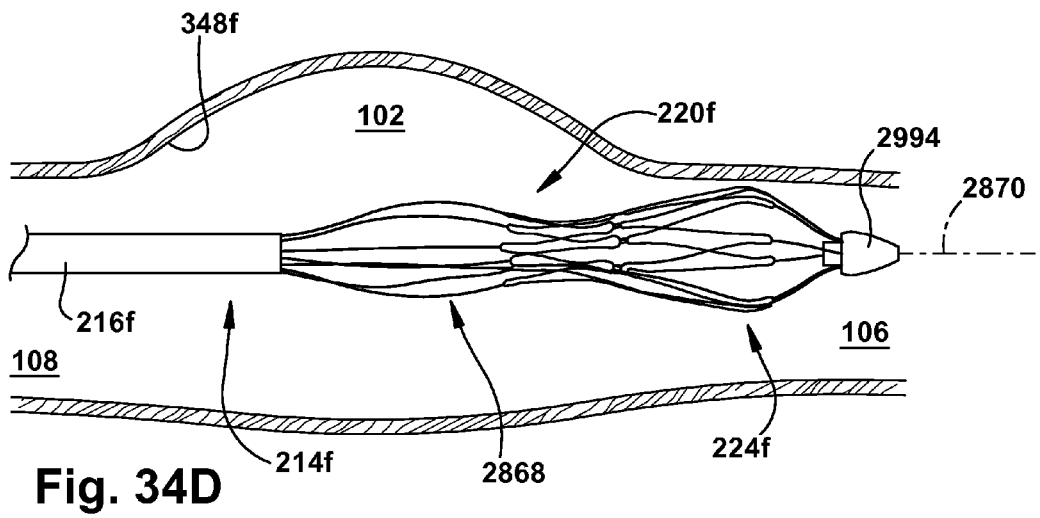
Figure 34E:
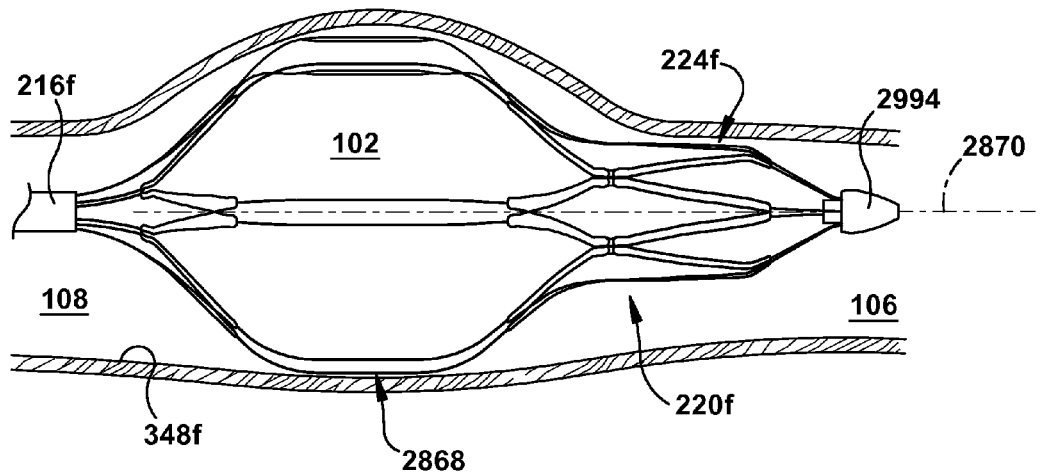

Optionally, and as shown in FIGS. 34B-34D, at least the hub 2994 and the protrusion cap beams 2996 become fully deployed in the expanded condition while the bulbous portion 2868 is still at least partially in the collapsed condition. Accordingly, the protrusion 224f, or portions thereof, may assist with locating and/or steadying the framing member body 226f during deployment of the framing member 220f.

With the protrusion 224f maintained in the expanded condition at the terminal location, possibly helping with anchoring/positioning of the apparatus 214f, the delivery catheter 216f is further retracted to permit the bulbous portion 2868 to extend from the delivery catheter lumen 218f. As the bulbous portion 2868 exits the delivery catheter 216f, it self-expands into the expanded condition within the right atrium 102 and, optionally, exerts force against at least a portion of the body tissue making up the interior right atrium surface 348f. As is apparent in at least FIG. 34E, the expanded framing member 220f has a substantially "onion-dome" shape which mimics the internal contour of the right atrium 102. Once the apparatus 214f, and particularly the framing member 220f, has reached the desired condition, orientation, and configuration within the body cavity, the delivery catheter 216f may optionally be removed and the target points 228f and target wires 230f (omitted from FIGS. 34B-34D for clarity) can be used to locate/indicate a desired target location for puncture or any other desired region.

Once the location/indication is no longer needed, and/or at the conclusion of the surgical procedure, the framing member 220f may be brought into the collapsed condition within the delivery catheter lumen 218f for removal, via advancement of the delivery catheter 216f in the distal direction and/or retraction of the framing member (e.g., via a pull on the target catheter 3278) in the proximal direction. Once constrained at least partially within the delivery catheter 216f, the framing member 220f may be removed from the patient's body.

Figure 35A:
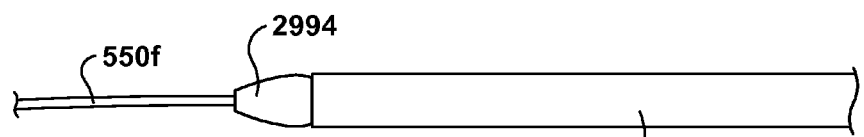
FIGS. 35A-35C depict an example sequence of deployment of the ninth embodiment of FIG. 28.
Figure 35B:
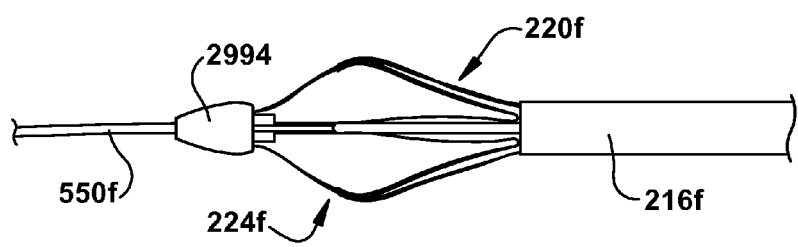
Figure 35C:
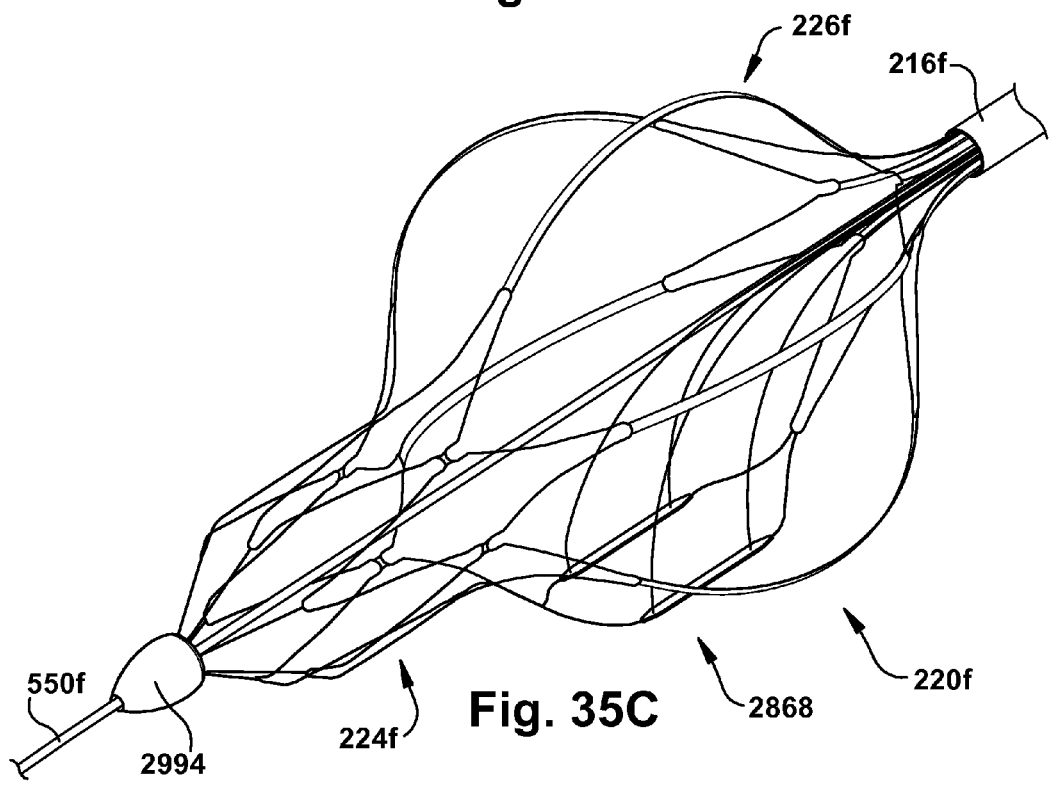

FIGS. 35A-35C depict a sequence of operation similar to that of FIGS. 34A-34E, with the addition of a guidewire 550f. In the configuration of the ninth embodiment shown in FIGS. 35A-35C, the hub 2994 includes a throughbore through which the guidewire 550f, or a small-diameter catheter for accepting a guidewire, can extend, optionally to help with navigation/placement of the apparatus 214f or for any other reason.

FIGS. 36-40C illustrate a tenth embodiment of an apparatus 214g. The apparatus 214g of FIGS. 36-40C is similar to the previously described apparatuses 214, 214', 214", and therefore, structures of FIGS. 36-40C that are the same as or similar to those described with reference to FIGS. 2-35C have the same reference numbers with the addition of the suffix "g". Description of common elements and operation similar to those in the previously described embodiments will not be repeated with respect to the tenth embodiment.

Figure 36:
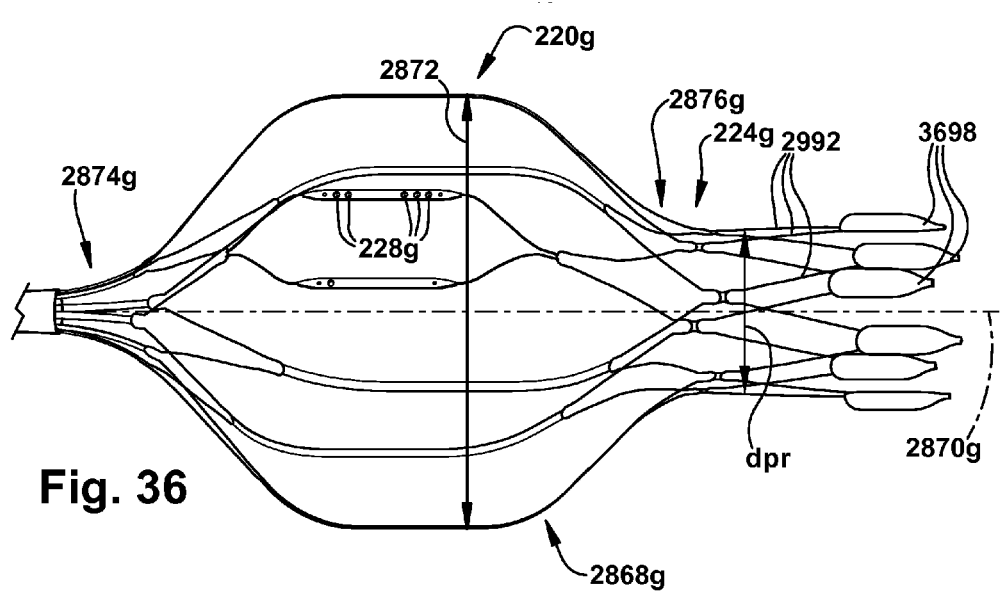
FIG. 36 is a side view of a tenth embodiment of the present invention.
Figure 37:
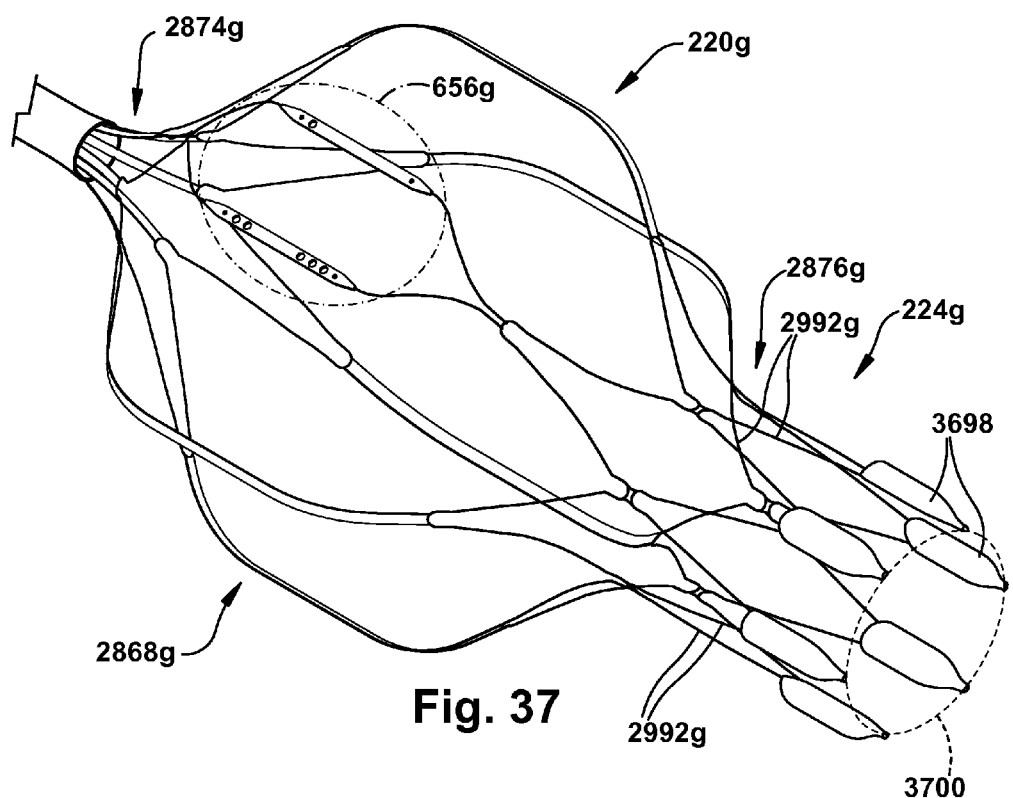
FIG. 37 is a front perspective view of the tenth embodiment of FIG. 36.
Figure 38:
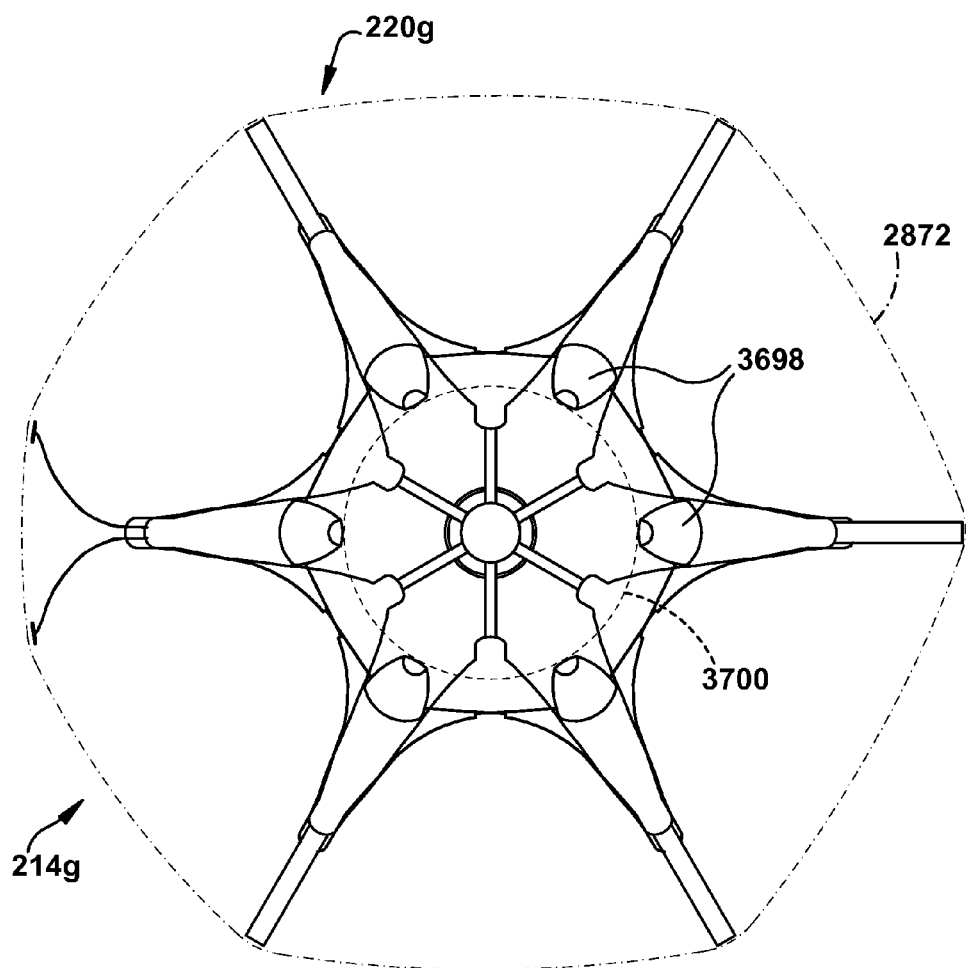
FIG. 38 is a front view of the tenth embodiment of FIG. 36.

In FIGS. 36-38, the protrusion 224g can be readily seen to be of the "open-crown" type. The protrusion 224g has a maximum protrusion diameter $d_{pr}$ which is significantly smaller than the diameter 2872 of the maximum body footprint. The protrusion 224g includes a plurality of protrusion body beams 2992g which extend substantially longitudinally distally from the distal body end 2876g of the bulbous portion 2868g. Each protrusion body beam 2992g extends along/within a plane which is substantially parallel to, and laterally spaced from, the central framing member axis 2870g. That is, though individual ones of the protrusion body beams 2992g are angled with respect to the central framing member axis 2870g, they are each contained within a plane which itself is substantially parallel to, and laterally spaced from, the central framing member axis 2870g—the "topmost" and "bottommost" (in the orientation of FIG. 36) protrusion body beams 2992g, for example, each extend along a plane that is perpendicular to (extends into and out of) the plane of the page.

Each of the protrusion body beams 2992g has a distal body beam end 3698 which is laterally spaced from each other distal body beam end 3698 of the framing member 220g. The distal body beam ends 3698 collectively define a protrusion aperture 3700 (shown schematically in dashed line in FIGS. 37-38) which is substantially concentric to the central framing member axis 2870g. The protrusion aperture 3700 permits substantially unobstructed access longitudinally therethrough along the central framing member axis 2870g to an interior of the bulbous portion 2868g via the distal body end 2876g, hence the characterization of the tenth embodiment as having an "open-crown" protrusion 224g.

Similarly to the closed-crown protrusion 224f of the ninth embodiment, the closed-crown protrusion 224g of the tenth embodiment can at least partially enter a chosen one of the superior vena cava 106 and the inferior vena cava 108 to exert an anchoring force of any suitable type and magnitude, in any desired orientation or direction, upon the chosen one of the superior vena cava and the inferior vena cava or any other body tissue. For example, the protrusion body beams 2992g could at least partially enter the chosen one of the superior vena cava 106 and the inferior vena cava 108 to exert a laterally oriented force outward from the central framing member axis 2870g upon the chosen one of the superior vena cava and the inferior vena cava to substantially prevent movement of the framing member within the right atrium 102 during transition of the framing member 220g from the collapsed condition to the expanded condition and/or during maintenance of the framing member 220g in the expanded condition within the right atrium 102.

Figure 39A:
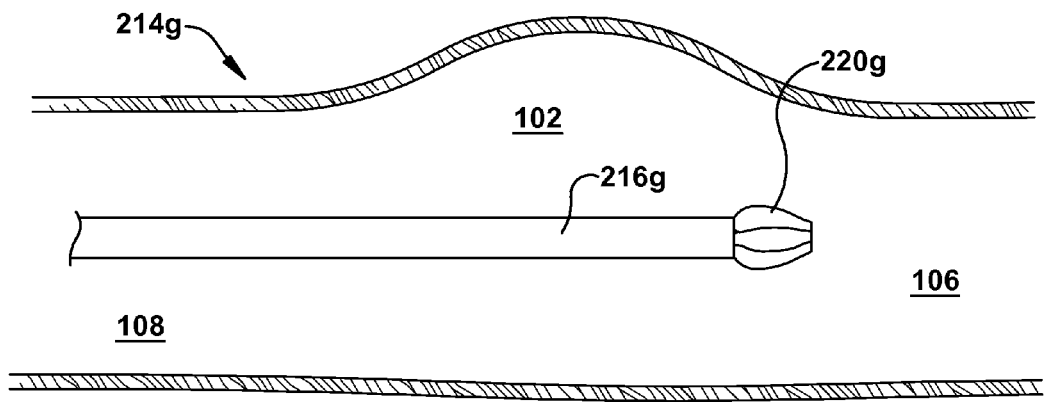
FIGS. 39A-39D depict an example sequence of deployment of the tenth embodiment of FIG. 36.

The sequence of FIGS. 39A-39D, like that of FIGS. 34A-34E for the ninth embodiment, depicts a sequence of operation of the tenth embodiment of the present invention within a right atrium 102 as a body cavity to be targeted. In FIG. 39A, the framing member 220g is in the collapsed condition and is carried into the right atrium 102 within the delivery catheter 216g, with the distalmost (to the right, in the orientation of FIGS. 39A-39D) end of the collapsed framing member placed in the terminal location within the superior vena cava 106.

Figure 39B:
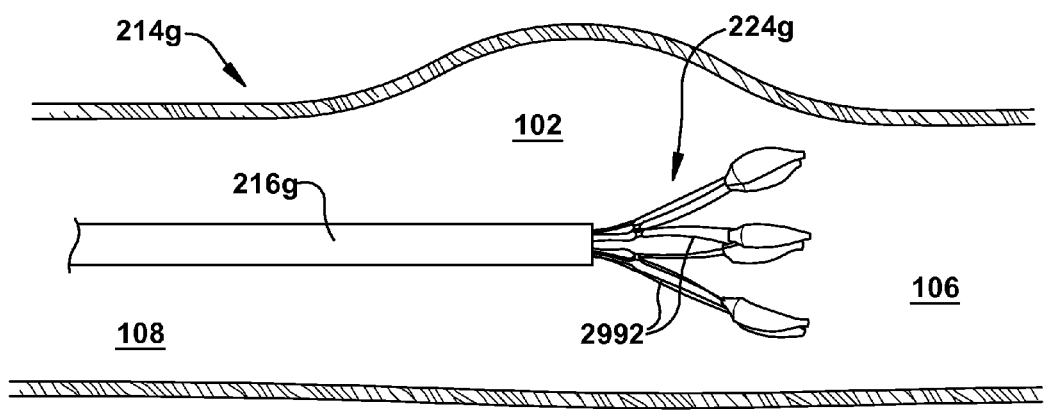
Figure 39C:
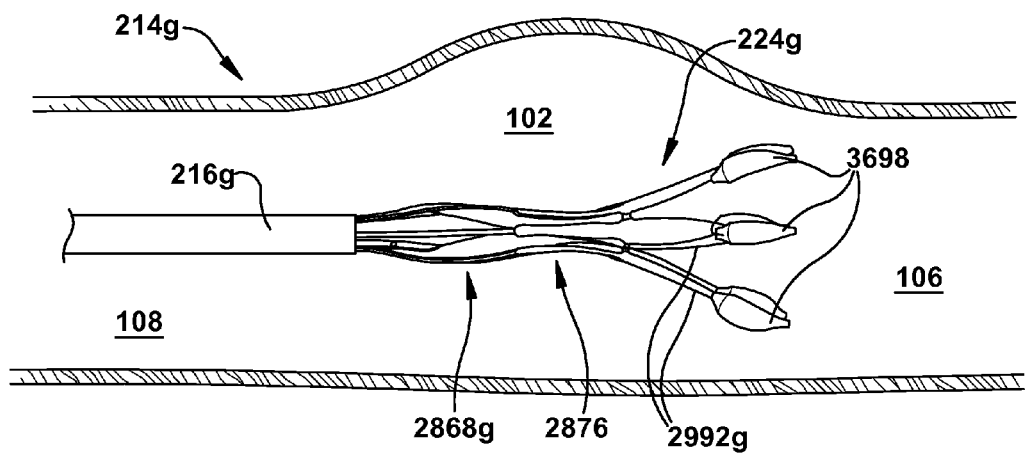

In FIG. 39B, the delivery catheter 216g has been retracted, maintaining the distalmost end of the framing member 220g in the terminal location, to expose the self-expanding open-crown protrusion 224g. It can be seen, in the sequence of FIG. 39B-39C, that the protrusion body beams 2992g have become substantially fully deployed in the expanded condition while the bulbous portion 2868g is still substantially in the collapsed condition.

Figure 39D:
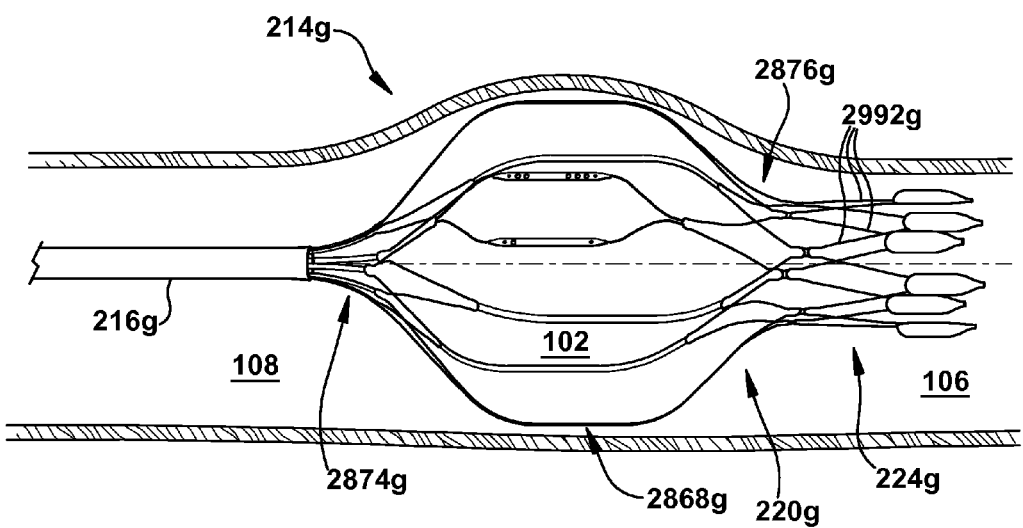

In FIG. 39D, the framing member 220g has been fully expanded and is being maintained in the desired position within the right atrium 102, optionally with the assistance of an interaction between the superior vena cava 106 and the protrusion 224g. The apparatus 214g can then be used as desired and retracted back into the delivery catheter 216g, in any desired fashion, for removal from the patient's body. Unlike the closed-crown protrusion 224f of the ninth embodiment, however, the open-crown protrusion 224g can act in a "pincer"-like manner to grasp matter between the distal body beam ends 3698 (or other structures of the protrusion body beams 2992g) as the protrusion 224g is being collapsed into the delivery catheter 216g. Accordingly, the framing member 220g of the tenth embodiment can additionally have a separate function, other than holding a target array, of grasping and potentially removing material from the body cavity, as desired.

Figure 40A:
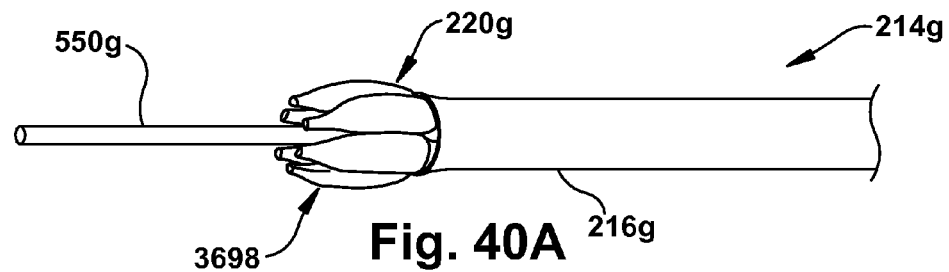
FIGS. 40A-40C depict an example sequence of deployment of the tenth embodiment of FIG. 36.
Figure 40B:
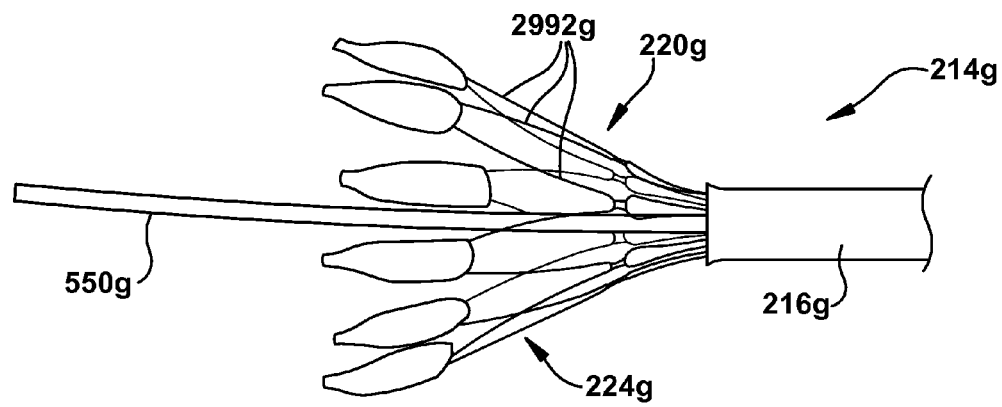
Figure 40C:
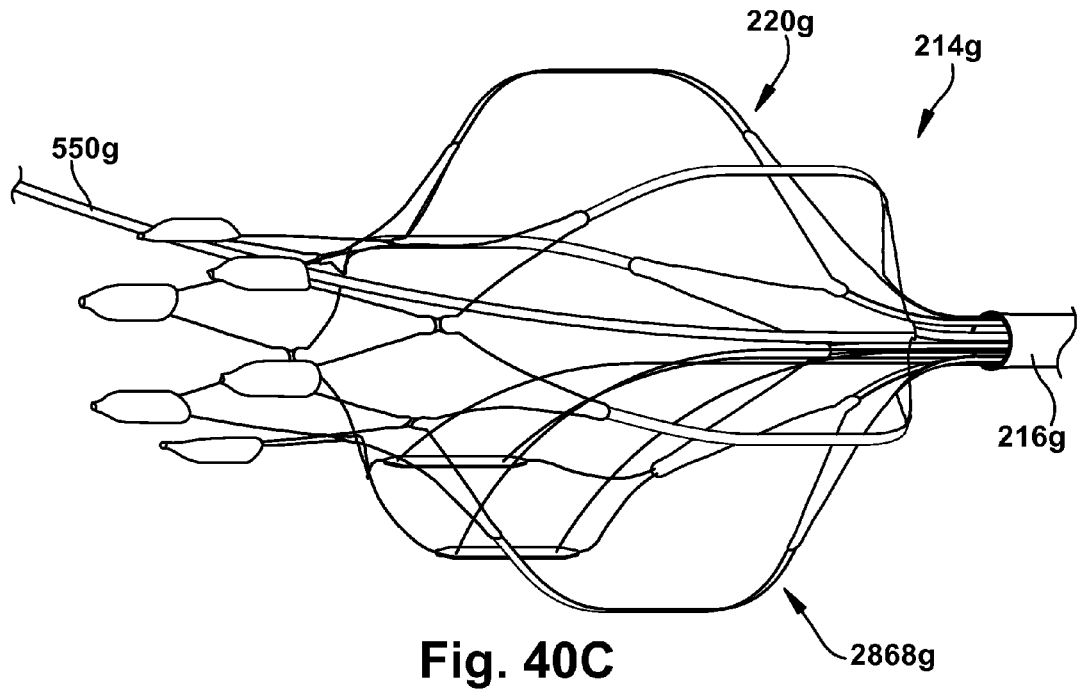

FIGS. 40A-40C depict a sequence of operation similar to that of FIGS. 39A-39D, with the addition of a guidewire 550g. In the configuration of the tenth embodiment shown in FIGS. 40A-40C, the guidewire 550g, or a small-diameter catheter for accepting a guidewire, extends out of the collapsed framing member 220g by exiting a small aperture formed by the distal body beam ends 3698. However, as the protrusion 224g deploys into the expanded condition, the distal body beam ends 3698 release the guidewire 550g, which is then free for lateral movement, as shown in FIG. 40C. For use environments of the present invention in which this lateral guidewire 550g movement is undesirable, the user may choose to remove the guidewire before expanding the framing member 220g, or could instead choose a closed-crown framing member 220f, such as that of the ninth embodiment, instead of the open-crown framing member 220g of the tenth embodiment.

FIGS. 41A-41E depict expansion phenomena that could affect any suitable embodiment of the present invention, but which were particularly encountered during development of the ninth and tenth embodiments of FIGS. 28-40C and which were considered undesirable for use with those embodiments. It is contemplated, though, that these or related phenomena may be beneficial in other embodiments of the present invention, and may be analyzed and applied by one of ordinary skill in the art.

Figure 41A:
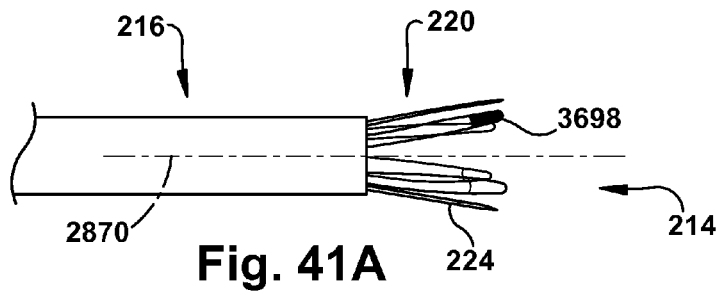
FIGS. 41A-41D depict an example sequence of occurrence of a first phenomenon encountered during design.
Figure 41B:
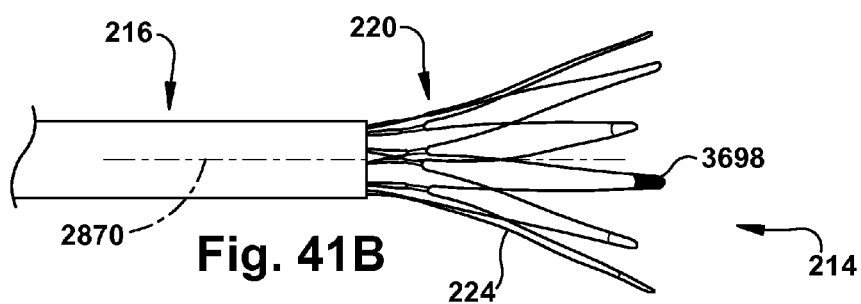
Figure 41C:
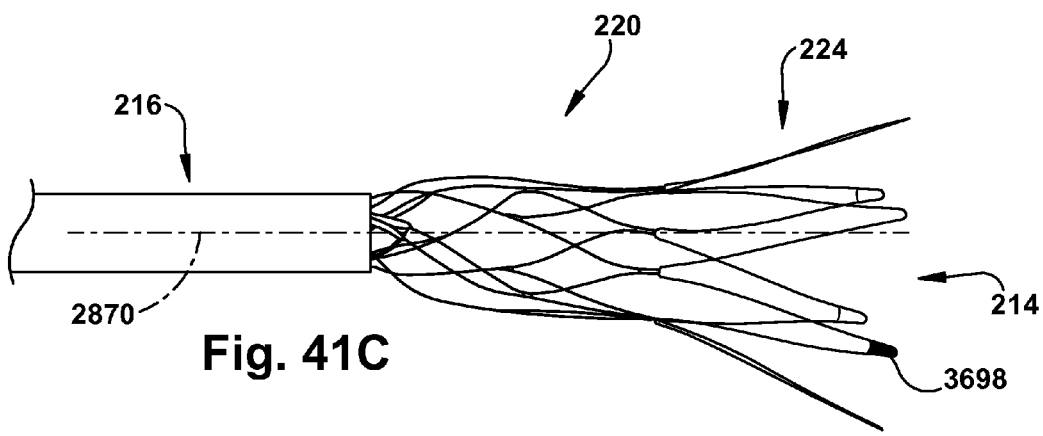
Figure 41D:
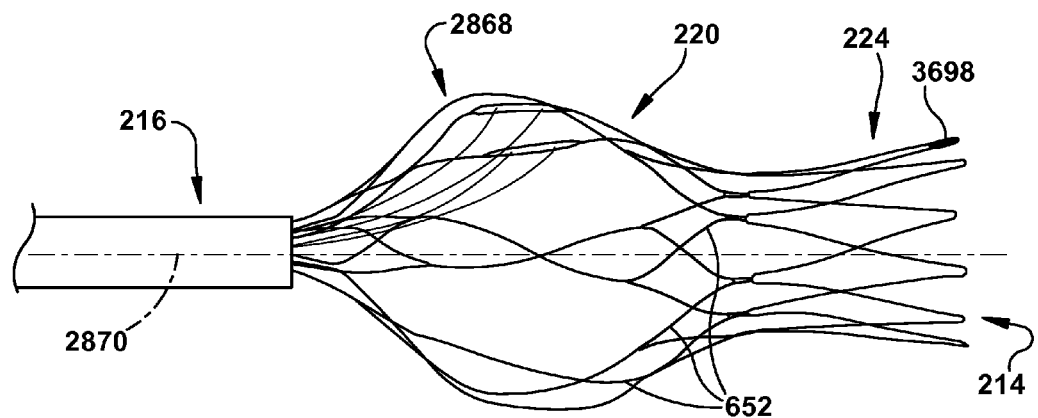

In FIGS. 41A-41D, a sequence of deployment of a framing member 220 into an expanded condition is shown. A selected distal body beam end 3698 is emphasized with a superimposed heavy dot—the dot stays on the same distal body beam end throughout FIGS. 41A-41D. As can be seen by rotational migration of the dot around the central framing member axis 2870, at least a portion of the framing member 220 is moving radially (i.e., in rotation around the central framing member axis) during expansion. Such radial motion may be undesirable as possibly leading to scraping of the framing member 220 across the body tissue, which could damage the body tissue. In addition, FIG. 41D shows how the framing strands 652 in the bulbous portion 2868 are displaced and have become twisted or torqued out of the regular substantial rotational symmetry encountered in the framing member 220g shown in FIGS. 36-38.

Figure 41E:
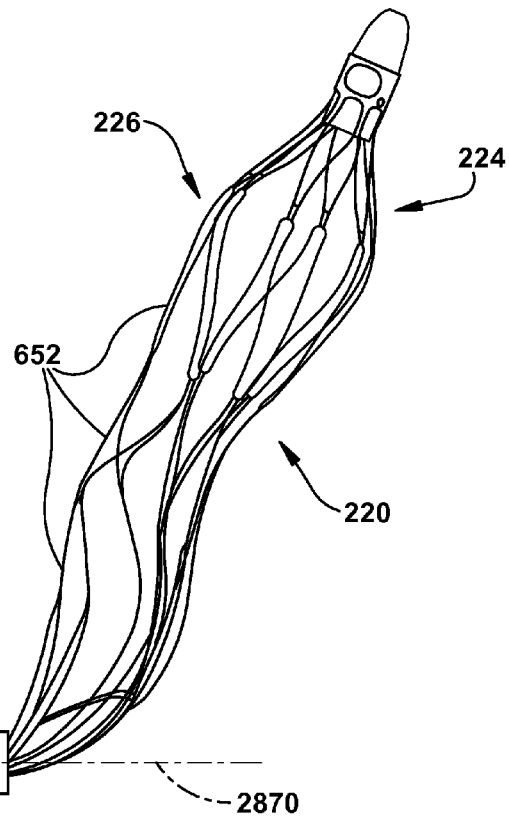
FIG. 41E depicts an example occurrence of a second phenomenon encountered during design.

FIG. 41E shows another phenomenon sometimes encountered with the present invention, wherein almost the entire framing member body 226 has moved laterally in a bending or buckling motion away from the expected position of the central framing member axis 2870.

Both of these twisting and buckling phenomena, which appeared undesirably in the development of the ninth and tenth embodiments of FIGS. 28-40C, were discovered to have arisen from the aspect ratio of the framing strands 652, which are referenced as framing member beams 4202 for ease of discussion herein. Aspect ratio is one consideration which may be taken into account when designing a self-expanding device created from a tube of Nitinol or another shape-memory material as raw material.

FIG. 42 depicts an example of a cross-section of an individual framing member beam 4202, the cross-section taken in a plane substantially perpendicular to the central framing member axis 2870. The width (w) of the framing member beam 4202 corresponds to a distance between laterally adjacent cuts of the raw material Nitinol tube. The thickness (t) of the framing member beam 4202 corresponds to the wall thickness of the raw material Nitinol tube. The aspect ratio is the dimensionless value of the width divided by the thickness.

During development of the ninth and tenth embodiments of FIGS. 28-40C, it was discovered that the aspect ratio applied to the different sections of the cut patterns or incisions in the raw material Nitinol tube could have some effect on the twisting, bending, or other behaviours of the finished framing member 220. The cut patterns for the ninth and tenth embodiments of FIGS. 28-40C are shown in FIGS. 43 and 44A, respectively. (The cut patterns are shown in an "unrolled" condition in the Figures; in actuality, the cut patterns would be incised completely around the diameter of a raw material Nitinol tube oriented horizontally, in the orientation of FIGS. 43 and 44A.)

As shown in FIGS. 43 and 44A, the complex closed- and open-crown "onion dome" shaped framing members 220 of the ninth and tenth embodiments are created by non-overlapping longitudinal sequences of framing member beam arrays 4304 (labeled S1-S6 in FIG. 43 and S1-S5 in FIG. 44A), with each framing member beam array including a plurality of longitudinally aligned and laterally spaced framing member beams 4202 (for clarity, only a few example framing member beams are labeled in the Figures). Each framing member beam array 4304 may include a plurality of framing member beams 4202 that are substantially similar to each other framing member beam in the same framing member beam array—for example, the framing member beams 4202 in array S1 of FIG. 43 are substantially all the same length and width. Minor local irregularities, such as the thickened aspect (to help provide the target points 228) of only two framing member beams 4202 of array S3 of FIGS. 43 and 44A, do not destroy the substantial similarity of those slightly irregular framing member beams as compared to the other framing member beams in the same framing member beam array 4304.

A plurality of framing member beam arrays 4304 collectively make up or form a framing member 220, with longitudinally adjacent framing member beam arrays 4304 being connected via a plurality of framing member nodes 4306 interposed between longitudinally adjacent pairs or groups of framing member beams 4202. The framing member beams 4202 that make up a single framing member 220 substantially each have a width-to-thickness aspect ratio chosen to facilitate self-expansion of the framing member while substantially avoiding both lateral (buckling) and radial (twisting) motion of the framing member with respect to the central framing member axis 2870 during transition of the framing member between the collapsed and expanded conditions. For several embodiments of the present invention, including the ninth and tenth embodiments, that width-to-thickness aspect ratio of all of the framing member beams 4304 of a single framing member 220 falls in the range of from about 0.6 to about 3.0 and, more particularly, in the range of from about 0.75 to about 2.8.

Optionally, and as shown in the Figures, the framing member beams 4202 in a chosen framing member beam array 4304 may have substantially different values in at least one dimension from the framing member beams 4202 in a longitudinally adjacent framing member beam array. For example, and as can be seen in FIG. 43, the framing member beams 4202 of array S2 are shorter, in the longitudinal direction, than the framing member beams of longitudinally adjacent array S3.

Each framing member beam array 4304 may have a substantially cylindrical aspect formed by a laterally circular arrangement of the framing member beams 4202 of that framing member beam array. Stated differently, if the cut patterns shown in FIGS. 43 and 44A were each rolled (as if around a raw material Nitinol tube) about the central framing member axis 2870, the resultant framing members 220 would appear to be substantially circular if viewed end-on along the central framing member axis from the left or right side, in the orientation of FIGS. 43 and 44A.

Figure 45A:
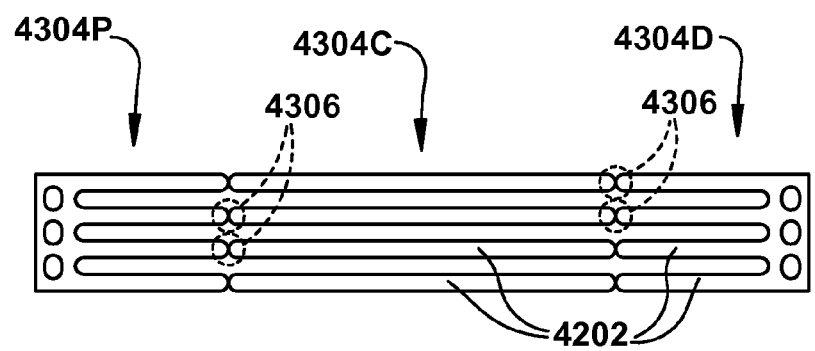
FIGS. 45A-B schematically depict an example configuration of a component of the present invention.
Figure 45B:
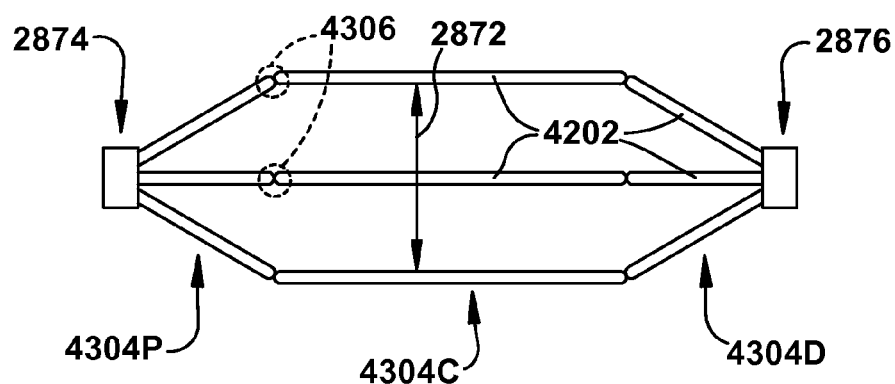

For certain use applications of the present invention and embodiments resembling those of the ninth and tenth embodiments discussed above, a framing member 220 (omitting a protrusion 224) can be provided by as few as three framing member beam arrays 4304 which collectively form the bulbous portion 2868, as shown in FIGS. 45A-45B. A proximal-most framing member beam array 4304P may extend longitudinally between, and be connected to both of, the proximal body end 2874 and a center framing member beam array 4304C. The center framing member beam array 4304C may then extend longitudinally between, and be connected to both of, the proximal-most framing member beam array 4304P and a distal-most framing member beam array 4304D. In this simple three-array arrangement, the center framing member beam array 4304C defines, when the framing member 220 is in the expanded condition shown schematically in FIG. 45B, a substantially cylindrical maximum body footprint shown at 2872. The distal-most framing member beam array 4304D will then extend longitudinally between, and be connected to both of, the center framing member beam array 4304C and the distal body end 2876. Regarding the aspect ratios for this embodiment, a majority of the framing member beams 4202 that make up the proximal-most framing member beam array 4304P may have a width-to-thickness fractional aspect ratio in the range of from about 0.80-0.95 and, more particularly, of from about 0.82-0.92. A majority of the framing member beams 4202 that make up the center framing member beam array 4304C may have a width-to-thickness fractional aspect ratio in the range of from about 0.75-2.8 and, more particularly, of from about 2.5-2.8 (depending in part upon whether any of the framing member beams are also thickened to carry target point(s) 228 or target wires 230, or whether any of the framing member beams are at least partially longitudinally slit). A majority of the framing member beams 4202 that make up the distal-most framing member beam array 4304D may have a width-to-thickness fractional aspect ratio in the range of from about 0.70-0.95 and, more particularly, of from about 0.83-0.92.

In the simple three-bar mechanism type arrangement framing member 220 shown in FIGS. 45A-45B, the transitions between the longitudinally adjacent framing member beam arrays 4304 are relatively abrupt and angular. In contrast, the framing members 220 shown in cut pattern in FIGS. 43 and 44A include a larger number of framing member beam arrays 4304 which may assist with providing a protrusion 224, connecting the framing member 220 to the target catheter wall 3282, and/or connecting those framing member beams 4202 which act as protrusion cap beams 2996 to a hub 2994.

For example, a protrusion 224 located at the distal body end 2876 may be formed by a protrusion framing member beam array 4304 (S5-S6 in the closed-crown version of FIG. 43 and S5 in the open-crown version of FIG. 44A) connected to a distal end of the distal-most framing member beam array (S4 in both of FIGS. 43 and 44A) such that the protrusion extends longitudinally distally from the distal body end 2876 of the bulbous portion 2868. In this arrangement, a majority of the framing member beams 4202 that make up the protrusion framing member beam array 4304 may have a width-to-thickness fractional aspect ratio in the range of from about 0.85-2.12.

As another example of a "refinement" added to the basic three-bar arrangement of FIGS. 45A-45B, a mounting framing member beam array 4304 (S1 in both FIGS. 43 and 44A) may extend longitudinally between, and be connected to both of, the target catheter wall 3282 and a proximal end of the proximal-most framing member 4304 (S2 in both FIGS. 43 and 44A) such that the mounting framing member beam array attaches the framing member to the target catheter wall. Here, a majority of the framing member beams 4202 that make up the mounting framing member beam array 4304 may have a width-to-thickness fractional aspect ratio in the range of 1.5-2.12.

As mentioned above, certain of the framing member beam arrays 4304 shown in FIGS. 43-44A include framing member beams 4202 which function as protrusion body beams 2992 and/or protrusion cap beams 2996. More specifically, the framing member beams 4202 of arrays S5 of both FIGS. 43-44A act as protrusion body beams 2992 in the respective ninth and tenth embodiments, and the framing member beams 4202 of array S6 of FIG. 43 act as protrusion cap beams 2996 in the ninth embodiment.

As shown in the detail view of FIG. 44B, at least one longitudinal slit 4408 (shown here with rounded/drilled ends for stress relief) extending completely through a thickness of the Nitinol material may be placed along at least a portion of a longitudinal length of at least one framing member beam 4202 of a chosen framing member beam array 4304, in order to provide desired stress relief and beam bending properties to the slit framing member beam(s). In FIGS. 43 and 44A, each of the framing member beams 4202 of array S3 has two relatively short longitudinal slits 4408 spaced apart longitudinally at a portion of the framing member beams that is near to the framing member beams of the longitudinally adjacent framing member beam arrays.

Suitable example values for the aspect ratios of arrays S1 in both FIGS. 43 and 44A are in the range of from about 1.5 to about 2.2 and, more particularly, in the range of from about 1.650 to about 1.654. Suitable example values for the aspect ratios of arrays S2 in both FIGS. 43 and 44A are in the range of from about 0.80 to about 0.95 and, more particularly, in the range of from about 0.82 to about 0.92. Suitable example values for each half of cross-section of the longitudinally slit portions of the aspect ratios of arrays S3 in both FIGS. 43 and 44A are in the range of from about 0.75 to about 0.92 and, more particularly, in the range of from about 0.90 to about 0.92. Suitable example values for the aspect ratios of the non-slit portions of arrays S3 in both FIGS. 43 and 44A are in the range of from about 2.0 to about 3.0 and, more particularly, in the range of from about 2.5 to about 2.8, depending in part upon whether any of the framing member beams 4202 are also thickened to carry target point(s) 228 or target wires 230. Suitable example values for the aspect ratios of arrays S4 in both FIGS. 43 and 44A are in the range of from about 0.80 to about 0.95 and, more particularly, in the range of from about 0.910 to about 0.920. Suitable example values for the aspect ratios of arrays S5 in both FIGS. 43 and 44A are in the range of from about 0.80 to about 2.2 and, more particularly, in the range of from about 0.95 to about 1.05. Suitable example values for the aspect ratios of array S6 in FIG. 43 are in the range of from about 1.1 to about 1.6 and, more particularly, in the range of from about 1.13 to about 1.6.

Figure 46A:
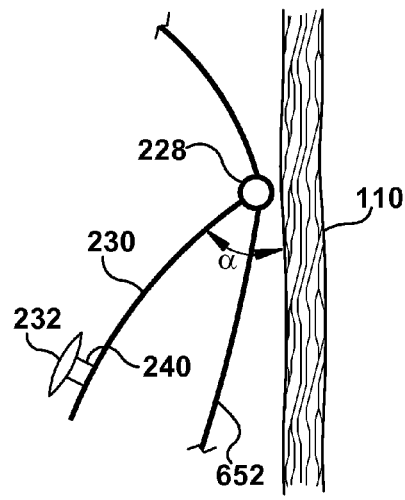
FIGS. 46A-B schematically depict an example sequence of operation of a component of the present invention.
Figure 46B:
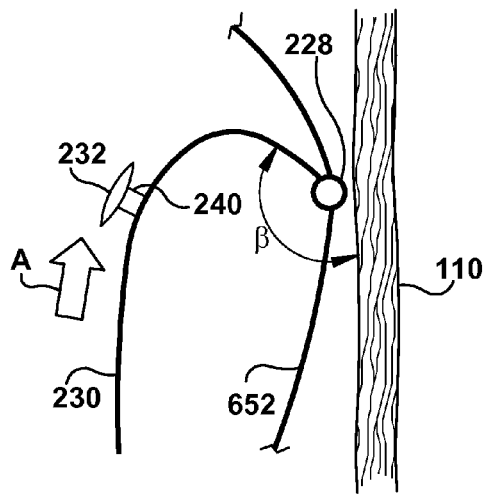

FIGS. 46A-46B schematically depict an option for control of an insertion trajectory of a puncture needle 232 for use with any embodiment of the present invention. In FIGS. 46A-46B, a portion of a single framing strand 652, carrying a single target point 228 is shown in position adjacent a body tissue (here, shown as an interatrial septum 110). A puncture needle 232 is shown as being guided by a target wire 230 and a needle coupler 240, in a monorail-type manner, into puncturing contact with the body tissue. In FIG. 46A, the puncture needle 232 is being guided into puncturing contact at an insertion trajectory angle α, which arises from the angle at which the target wire 230 is attached to, and/or trails away from, the target point 228.

However, if α is not the desired insertion trajectory, the user can manipulate the target wire 230 to change the insertion trajectory of the puncture needle 232 into the body tissue. For example, the user could push the target wire 230 in the direction of arrow A, as shown in FIG. 46B, to "bow" the target wire 230 upward, thus increasing the insertion trajectory to angle β. Any suitable motion with the target wire 230 can be made, whether or not the puncture needle 232 is at or near the target point 228, to place the puncture needle at a desired three-dimensional insertion trajectory with respect to the body tissue. The target wire 230 could be hingedly or pivotally attached to the target point 228 with a suitable mechanism to facilitate any desired insertion trajectory change, or the target wire and/or target point 228 could be relatively rigidly attached (e.g., via welding or soldering) but with enough flexibility in one or both of the attached structures to permit changing of the insertion trajectory as desired.

Figure 47A:
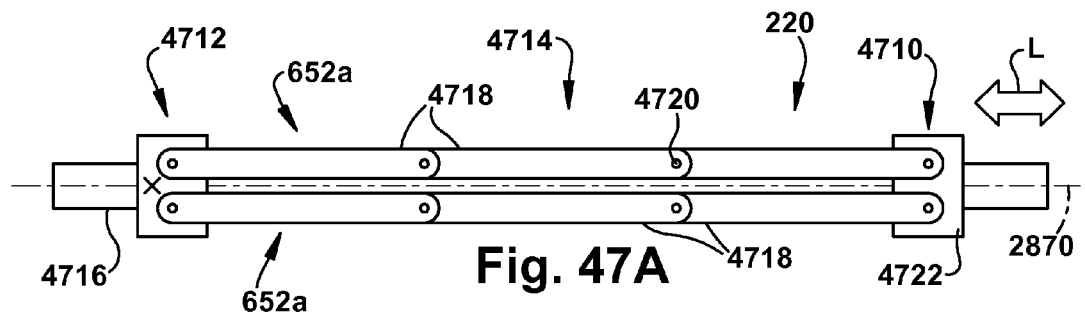
FIGS. 47A-B schematically depict an example configuration of a component of the present invention.
Figure 47B:
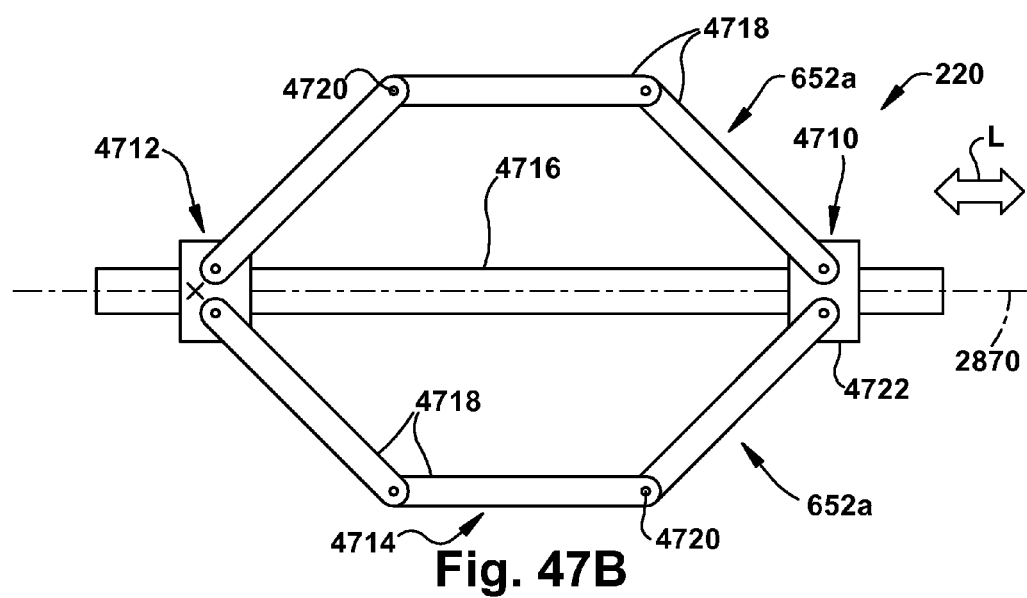

FIGS. 47A-47B schematically depict an option for a linkage-based framing strand 652a which can be used with any embodiment of the present invention. In the aforedescribed embodiments, the framing strands 652, framing member beams 4202, and other longitudinally oriented structures forming the framing member 220 are comprised of a substantially unitary, one-piece, integrally formed piece of material (e.g., Nitinol) which is configured, such as through the cut patterns of FIGS. 43 and 44A, to exhibit particular, predictable two- or three-dimensional bending behaviour when exposed to substantially longitudinally-oriented force (either imposed from without or generated by the material itself, such as the shape-memory properties previously discussed).

In contrast, a framing member 220 shown in FIGS. 47A-47B comprises a plurality of longitudinally extending (i.e., substantially parallel to longitudinal direction L when in the collapsed condition of FIG. 47A) multi-segment framing strands 652a (only two shown in FIGS. 47A-47B for ease of description), which may be radially arranged in an array lateral to the central framing member axis 2870, similarly to the manner in which the plurality of framing member beams 4202 are arranged in the ninth and tenth embodiments of the present invention. Each framing strand 652a has a distal strand end 4710 longitudinally spaced from a proximal strand end 4712 by a strand body 4714. A longitudinal framing member core 4716 defines the central framing member axis 2870. The strand bodies 4714 of the plurality of framing strands 652a each comprise a plurality of substantially rigid strand segments 4718 pivotally connected end-to-end with each other by interposed strand hinges 4720. Optionally, pivot stops (not shown) could be provided to limit the amount of relative pivoting available at each strand hinge 4720 junction.

The proximal and distal strand ends 4710 and 4712 are connected to the central framing member core 4716 with at least one of the proximal and distal strand ends being slidably connected to the central framing member core. For many embodiments of the present invention, only one of the proximal and distal strand ends 4710 and 4712 will be slidably connected to the central framing member core 4716, with the other of the proximal and distal strand ends being held stationary with respect to the central framing member core. The slidable connection may be accomplished in any suitable manner. For example, a sliding cuff 4722 could laterally surround a portion and/or substantially all of the central framing member core 4716, wherein the slidably connected ones of the proximal and distal strand ends 4710 and 4712 of all of the framing strands 652a are connected to the sliding cuff for collective, concurrent longitudinal motion with respect to the central framing member core when the sliding cuff is moved longitudinally with respect to the central framing member core. This is the arrangement shown in FIGS. 47A-47B, with the stationary cuff being marked with an "x".

Another option for facilitating actuation of the framing strands 652a includes the provision of a track or rail system (not shown), with the sliding one(s) of the proximal and distal strand ends 4710 and 4712 being slidably along a track or rail longitudinally arranged in/on the central framing member core. One of ordinary skill in the art will be readily able to provide a track/rail system or any other means for effecting the desired slidable behaviour among the depicted and described structures. Optionally, a portion, but not all, of the framing strands 652a could be connected together in any suitable manner for simultaneous actuation, such that multiple framing member 220 configurations could be produced by the same set of framing strands 652a.

As shown in the transition between FIGS. 47A and 47B, longitudinal movement of the proximal and distal strand ends 4710 and 4712 relatively closer together results in expansion of the framing member 220. The reverse is also true—longitudinal movement of the proximal and distal strand ends 4710 and 4712 relatively further apart results in collapse of the framing member 220. This expansion and collapse can be accomplished en masse, by all of the framing strands 652a at one time, or singly, and will depend at least partially upon how the sliding connection is made. Through control and actuation of the framing strands 652a (individually or as a group) between collapsed and expanded states, the framing member 220 as a whole may be toggled between the collapsed and expanded conditions. More particularly, and viewing a single framing strand 652a, the actuation of that framing strand results in the actuation of a radial portion (i.e., a wedge of the framing member 220 around the central framing member axis 2870) of the framing member into the corresponding expanded or collapsed condition.

The framing strands 652a can be controlled and/or actuated into/between the positions shown in FIGS. 47A-47B in any suitable manner such as, but not limited to, magnetically powered, electrically powered (e.g., electric winches), mechanically powered (e.g., pull strings or push rods), fluidically powered (e.g., pneumatic or hydraulic cylinders), or any other suitable control or actuation means or combination thereof, under automatic and/or manual control/direction.

With a specific example of the ninth embodiment of the present invention, the framing member beams 4202 forming the shape-memory expandable contour/profile of the framing member 220f of that embodiment could be replaced by an appropriately configured framing strand 652a (which need not be made from a shape memory material) of the segment/hinge type shown in FIGS. 47A-47B. The framing strands 652a could be configured to form expanded and collapsed configurations of the framing member 220 substantially similarly to that formed by the shape-memory framing member beams 4202, but instead using the pivoting linkage mechanism shown in FIGS. 47A-47B. For example, the slidably connected ones of the proximal and distal strand ends 4710 and 4712 of each framing strand 652a could be controlled for longitudinal motion along the central framing member core 4716. Such longitudinal motion could then cause the strand segments 4718 of each framing strand 652a to pivot about the strand hinges 4720 relative to one another to move at least one of the bulbous portion 2868 and the protrusion 224f between the expanded condition and the collapsed condition.

Particularly if the bulbous portion 2868 being formed by the framing strands 652a of FIGS. 47A-47B is intended to have a substantially cylindrical maximum body footprint area (e.g., if the structure shown in FIGS. 47A-47B represents just the bulbous portion 2868), or in any other suitable situation, a selected strand segment 4718 of each framing strand 652a (as depicted, the center strand segment) may be located (when the framing member 220 is in the expanded condition) in a plane substantially parallel to, and laterally spaced from, the central framing member axis 2870. In order to achieve the depicted "offset" positioning of the center strand segment 4718, it may be helpful for each included framing strand 652a to include, even consist of, an odd number of substantially rigid strand segments 4718.

As shown in FIGS. 47A-47B, the plurality of framing strands 652a may each include a plurality of strand segments 4718 commensurate in number, longitudinal dimension, orientation and/or any other property with those of each of the other framing strands. In this manner, concurrent actuation of a plurality of framing strands 652a may results in a substantially similar profile, when viewed substantially perpendicular to the central framing member axis 2870 (such as in the view of FIG. 47B), in each of the actuated framing strands. Such uniformity of design may help to provide rotational symmetry in the lateral plane along substantially the entire longitudinal length of the framing member 220.

Another optional feature that could be provided to any embodiment of the present invention may be used to facilitate use of the apparatus 214 in a body cavity having proximal and distal cavity vestibules. For ease of description, the below remarks presume that the body cavity is a right atrium 102, the proximal cavity vestibule is an inferior vena cava 108, and the distal cavity vestibule is a superior vena cava 106, though one of ordinary skill in the art could readily provide an apparatus 214 which performs analogously to that described below for any desired use environment.

As shown in FIG. 48, the apparatus 214 includes some similarities to the apparatuses 214f and 214g of the ninth and tenth embodiments, and similar description and therefore, structures of FIGS. 48-49C that are the same as or similar to those described with reference to FIGS. 1-39C have the same reference numbers with no suffix. Description of common elements and operation similar to those in the previously described embodiments will not be repeated here.

In FIG. 48, the apparatus 214 can be seen to have a distal protrusion 224a located at, and extending longitudinally distally from, the distal body end 2876 of the framing member body 226. A proximal protrusion 224b is located at, and extends longitudinally proximally from, the proximal body end 2874 of the framing member body 226. The proximal protrusion 224b is attached to the target catheter 3278. At least one target point 228 (a target grid 656 shown here) is carried by the framing member body 226 and adapted for placement within the body cavity adjacent the desired target site.

The framing member 220 is dimensioned such that, when in the expanded condition shown in FIG. 48, the proximal and distal protrusions 224a and 224b are configured to at least partially enter the inferior and superior vena cavae 108 and 106, respectively, to resist at least one of radial, longitudinal, and lateral motion of the framing member body 226 within the right atrium 102. The framing member body 226, in turn, is configured and dimensioned for placement within the right atrium 102 while avoiding significant contact with the body tissue forming the wall of the right atrium. While some minimal degree of contact may occur incidentally during placement and/or use of the apparatus 214, the configuration of FIGS. 48-49C is intended to avoid any significant or substantial degree of contact between the framing member body 226 and the interior right atrium surface 348, in at least one dimension.

To facilitate this noncontact placement of the framing member body 226 within the right atrium 102, the target point(s) 228 may be adapted, as well, for noncontact placement, including optional offset allowances, to perform the guiding tasks previously described with the framing member body spaced laterally from the desired target site.

FIGS. 49A-49C depict a sequence of deployment of the framing member body 226 into the described noncontact placement. In FIG. 49A, a delivery catheter 216, containing the framing member 220 in a collapsed condition, is inserted through the right atrium 102 and into the superior vena cava 106. The delivery catheter 216 is retracted to release the distal protrusion 224a to self-expand into its expanded condition in the superior vena cava 106. Optionally, the distal protrusion 224a may be dimensioned to exert a lateral force against the superior vena cava 106 or otherwise resist at least one of radial, longitudinal, and lateral motion of the framing member body 226 within the right atrium 102 through location of at least a portion of the distal protrusion within the superior vena cava.

The delivery catheter 216 is then further withdrawn, into the arrangement shown in FIG. 29B, wherein at least a portion of the framing member body 226 is released and permitted to self-expand into the expanded condition within the right atrium 102. The framing member body 226 should be dimensioned to substantially avoid contact with the interior right atrium surface 348.

Finally, in FIG. 49C, the delivery catheter 216 is then further retracted to release the proximal protrusion 224b to self-expand into its expanded condition in the inferior vena cava 108. Optionally, the proximal protrusion 224b may be dimensioned to exert a lateral force against the inferior vena cava 108 or otherwise resist at least one of radial, longitudinal, and lateral motion of the framing member body 226 within the right atrium 102 through location of at least a portion of the proximal protrusion within the inferior vena cava.

The apparatus 214 may remain in the deployed or expanded configuration shown in FIG. 49C as long as desired, and then may once again be placed in the collapsed configuration within the delivery catheter 216, in any desired manner, for removal once the desired noncontact targeting tasks have been performed.

Though cardiovascular applications and environments of the apparatus 214 are given as examples above, it is contemplated that the present invention may be used in any medical application (for example, insertion through the mouth/esophagus and puncturing from the stomach to the peritoneal cavity), or even nonmedical applications (for example, insertion through an electrical conduit and puncturing from the conduit into an adjacent space between wall studs), as appropriate; any procedure requiring relatively precise location of a target site could be a suitable environment for use of the present invention. For example, body cavities with which the apparatus 214 can be used include, but are not limited to, at least one of a left atrium, a right atrium, a peritoneal cavity, a chest cavity, a left atrial appendage, a right atrial appendage, a left pulmonary vein, a blood vessel, a common iliac artery, a subintimal space, a portion of the heart, a gastrointestinal organ, a genitourinary organ, a space external to the patient's body, and the like. Similarly, the body tissue may be, but is not limited to, at least one of an interatrial septum, a left atrial appendage wall, a right atrial appendage wall, a left pulmonary vein wall, a chest wall, an abdominal wall, a heart wall, a blood vessel wall, a common iliac artery wall, a gastrointestinal organ wall, a genitourinary organ wall, a skin of the patient, and the like. Indeed, a puncture need not always be the end result of using the present invention—the apparatus 214 could be applied instead, as discussed throughout, to simply precisely locate (and optionally mark) a specific area within a difficult-to-access structure.

It is also contemplated that, though the apparatus 214 is described as extending, in some example use environments, from an internal body location all the way outside the patient's body, a second catheter, guidewire, trocar, stent, or the like (not shown) could be used to enter the patient's body from externally in any manner, and at least a portion of the apparatus 214 could be linked with that second catheter, guidewire, trocar, stent, or the like inside the patient's body. In this manner, the apparatus 214 can assist in placing the internal body location in communication with an external structure, while the apparatus 214, or portions thereof, does not actually exit the patient's body.

It is contemplated that, when the apparatus 214 or portions thereof are self-expanding, those self-expanding portions may be at least partially made of a shape-memory material, such as, but not limited to, Nitinol. Particularly for the ninth and tenth embodiments of the present invention, though optionally for any embodiment (whether or not depicted herein), the shape-memory material making up at least a portion of the apparatus 214 may have an Af-temperature value in the range of about 15-30° Celsius and, more particularly, 15-20° Celsius. Af-temperature is a concept used in the working of shape-memory materials, particularly Nitinol and describes the final temperature at which a certain shape is re-gained by the Nitinol device. The Af-temperature of a Nitinol device is controlled/imparted by heat treatments, either directly during the shape-setting step of manufacture or done at a later point in an "aging" process, which can also be done by a controlled application of heat (generally 400° Celsius or higher) to the Nitinol device. The "setting" of an Af-temperature for a Nitinol device is very dependent upon the particular configuration, dimensions, desired behaviour, and other design/manufacturing considerations for a particular device.

With respect to the present invention, three main considerations were at issue in determining the desired Af-temperature range of 15-30° Celsius for some use applications of at least the ninth and tenth embodiments of the present invention. First, an apparatus 214 having a higher Af-temperature than that range will feel very "soft" and therefore will only be able to exert very low radial forces when in the expanded condition, possibly resulting in the apparatus 214 having difficulty exerting the aforementioned forces upon the body tissue. Second, an apparatus having a lower Af-temperature than that range will be very "stiff" or "rigid" and may be difficult to move from the expanded to the collapsed conditions and/or may exert higher-than-desired forces upon the body tissue. Third, operating rooms are generally kept appreciably cooler than a "standard" room temperature of about 25° Celsius. Since the apparatus 214 will often be prepared for insertion within this relatively low-temperature environment, a desired Af-temperature range will generally be one in which the apparatus 214 does not suffer plastic deformation when handled at the relatively low temperatures in the operating room.

The present invention may include features similar to those disclosed in one or more of U.S. Provisional Patent Application Ser. No. 60/850,147, filed 6 Oct. 2006; U.S. patent application Ser. No. 11/867,774, filed 5 Oct. 2007 (now U.S. Pat. No. 8,019,404, issued 13 Sep. 2011); U.S. patent application Ser. No. 13/206,639, filed 10 Aug. 2011; U.S. Provisional Patent Application Ser. No. 61/716,690, filed 22 Oct. 2012; U.S. Provisional Patent Application Ser. No. 61/716,693, filed 22 Oct. 2012; U.S. Provisional Patent Application Ser. No. 61/716,699, filed 22 Oct. 2012; U.S. Provisional Patent Application Ser. No. 61/716,705, filed 22 Oct. 2012; U.S. Provisional Patent Application Ser. No. 61/716,716, filed 22 Oct. 2012; U.S. Provisional Patent Application Ser. No. 61/716,723, filed 22 Oct. 2012; U.S. patent application Ser. No. 14/060,274, filed 22 Oct. 2013; U.S. patent application Ser. No. 14/060,231, filed 22 Oct. 2013; all of which are titled "Apparatus and Method of Targeting a Body Tissue"; and U.S. Provisional Patent Application Ser. No. 61/716,651, filed 22 Oct. 2012 titled "Method and Apparatus for Insertion into a Body Cavity"; all of which are incorporated herein by reference in their entireties.

While aspects of the present invention have been particularly shown and described with reference to the preferred embodiment above, it will be understood by those of ordinary skill in the art that various additional embodiments may be contemplated without departing from the spirit and scope of the present invention. For example, the framing member 220, or the framing strands 652 thereof, may have any suitable shape, cross-sectional or otherwise (e.g., the framing member could have a generally tubular aspect provided by loops of framing strands or could resemble a conventional stent). The framing member 220, or the framing strands 652 thereof, may self-expand through the use of memory alloy materials, magnetic attraction/repulsion, or any other desired mechanism. The functions of the framing strands 652 and target wires 230 may be combined in a single structure. A wireless system may selectively provide an electrical signal to the target points 228 similarly to the target wire 230 system. Any number of target points 228 in a target grid 656 may have associated target wires 230. One or more framing members 220 may have a protrusion 224 adapted to enter the superior vena cava 106 or another defined body structure and thereby help position the apparatus 214 in a desired orientation. The framing cross members 654e may be self-expanding and be restrained by the framing strands 652e. The plurality of target points 228 need not be matched in shape, size, attachment method, conductivity, or any other property. The catheter 216 may follow the framing member 220 through the body tissue, or the catheter 216 may remain within the first body cavity. The framing member 220 may extend through a series of body cavities after facilitating punctures through multiple body tissues. Only one apparatus 214 is shown as being present in the embodiments described and shown herein, but any number of apparatus 214 may be used at a time, as desired for a particular application of the present invention. The apparatus 213 could assist in puncturing outward from a first body cavity to a second body cavity, and then successively inward to the first body cavity again. The specific methods described above for using the apparatus 214 are merely illustrative; one of ordinary skill in the art could readily determine any number of tools, sequences of steps, or other means/options for placing the above-described apparatus, or components thereof, into positions substantively similar to those shown and described herein. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications of the present invention. The framing member 216, or portions thereof, could be balloon- or other external force-expanding, rather than self-expanding. The protrusion 224 could assist with a "self-centering" function for the framing member 216 by moving the collapsed bulbous portion 2868 laterally as the protrusion 224 is deployed and enters the expanded condition. Though certain components described herein are shown as having specific geometric shapes, all structures of the present invention may have any suitable shapes, sizes, configurations, relative relationships, cross-sectional areas, or any other physical characteristics as desirable for a particular application of the present invention. Unless otherwise specifically stated, contact could be either direct or indirect, though even directly-contacting structures may be shown spaced apart in the Figures for clarity of depiction. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, we claim:

1. An apparatus for targeting a desired target site on a body tissue comprising a wall of a first body cavity of a patient, the apparatus comprising:
   a target catheter having a longitudinally extending target catheter lumen surrounded by a tubular target catheter wall having an outer surface;
   a framing member having a collapsed condition in which the framing member is adapted for insertion into the first body cavity and an expanded condition in which the framing member is adapted for placement within the first body cavity, the framing member, when deployed into the expanded condition, having:
   a framing member body which includes a three-dimensionally bulbous portion defining a maximum body footprint in a lateral dimension and having longitudinally spaced proximal and distal body ends which are both longitudinally spaced from the maximum body footprint, a diameter of the bulbous portion being significantly smaller at the proximal and distal body ends than at the maximum body footprint, the proximal body end being attached to the outer surface of the target catheter wall;
   at least one target point carried by the framing member and adapted for placement adjacent the desired target site; and
   at least one target pathway attached to at least one target point, at least a portion of the target pathway extending through the target catheter lumen, and the target pathway being substantially spaced apart from the framing member body;
   wherein the framing member is comprised of a plurality of framing member beams, with at least three framing member beam arrays of framing member beams arranged in non-overlapping longitudinal sequence to form at least a portion of the framing member; and
   wherein the framing member beams that make up the framing member substantially each have a width-to-thickness fractional ratio in the range of 0.6-3.0.

2. The apparatus of claim 1, wherein each framing member beam array includes a plurality of framing member beams that are substantially similar to each other framing member beam in the same framing member beam array, the framing member beams in a chosen framing member beam array having substantially different values in at least one dimension from the framing member beams in a longitudinally adjacent framing member beam array, and each framing member beam array having a substantially cylindrical aspect formed by a laterally circular arrangement of the framing member beams of that framing member beam array.

3. The apparatus of claim 2, wherein:
   a proximal-most framing member beam array extends longitudinally between, and is connected to both of, the proximal body end and a center framing member beam array;
   the center framing member beam array extends longitudinally between, and is connected to both of, the proximal-most framing member beam array and a distal-most framing member beam array, the center framing member beam array defining, when the framing member is in the expanded condition, a substantially cylindrical maximum body footprint; and the distal-most framing member beam array extends longitudinally between, and is connected to both of, the center framing member beam array and the distal body end.

4. The apparatus of claim 3, wherein a majority of the framing member beams that make up the proximal-most framing member beam array have a width-to-thickness fractional ratio in the range of 0.80-0.95, a majority of the framing member beams that make up the center framing member beam array have a width-to-thickness fractional ratio in the range of 0.75-2.8, and a majority of the framing member beams that make up the distal-most framing member beam array have a width-to-thickness fractional ratio in the range of 0.70-0.95.

5. The apparatus of claim 3, wherein a protrusion is located at the distal body end and is formed by a protrusion framing member beam array connected to a distal end of the distal-most framing member beam array such that the protrusion extends longitudinally distally from the distal body end of the bulbous portion, a majority of the framing member beams that make up the protrusion framing member beam array have a width-to-thickness fractional ratio in the range of 0.85-2.12, and when the framing member is in the expanded condition, the protrusion has a diameter which is smaller than the diameter of the maximum body footprint.

6. The apparatus of claim 3, wherein a mounting framing member beam array extends longitudinally between, and is connected to both of, the target catheter wall and a proximal end of the proximal-most framing member such that the mounting framing member beam array attaches the framing member to the target catheter wall, a majority of the framing member beams that make up the mounting framing member beam array have a width-to-thickness fractional ratio in the range of 1.5-2.12.

7. The apparatus of claim 1, wherein at least one framing member beam of a chosen framing member beam array includes at least one longitudinal slit along a portion of a longitudinal length of the at least one framing member beam.

8. The apparatus of claim 1, wherein the framing member is substantially rotationally symmetrical.

9. The apparatus of claim 1, including a delivery catheter having a delivery catheter lumen extending longitudinally between proximal and distal delivery catheter ends, the delivery catheter lumen being configured to substantially laterally surround the framing member in the collapsed condition, at least one target point, and at least one target wire to carry the collapsed framing member, at least one target point, and at least one target wire to the first body cavity of the patient, and the framing member, at least one target point, and at least one target wire exiting distally from the distal delivery catheter end for deployment in the first body cavity of the patient.

10. The apparatus of claim 1, including a puncture needle adapted for insertion through the target catheter lumen and into the first body cavity, the puncture needle having a first needle end operative to puncture the body tissue at the target site.

11. The apparatus of claim 1, including a puncture needle guided by the target pathway and adapted for insertion through the target catheter lumen and into the first body cavity, the puncture needle having a first needle end operative to puncture the body tissue responsive to guidance by the target pathway.

12. The apparatus of claim 1, wherein at least one target point has an associated radiopaque marker to indicate a position of the target point relative to the body tissue in cooperation with an external imaging system.

13. The apparatus of claim 1, wherein the first body cavity is at least one of a left atrium, a right atrium, a peritoneal cavity, a chest cavity, a left atrial appendage, a right atrial appendage, a left pulmonary vein, a blood vessel, a common iliac artery, a subintimal space, a portion of the heart, a gastrointestinal organ, a genitourinary organ, and a space external to the patient's body.

* * * * *